United States Patent
Todd et al.

(10) Patent No.: US 12,123,051 B2
(45) Date of Patent: Oct. 22, 2024

(54) NUCLEIC ACID RATIO DETERMINATION

(71) Applicant: SpeeDx Pty Ltd, Eveleigh (AU)

(72) Inventors: Alison Velyian Todd, Glebe (AU); Nicole Elizabeth Lima, Cremorne (AU)

(73) Assignee: SPEEDX PTY LTD, Eveleigh (AU)

( * ) Notice: Subject to any disclaimer, the term of this patent is extended or adjusted under 35 U.S.C. 154(b) by 874 days.

(21) Appl. No.: 16/619,932

(22) PCT Filed: Dec. 21, 2018

(86) PCT No.: PCT/AU2018/051406
§ 371 (c)(1),
(2) Date: Dec. 5, 2019

(87) PCT Pub. No.: WO2019/119072
PCT Pub. Date: Jun. 27, 2019

(65) Prior Publication Data
US 2020/0199651 A1 Jun. 25, 2020

(30) Foreign Application Priority Data
Dec. 21, 2017 (AU) ................................ 2017905138

(51) Int. Cl.
*C12Q 1/686* (2018.01)
*C12Q 1/18* (2006.01)
*C12Q 1/6851* (2018.01)
*G16B 20/00* (2019.01)
*G16B 25/10* (2019.01)
*G16B 25/20* (2019.01)

(52) U.S. Cl.
CPC .............. *C12Q 1/686* (2013.01); *C12Q 1/18* (2013.01); *C12Q 1/6851* (2013.01); *G16B 20/00* (2019.02); *G16B 25/10* (2019.02); *G16B 25/20* (2019.02)

(58) Field of Classification Search
None
See application file for complete search history.

(56) References Cited

U.S. PATENT DOCUMENTS 9,694,049 B2 * 7/2017 Burkin .................... G01N 33/15
2009/0305274 A1 12/2009 Gygax et al.

FOREIGN PATENT DOCUMENTS

| AU | 2004266311 A1 * | 3/2005 | ........... C12N 15/113 |
| CA | 2763608 A1 * | 12/2010 | ........... C12Q 1/6809 |
| CA | 2979373 A1 * | 3/2018 | ......... A61K 31/4439 |
| EP | 0910666 | 8/2006 | |
| WO | WO 2001/20041 | 3/2001 | |
| WO | WO-2011109901 A1 * | 9/2011 | ............ C12Q 1/689 |
| WO | WO 2011/140237 A2 | 11/2011 | |
| WO | WO 2012/171997 A1 | 12/2012 | |

OTHER PUBLICATIONS

Laurell H, Iacovoni JS, Abot A, Svec D, Maoret J-J, Arnal J-F, Kubista M. 2012. Correction of RT-qPCR data for genomic DNA-derived signals with Valid Prime. Nucleic Acids Research 40:7, e51. DOI: 10.1093/nar/gkr1259 (Year: 2012).*
Laurell et al., "Correction of RT-qPCR data for genomic DNA-derived signals with ValidPrime," Nucleic Acids Research, 40(7):e51, 10 pages, (2012).
Leung et al., "A quantitative-PCR based method to estimate ranavirus viral load following normalisation by reference to an ultraconserved vertebrate target," Journal of Virological Methods, 249:147-155, (2017).
Padhi et al., "A PCR-based approach to assess genomic DNA contamination in RNA: Application to rat RNA samples," Analytical Biochemistry, 494:49-51, (2016).
WIPO Application No. PCT/AU2018/005140, PCT International Search Report mailed Feb. 8, 2019.
WIPO Application No. PCT/AU2018/005140, PCT Written Opinion of the International Searching Authority mailed Feb. 8, 2019.
Shimada et al., "Normalization using ploidy and genomic DNA copy numer allows absolute quanification of transcripts, proteins and metabolites in cells," Plant Methods, 6:29, (2010).
EP 18891196.0 European Search Opinion completed Aug. 12, 2021.
EP 18891196.0 Supplemental European Search Report completed Aug. 12, 2021.

* cited by examiner

*Primary Examiner* — Soren Harward
*Assistant Examiner* — Robert James Kallal
(74) *Attorney, Agent, or Firm* — Alston & Bird LLP

(57) ABSTRACT

The present invention provides methods for quantitative data normalisation, and/or ascertaining levels of transcription in cells, organisms, viruses, and the like. The methods can be used in numerous applications including, but not limited to, determining transcriptional upregulation and downregulation, identifying transcriptional perturbation, determining viability/death, and assessing responses to treatment with agents (e.g. resistance or sensitivity to drugs).

20 Claims, 13 Drawing Sheets

Specification includes a Sequence Listing.

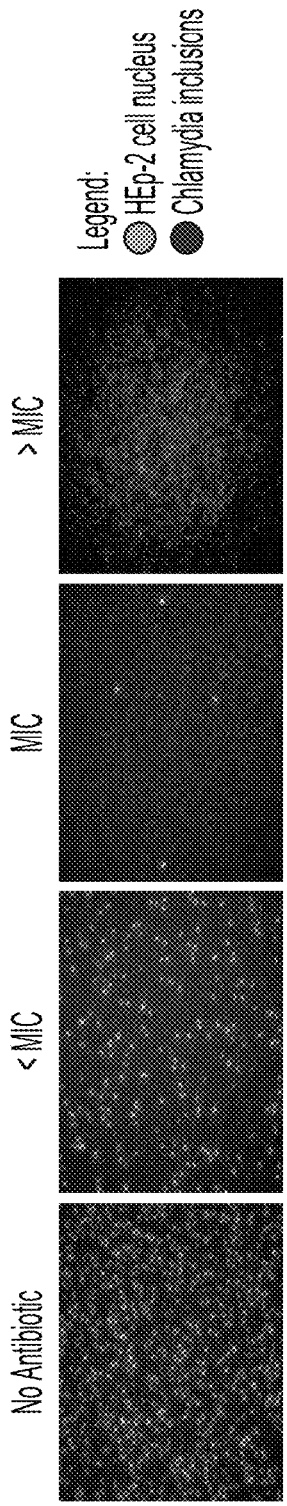
FIG. 3A
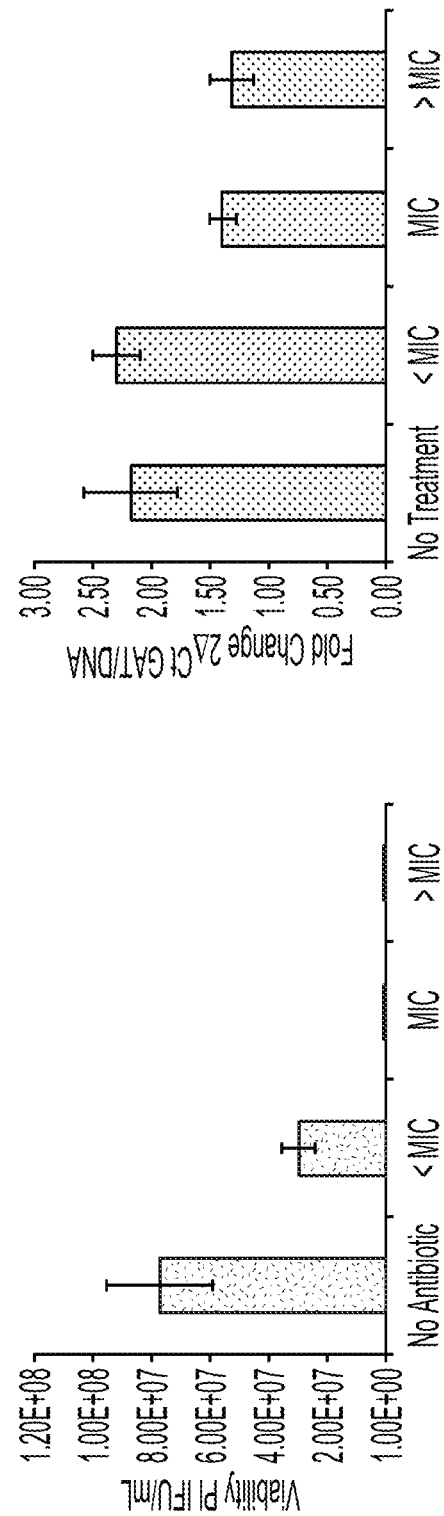
FIG. 3B
FIG. 3C

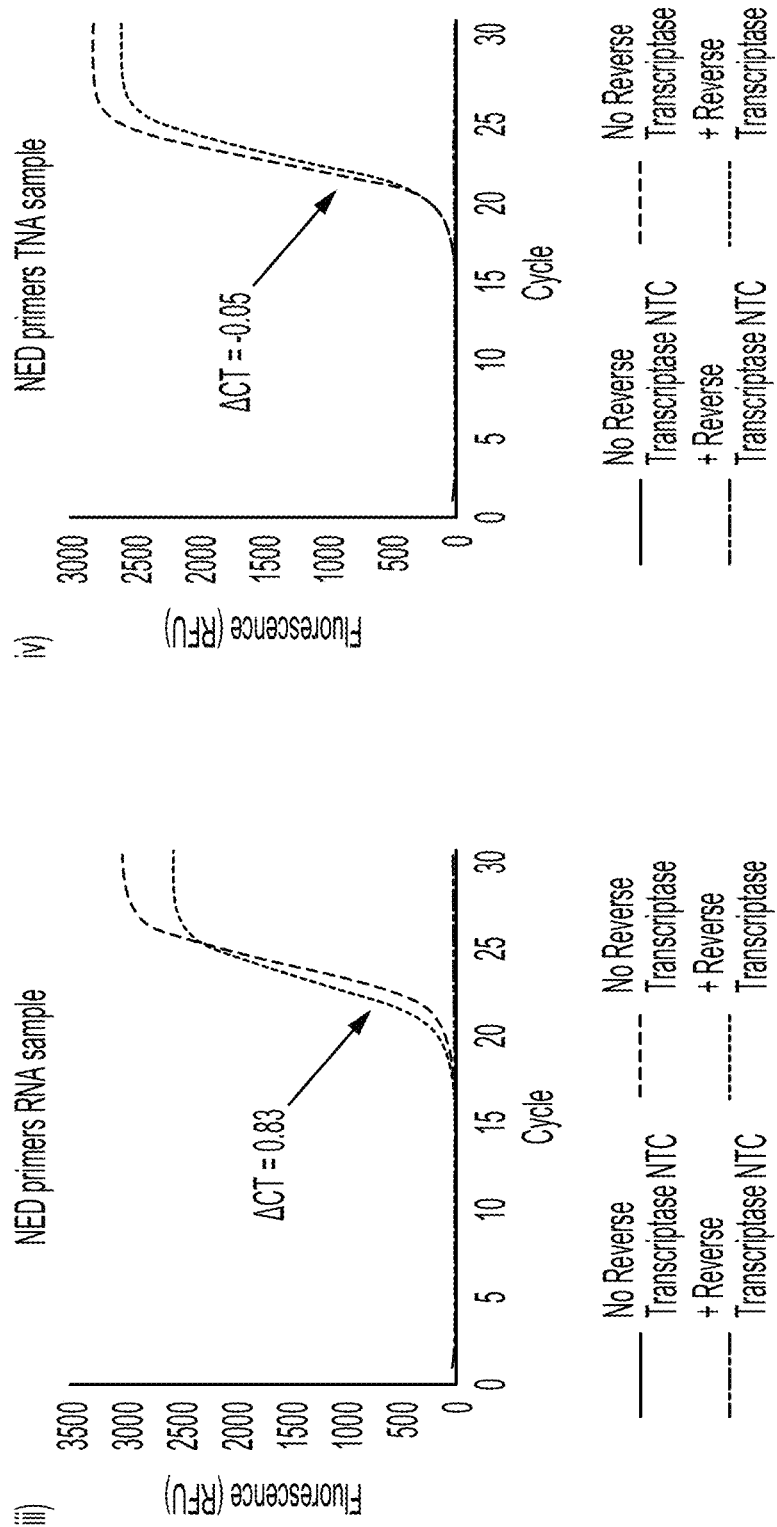

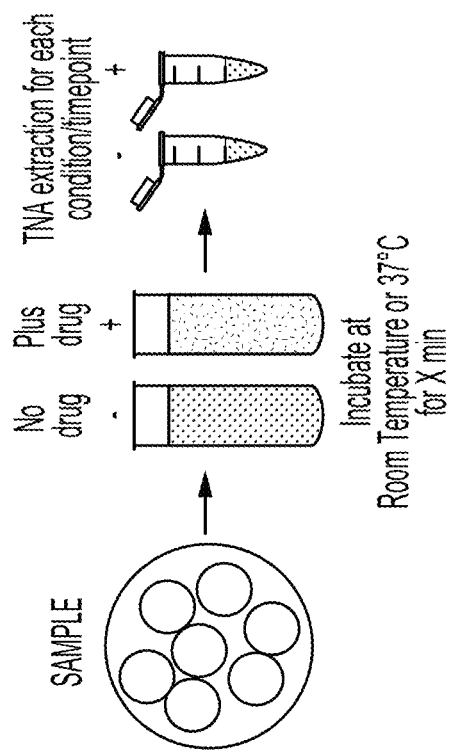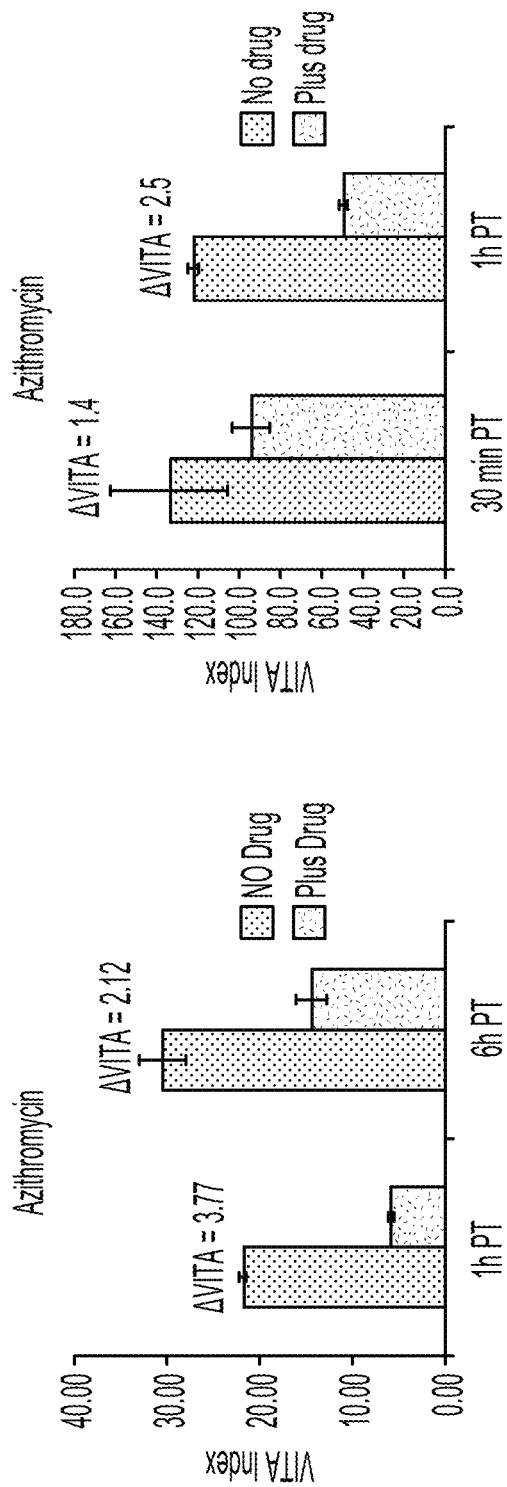
FIG. 7A
FIG. 7B
FIG. 7C

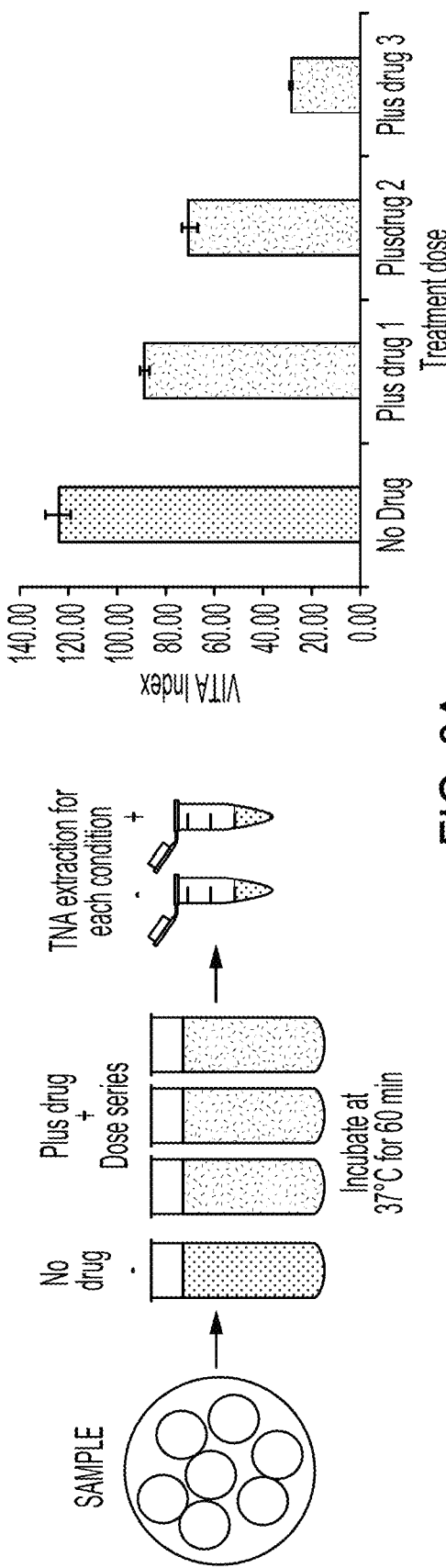
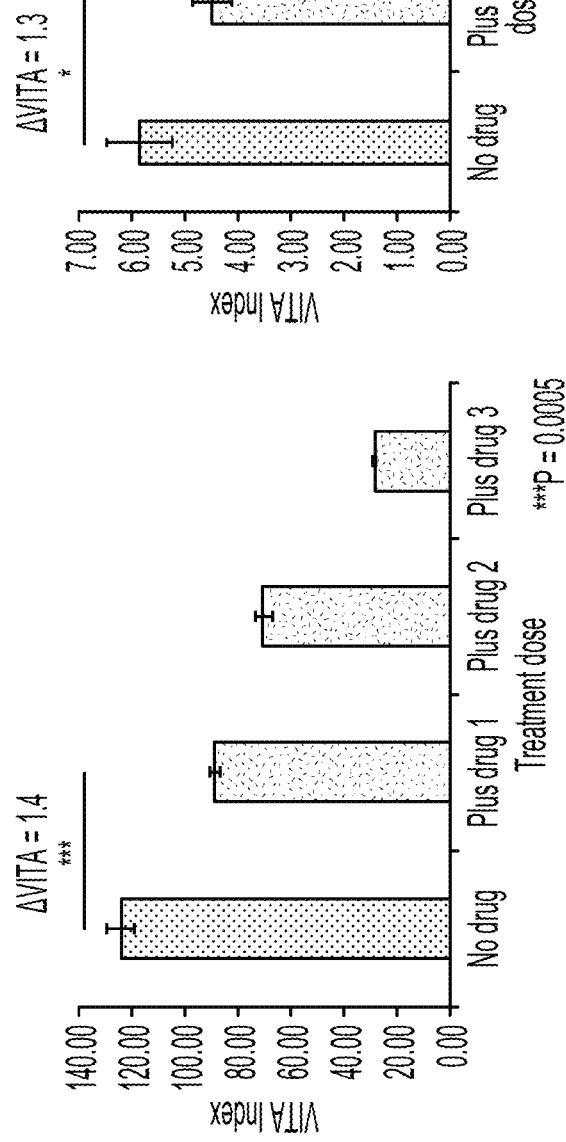
FIG. 8A
FIG. 8B
FIG. 8C

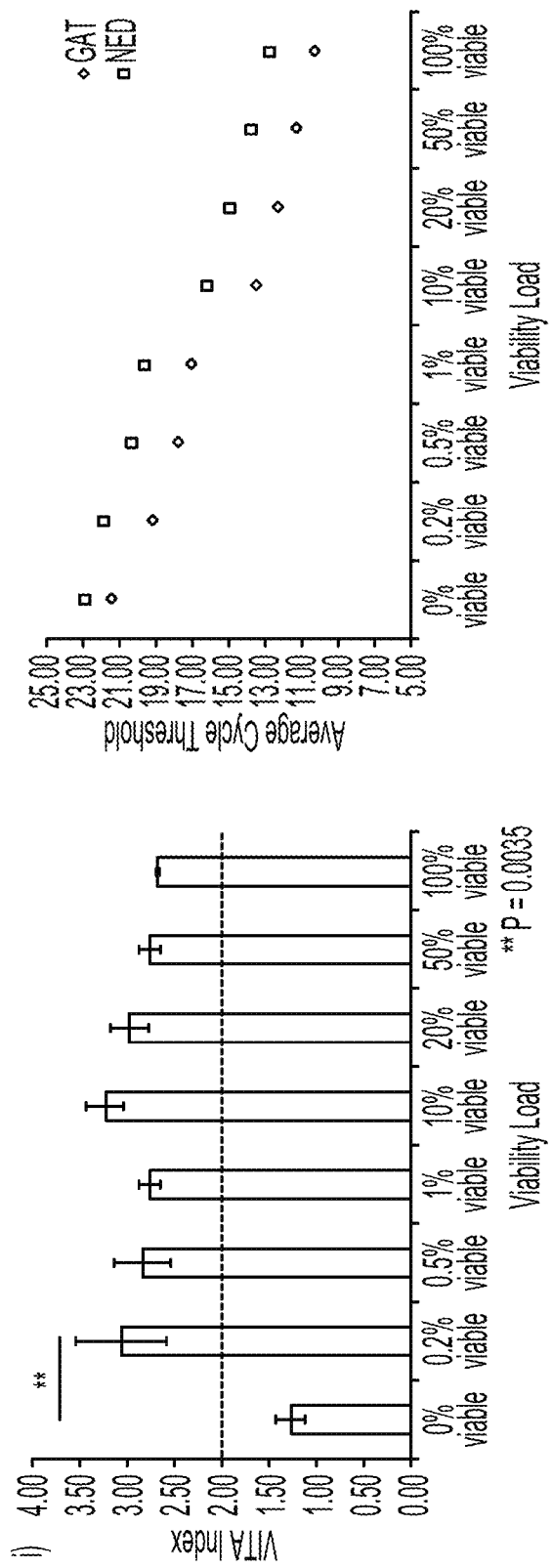
FIG. 11A
FIG. 11B
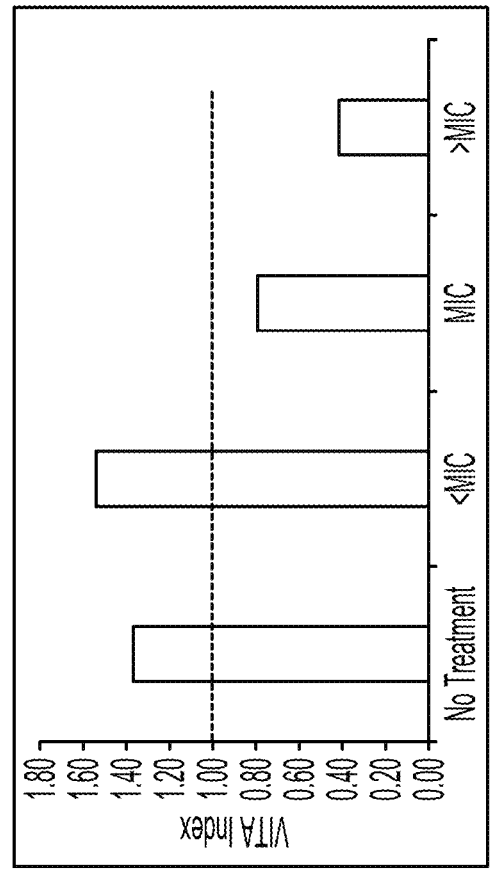
FIG. 12

NUCLEIC ACID RATIO DETERMINATION

INCORPORATION BY CROSS-REFERENCE

This application is a US national stage of PCT/AU2018/051406 filed on 21 Dec. 2018, which claims priority from Australian provisional patent application number 2017905138 filed on 21 Dec. 2017, the entire contents of which are incorporated herein by cross-reference.

REFERENCE TO SEQUENCE LISTING

This application includes an electronic sequence listing in a file named 541102SEQLST.TXT, created Apr. 30, 2020 and containing 9,265 bytes, which is hereby incorporated by reference.

TECHNICAL FIELD

The present invention relates generally to the field of molecular biology. More specifically, the present invention provides methods for quantitative data normalisation, and/or ascertaining levels of transcription in cells, organisms, viruses, and the like. The methods can be used in numerous applications including, but not limited to, determining transcriptional upregulation and downregulation, identifying transcriptional perturbation, determining viability/death, and assessing responses to treatment with agents (e.g. resistance or sensitivity to drugs).

BACKGROUND

Advancements in molecular biology have greatly improved the ability to characterize cells and interrogate their genomes and transcriptomes for evidence of changes associated with disease and/or external stimuli. For example, specific variations in sequence are found in association with acquired or inherited diseases, such as cancer or cystic fibrosis. Changes in expression of the gene are associated with both disease states and response to stimuli. Further, the presence of a foreign sequence can indicate the presence of infectious agents such as bacteria or viruses. Nucleic Acid Amplification Technology (NAAT) testing has broad application in all these fields for basic research, clinical research and clinical diagnostics.

Methods of in vitro nucleic acid amplification have widespread applications in NAAT testing. Such methods include polymerase chain reaction (PCR), strand displacement amplification (SDA), helicase-dependent amplification (HDA), Recombinase Polymerase Amplification (RPA), loop-mediated isothermal amplification (LAMP), rolling circle amplification (RCA), transcription-mediated amplification (TMA), self-sustained sequence replication (3SR), nucleic acid sequence based amplification (NASBA). Various types of PCR have been described including quantitative real time PCR, reverse transcription polymerase chain reaction (RT-PCR) and digital PCR. Each of these target amplification strategies requires the use of oligonucleotide primers. The process of amplification results in the exponential amplification of target sequences which incorporate the oligonucleotide primers at their 5' termini and which contain newly synthesized copies of the sequences located between the primers. Signal amplification techniques such as EzyAmp, Branched Chain Reaction or DoC can also be used for NAAT testing.

Normalization of gene expression (RNA levels) is a contentious topic, with various pros and cons existing for each of the strategies available. These include, normalization to sample size, to total RNA or ribosomal RNA, to mRNA of housekeeping genes and to genomic DNA. Normalization to mRNA of housekeeping genes requires judicious selection of targets as their stability and expression levels can be affected by experimental or environmental conditions. Further, in bacteria, expression levels can vary during the bacterial developmental cycle. Levels of ribosomal RNA (rRNA) although abundant and displaying longer half-lives, can also alter expression in response experimental or environmental conditions; and similarly levels in bacteria can change during the development cycle. Furthermore, with rRNA making up 80% of the total RNA fraction, there is a significant imbalance between rRNA and mRNA, the later comprising only 2-5%. Genomic DNA is thought to be a good candidate for gene expression normalization as it is always present, stable and it is generally invariable. Genomic DNA has been shown to generated more accurate and reproducible results.

There are, however, several limitations of using genomic DNA as a target for normalization of RNA levels. Most protocols do not simultaneously extract both RNA and DNA from a sample and hence these are extracted separately, quantified and subsequently amplified separately in parallel reactions which typically contain, or lack, reverse transcriptase respectively. As such there is a great deal of scope for error in comparing these two very different protocols and using the results from (i) a first protocol (DNA extraction and amplification by, for example, PCR) to normalize the results from (ii) a second protocol (RNA extraction and amplification by, for example, RT-PCR). Further, such parallel protocols are expensive, laborious and time consuming.

NAATs provide a gold standard for analysis of bacterial infections, due to their high sensitivity and specificity, fast turnaround time, ability to be performed on a variety of sample types, and their capacity to target any bacterial species. However, for some specific applications, current methods have disadvantages. In particular, they are not well suited to distinguishing between viable and dead pathogens. For example, bacterial DNA is not a good marker of cell viability because this DNA can survive for weeks after cell death has occurred. This fact sheds light on the limits of available assays, with uninformative use of quantification methods and inefficient monitoring of infection status or effectiveness of treatment. Potential overestimation of positivity may also occur.

The demand for more informative and accurate detection methods is imperative, especially when applied to sexually transmitted infections (STIs). New tools are urgently needed, particularly for cases where pathogens are present, but the patients are asymptomatic, and/or where pathogens have high rates of antimicrobial resistance (AMR). For such infections a test of cure (TOC) is required to confirm successful clearance. This confirmation of cure will reduce the potential for further complications, correlated with the initial infection, and will limit the prevalence and spread of pathogens and drug resistant strains. TOC methods are currently limited to NAAT assays, performed at a single time-point post treatment, and the optimal time can change depending on the species causing the STI. A positive result may infer treatment failure but could also reflect detection of non-viable DNA and/or RNA fragments.

Several techniques exist to tackle this issue. Methods for determining viability include metabolic monitoring through new culture methods, evaporation-induced stimulation of bacterial osmoregulation, antibiotic susceptibility testing (AST) such as Smarticles technology, bacteriophage-based detection and ratiometric pre-rRNA analysis. Although these have shown some success in differentiating viable and dead bacteria, all of the above still rely on culture procedures to attain a result. Alternate viability techniques steer away from culture methods. For example, some focus on intercalating dyes, applied prior to the DNA extraction process, for example ethidium monoazide (EMA) and propodium monoazide (PMA). The dyes bind to double stranded DNA, existing outside cells or following infiltration of dye through the broken walls of cells. This makes the DNA of dead bacteria resistant to subsequent PCR amplification. This approach has been widely applied on clinical samples, environmental and foodborne pathogen detection, however, the limitations are also evident and have been reviewed The dyes are not suitable for all types of samples or bacteria, with variability in both the incubation conditions and concentrations needed. It has been extensively shown that signal inhibition can arise from dye penetrating live cells and false-positive detection can occur as a consequence of a high non-viable bacterial load.

Detection of RNA is another method with potential for assessing cell viability since it is less stable than DNA and thus a truer reflection of viability. These methods, however, require further improvements since RNA transcripts have also been shown to persist for extended lengths of time, following treatment or cell death. This makes it vital to have judicious selection of appropriate transcripts & amplicon parameters along with the ability to fully eliminate contaminating DNA from RNA preparations. Thus, there is the need for more investigation into accurate RNA-based strategies to quantify viable bacteria.

A further area of need is for methods which allow screening for drug resistance or sensitivity. In particular, rapid antimicrobial susceptibility tests are urgently required for informing individual patient's therapy to prevent the spread of resistant pathogens. Further, such method could be used as screening methods for drug discovery programs. The invention described herein can generate more informative results, differentiating between the presence and absence of infectious agents, and in turn between uncleared and cleared infections. It involves an alternative approach of simultaneously analysing both RNA and DNA present in a single total nucleic acid (TNA) sample.

The invention described in this document has application in these areas and others. It provides a method for normalising the level of active transcription in a single reaction. Previous studies which have attempted to normalize RNA levels to DNA have shortcomings. In such studies researchers have extracted RNA and DNA from a specimen, amplified these in separate, parallel RT-PCR and PCR reactions and then normalized gene expression levels (RNA) to levels generated from DNA. There are many problems with this approach. Firstly, although the RNA & DNA may have originated from the same sample, they are processed differently to extract the two different species of nucleic acid (DNA versus RNA) and hence the efficiency of extraction is unlikely to be equal. Similarly, there can be sampling bias of these two extracted samples when aliquots are placed in separate tubes for analysis. Further, since they are amplified in different PCR reaction mixes, which differ in composition (e.g. at least by the presence or absence of reverse transcriptase) and often in thermocycling profiles, it is difficult to make meaningful comparisons. The following invention overcomes these limitations.

It is well known in the art that it is possible to simultaneously co-extract both DNA and RNA, which together are referred to as "total nucleic acid" (TNA). However, one aspect of an RT-PCR, which is not generally discussed in the literature, is that protocols which amplify a specific RNA transcript (RNA-X) in a TNA sample will also co-amplify the DNA (DNA-X) of the gene from which the specific target RNA-X was transcribed. The converse is also true in that, in a reverse transcriptase reaction, it is not possible to only amplify a specific DNA sequence (DNA-X), if that DNA is a gene or sequence which is actively transcribed, because the transcribed RNA (RNA-X) will also co-amplify. In other words, the amplification products of an RT-PCR from a TNA sample are always the sum of the amplicons derived from both RNA-X and DNA-X (RNA-X plus DNA-X), if DNA-X is transcribed to generate RNA-X. As such, it is not possible to normalize a specific unrelated RNA-Y with a genomic DNA-X sequence if that sequence is transcribed.

The present invention seeks to overcome one or more of the difficulties existing in the prior art by preparing nucleic acid samples comprising both DNA and RNA (e.g. TNA), and co-amplifying (i) one gene (DNA-X) and its associated RNA transcription products (RNA-X), along with an unrelated region of DNA (DNA-N) which is not transcribed. The DNA-N can then be used to normalize levels of the DNA-X plus RNA-X. Further, it is possible to use multiple primer sets targeting multiple transcribed genes or regions and their associated transcripts, for example DNA-X plus RNA-X and DNA-Y plus RNA-Y can be normalized to a non-transcribed DNA-N. Optionally, for convenience, the ratio obtained by dividing the data from analysis of multiple transcribed DNA/RNA targets by that from a single non-transcribed DNA-N can be again be divided by the number of primer sets targeting the sets of transcribed DNA/RNA species. The invention will be further clarified by way of the following examples.

SUMMARY OF THE INVENTION

The present invention may involve co-amplification of three nucleic acid species (e.g. simultaneously) in a sample comprising both DNA and RNA (e.g. of a sample of total nucleic acid (TNA)). These species are (i) gene(s), (ii) transcripts expressed from those gene(s), and (iii) non-expressed (i.e. non-transcribed) DNA sequences. Together the combined measurement of a gene and its corresponding transcripts is often referred to herein as GAT (Gene And Transcript) and the measurement of non-transcribed DNA is often referred to herein as NED (Non-Expressed DNA). The methods of the present invention involve co-amplifying these species together or separately, and using the ratio of the estimates of GAT and the NED as an indicator of transcriptional capacity, which can in turn be used to assess characteristics such as cell viability, cell death, functional perturbation of cells resulting from an external stimulus or a disease state, and the like.

The present invention relates, at least in part, to embodiments 1-48 listed below:

Embodiment 1. A method for normalising quantitative data obtained by amplification of nucleic acids from a cell, organism, or virus, the method comprising:

(i) obtaining quantitative data from amplification of genomic DNA from a first gene and RNA transcribed from the first gene, and from amplification of a sequence of non-transcribed DNA in the cell, organism, or virus; and (ii) using the quantitative data to derive a normalised value (nV) representative of the relative amounts of:
said genomic DNA and RNA transcripts of the first gene, to
said genomic DNA that is not transcribed, present within the nucleic acid sample prior said amplification.

Embodiment 2. The method of embodiment 1, wherein the quantitative data is amplicon copy number, and the method comprises:
obtaining a value A (vA) representing total amplicon number generated from the amplification of said genomic DNA and RNA transcripts of the first gene, and a value B (vB) representing total amplicon number generated from the sequence of non-transcribed DNA;
calculating a normalised value (nV) using the equation:

$$vA/vB = nV$$

or an equivalent form thereof.

Embodiment 3. The method of embodiment 1, wherein the quantitative data is amplicon copy number, and the method comprises:
obtaining a value X (vX) representing total amplicon number generated from: the amplification of genomic DNA and RNA transcripts from the first gene, and amplification of genomic DNA and RNA transcripts from at least one additional gene;
obtaining a value B (vB) representing total amplicon number generated from the sequence of non-transcribed DNA,
calculating a normalised value (nV) using the equation:

$$vX/(vB \times (X+1)) = nV$$

or an equivalent form thereof, wherein X is the number of said additional gene(s).

Embodiment 4. The method of embodiment 2 or embodiment 3, wherein the amplification is digital polymerase chain reaction (dPCR).

Embodiment 5. The method of embodiment 1, wherein the quantitative data is threshold value (Ct), and the method comprises:
obtaining a cycle threshold value CtA from the amplification of said genomic DNA and RNA transcripts of the first gene,
obtaining a cycle threshold value CtB from the amplification of the sequence of non-transcribed DNA; and
calculating a normalised value (nV) using the equation:

$$2^{CtB-ctA} = nV$$

or an equivalent form thereof.

Embodiment 6. The method of embodiment 1, wherein the quantitative data is threshold value (Ct), and the method comprises:
obtaining a cycle threshold value CtX from: the amplification of said genomic DNA and RNA transcripts of the first gene, and from amplification of genomic DNA and RNA transcripts from at least one additional gene;
obtaining a cycle threshold value CtB from the amplification of the sequence of non-transcribed DNA; and
calculating a normalised value (nV) using the equation:

$$2^{CtB-CtX}/(X+1) = nV$$

or an equivalent form thereof,
wherein X is the number of said additional gene(s).

Embodiment 7. The method of embodiment 5 or embodiment 6, wherein the amplification is quantitative polymerase chain reaction (qPCR).

Embodiment 8. The method of any one of embodiments 1 to 7, wherein the sequence of non-transcribed DNA is genomic DNA.

Embodiment 9. The method of any one of embodiments 1 to 8, further comprising conducting said amplification of the nucleic acids from the cell, organism, or virus.

Embodiment 10. The method of any one of embodiments 1 to 9, wherein the nucleic acids from the cell, organism, or virus are an extract of total nucleic acids.

Embodiment 11. The method of any one of embodiments 1 to 10, wherein any said amplification is conducted using: polymerase chain reaction (PCR), reverse transcription polymerase chain reaction (RT-PCR), strand displacement amplification (SDA), loop-mediated isothermal amplification (LAMP), rolling circle amplification (RCA), recombinase polymerase amplification (RPA), helicase dependent amplification (HDA), strand invasion based amplification (SIBA), transcript-mediated amplification (TMA), self-sustained sequence replication (3SR), nucleic acid sequence based amplification (NASBA), or any combination thereof.

Embodiment 12. The method of any one of embodiments 1 to 11, further comprising using the normalised value (nV) to assess the level of transcriptional activity in the cell, organism, or virus.

Embodiment 13. The method of any one of embodiments 1 to 12, further comprising:
obtaining a transcription-negative normalised value (nV−) generated using a series of said normalised values (nV) obtained from individuals of a population of the cells, organisms, or viruses known not to have transcriptional activity; and
comparing the normalised value (nV) obtained by said amplification of nucleic acids from the cell, organism, or virus to the transcription-negative normalised value (nV−), to thereby assess the level of transcriptional activity in the cell, organism, or virus.

Embodiment 14. The method of embodiment 13, wherein the transcription-negative normalised value (nV−) is a mean value generated from said series of said normalised values (nV).

Embodiment 15. The method of embodiment 13 or embodiment 14, wherein:
the transcription-negative normalised value (nV−) is used as a base value for assessing a presence or an absence of transcriptional activity in the cell, organism or virus; and
an absence of transcriptional activity is indicated when the normalised value (nV) obtained by said amplification of nucleic acids from the cell, organism, or virus is equal to or below the transcription-negative normalised value (nV−); or
transcriptional activity is indicated when the normalised value (nV) obtained by said amplification of nucleic acids from the cell, organism, or virus is above the transcription-negative normalised value (nV−).

Embodiment 16. The method of any one of embodiments 13 to 15, wherein said transcription-negative normalised value (nV−):
incorporates statistical variation in said series of normalised values (nV) from individuals of the population of the cells, organisms, or viruses known not to have transcriptional activity; and/or
is provided with a confidence interval that said transcription-negative normalised value (nV−) is predictive of a presence or an absence of transcriptional activity in the cell, organism or virus.

Embodiment 17. The method of embodiment 16, wherein the confidence interval is more than 90%, or more than 95%.

Embodiment 18. The method of any one of embodiments 13 to 17, further comprising:
  obtaining a transcription-positive normalised value (nV+) generated using a series of said normalised values (nV) obtained from individuals of a population of the cells, organisms, or viruses known to have transcriptional activity; and
  comparing the normalised value (nV) obtained by said amplification of nucleic acids from the cell, organism, or virus to the transcription-positive normalised value (nV+), to thereby assess the level of transcriptional activity in the cell, organism, or virus.

Embodiment 19. The method of embodiment 18, wherein the transcription-positive normalised value (nV+) is a mean value generated from said series of said normalised values (nV).

Embodiment 20. The method of embodiment 18 or embodiment 19, wherein:
  the transcription-positive normalised value (nV+) is used as a base value for transcriptional activity in the cell, organism or virus; and
  a lack or absence of transcriptional activity is indicated when the normalised value (nV) obtained by said amplification of nucleic acids from the cell, organism, or virus is below the transcription-positive normalised value (nV+); or
  transcriptional activity is indicated when the normalised value (nV) obtained by said amplification of nucleic acids from the cell, organism, or virus is equal to or above the transcription-positive normalised value (nV+).

Embodiment 21. The method of any one of embodiments 18 to 20, wherein said transcription-positive normalised value (nV+):
  incorporates statistical variation in said series of normalised values (nV) from individuals of the population of the cells, organisms, or viruses known to have transcriptional activity; and/or
  is provided with a confidence interval that said transcription-positive normalised value (nV+) is predictive of a presence or an absence of transcriptional activity in the cell, organism or virus.

Embodiment 22. The method of embodiment 21, wherein the confidence interval is more than 90%, or more than 95%.

Embodiment 23. The method of embodiment 13, further comprising:
  obtaining a transcription-negative normalised value (nV−) generated using a series of said normalised values (nV) obtained from individuals of a population of the cells, organisms, or viruses known not to have transcriptional activity;
  obtaining a transcription-positive normalised value (nV+) generated using a series of said normalised values (nV) obtained from individuals of a population of the cells, organisms, or viruses known to have transcriptional activity; and
  comparing the normalised value (nV) obtained by said amplification of nucleic acids from the cell, organism, or virus to:
    (i) the transcription-negative normalised value (nV−) and to the transcription-positive normalised value (nV+), or
    (ii) to a combined transcription normalised value (nV±) intermediate to the transcription-negative normalised value (nV−) and the transcription-positive normalised value (nV+),
  to thereby assess the level of transcriptional activity in the cell, organism, or virus.

Embodiment 24. The method of embodiment 23, wherein the combined transcription normalised value (nV±) is calculated using the equation:

$$(nV+)+(nV-)/2=(nV\pm)$$

or an equivalent form thereof.

Embodiment 25. The method of embodiment 24, wherein said combined transcription normalised value (nV+):
  incorporates statistical variation in said series of transcription-negative normalised value (nV−) and/or said transcription-positive normalised value (nV+); and/or
  is provided with a confidence interval that said combined transcription normalised value (nV±) is predictive of a presence or an absence of transcriptional activity in the cell, organism or virus.

Embodiment 26. The method of embodiment 25, wherein the confidence interval is more than 90%, or more than 95%.

Embodiment 27. The method of any one of embodiments 12 to 26, wherein the level of transcriptional activity in the cell, organism, or virus is assessed for the purpose of determining any one or more of:
  viability of the test cell or the test organism;
  whether the test cell, organism or virus is alive or dead;
  transcriptional perturbation within the test cell, organism, or virus.

Embodiment 28. The method of any one of embodiments 1 to 11, further comprising using the normalised value (nV) to assess the level of drug resistance or drug sensitivity in the cell, organism, or virus, wherein:
  said cell, organism, or virus has been treated with a drug prior to said amplification of nucleic acids, and
  said normalised value (nV) is compared to a control normalised value (cnV) generated using a series of said normalised values (nV) obtained from individuals of a population of the cells, organisms, or viruses known to be:
    (i) resistant to the drug; or
    (ii) sensitive to the drug,
  to thereby assess the level of drug resistance or drug sensitivity in the cell, organism, or virus.

Embodiment 29. The method of any one of embodiments 1 to 11 or 28, further comprising:
  obtaining a drug-sensitive normalised value (dsV) generated using a series of said normalised values (nV) obtained from individuals of a population of the cells, organisms, or viruses known to be sensitive to the drug; and
  comparing the normalised value (nV) obtained by said amplification of nucleic acids from the cell, organism, or virus to the drug-sensitive normalised value (dsV), to thereby assess the level of drug resistance or drug sensitivity or in the cell, organism, or virus, wherein the cell, organism, or virus has been treated with a drug prior to said amplification of nucleic acids.

Embodiment 30. The method of embodiment 29, wherein the drug-sensitive normalised value (dsV) is a mean value generated from said series of said normalised values (nV).

Embodiment 31. The method of embodiment 29 or embodiment 30, wherein:
  the drug-sensitive normalised value (dsV) is used as a base value for assessing a presence or an absence of resistance or sensitivity to the drug in the cell, organism or virus; and
  resistance to the drug is indicated when the normalised value (nV) obtained by said amplification of nucleic acids from the cell, organism, or virus is above the drug-sensitive normalised value (dsV); or
  sensitivity to the drug is indicated when the normalised value (nV) obtained by said amplification of nucleic acids from the cell, organism, or virus is equal to or below the drug-sensitive normalised value (dsV).

Embodiment 32. The method of any one of embodiments 29 to 31, wherein said drug-sensitive normalised value (dsV):
  incorporates statistical variation in said series of normalised values (nV) from individuals of the population of the cells, organisms, or viruses known to be sensitive to the drug; and/or
  is provided with a confidence interval that said drug-sensitive normalised value (dsV) is predictive of a presence or an absence of:
    (i) resistance to the drug in the cell, organism or virus; or
    (ii) sensitivity to the drug in the cell, organism or virus.

Embodiment 33. The method of embodiment 32, wherein the confidence interval is more than 90%, or more than 95%.

Embodiment 34. The method of any one of embodiments 1 to 11 or 28, further comprising:
  obtaining a drug-resistant normalised value (drV) generated using a series of said normalised values (nV) obtained from individuals of a population of the cells, organisms, or viruses known to resistant to the drug; and
  comparing the normalised value (nV) obtained by said amplification of nucleic acids from the cell, organism, or virus to the drug-resistant normalised value (drV), to thereby assess the level of drug resistance or drug sensitivity or in the cell, organism, or virus, wherein the cell, organism, or virus has been treated with a drug prior to said amplification of nucleic acids.

Embodiment 35. The method of embodiment 34, wherein the drug-resistant normalised value (drV) is a mean value generated from said series of said normalised values (nV).

Embodiment 36. The method of embodiment 34 or embodiment 35, wherein:
  the drug-resistant normalised value (drV) is used as a base value for assessing a presence or an absence of resistance or sensitivity to the drug in the cell, organism or virus; and
  resistance to the drug is indicated when the normalised value (nV) obtained by said amplification of nucleic acids from the cell, organism, or virus is equal to or above the drug-resistant normalised value (drV); or
  sensitivity to the drug is indicated when the normalised value (nV) obtained by said amplification of nucleic acids from the cell, organism, or virus is below the drug-resistant normalised value (drV).

Embodiment 37. The method of any one of embodiments 34 to 36, wherein said drug-resistant normalised value (drV):
  incorporates statistical variation in said series of normalised values (nV) from individuals of the population of the cells, organisms, or viruses known to be resistant to the drug; and/or
  is provided with a confidence interval that said drug-resistant normalised value (drV) is predictive of a presence or an absence of:
    (i) resistance to the drug in the cell, organism or virus; or
    (ii) sensitivity to the drug in the cell, organism or virus.

Embodiment 38. The method of embodiment 37, wherein the confidence interval is more than 90%, or more than 95%.

Embodiment 39. The method of one of embodiments 1 to 11, further comprising using the normalised value (nV) to assess the level of drug resistance or drug sensitivity in the cell, organism, or virus, wherein:
  a first population of said cell, organism, or virus which has been treated with a drug prior to said amplification of nucleic acids, is used to generate a first said normalized value (nV),
  a second population of said cell, organism, or virus which has not been treated with a drug prior to said amplification of nucleic acids, is used to generate a second said normalized value (nV),
  said first normalized value (nV) and said second normalized value (nV) are compared to assess the level of transcriptional activity in the cell, organism, or virus with or without drug treatment, and thereby assess the level of drug resistance or drug sensitivity in the cell, organism, or virus.

Embodiment 40. The method of embodiment 39, wherein said drug sensitivity is indicated when said first normalized value (nV) is lower than said second normalized value (nV).

Embodiment 41. The method of any one of embodiments 27 to 40, wherein the drug is an antimicrobial.

Embodiment 42. The method of any one of embodiments 27 to 41, wherein the drug is an antimicrobial of a class selected from: Aminoglycosides, ansamycins, carbacephem, carbapenems, cephalosporins, glycopeptides, macrolidespenicillins, monobactams, polypeptides, quinolones, sulphonamides, tetracyclines.

Embodiment 43. The method of any one of embodiments 27 to 42, wherein the drug is Ciprofloxacin, Azithromycin, Rifampicin, or Doxycycline.

Embodiment 44. The method of any one of embodiments 27 to 43, wherein the first gene is a gene from a *Chlamydia* species (e.g. *Chlamydia trachomatis*), a Gonorrhea species, or a *mycoplasma* species (e.g. *Mycoplasma genitralium*).

Embodiment 45. The method of any one of embodiments 1 to 44, wherein said genomic DNA from the first gene and RNA transcribed from the first gene, and said sequence of non-transcribed DNA are co-amplified in the same reaction.

Embodiment 46. The method of embodiment 45, wherein said reaction comprises using reverse transcriptase.

Embodiment 47. The method of any one of embodiments 1 to 46, wherein the cell is a mammalian cell, a human cell, an animal cell, a plant cell, a bacterial cell, a host cell infected by viruses, or a host cell of infected by bacteria.

Embodiment 48. The method of any one of embodiments 1 to 47, wherein the organism is a mammal, a human, a plant, a bacterium, a virus, a fungus, an alga, an archaeon or a protozoan.

The present invention also relates, at least in part, to embodiments 1-23 listed below:

Embodiment 1. A method for assessing the transcriptional activity of a cell or an organism, the method comprising:
  performing a nucleic acid amplification reaction on total nucleic acid from the cell or organism, wherein the nucleic acid amplification comprises:

contacting the total nucleic acid sample with one or multiple primers capable of amplifying genomic DNA from a first gene and RNA transcribed from the first gene, contacting the total nucleic acid sample with one or multiple primers capable of amplifying a region of non-coding genomic DNA that is not transcribed in the cell or organism;

analysing kinetics of the nucleic acid amplification reaction to derive a ratio of:

(i) said genomic DNA and RNA transcripts of the first gene, to (ii) said region of non-coding DNA, wherein the ratio is representative of the relative amount of (i) and (ii) present within the total nucleic acid sample prior to performing the nucleic acid amplification reaction; and analysing the ratio to assess the transcriptional activity of the cell or organism, wherein:

a ratio of 1 indicates an absence of transcriptional activity in the cell or organism, and a ratio of more than 1 indicates that transcriptional activity exists or may exist in the cell or organism.

Embodiment 2. The method of embodiment 1, wherein a ratio of more than: 1.5, 1.7, 1.9, 2, 2.2, 2.4, 2.5, 2.7, 2.9 or 3, indicates transcriptional activity in the cell or organism.

Embodiment 3. The method of embodiment 1, wherein a ratio of less than: 1.5, 1.4, 1.3, 1.2 or 1.1 indicates an absence of transcriptional activity in the cell or organism.

Embodiment 4. A method for assessing the viability of a cell or an organism, the method comprising:

performing a nucleic acid amplification reaction on total nucleic acid the cell or organism, wherein the nucleic acid amplification comprises:

contacting the total nucleic acid sample with one or multiple primers capable of amplifying genomic DNA from a first gene and RNA transcribed from the first gene, contacting the total nucleic acid sample with one or multiple primers capable of amplifying a region of non-coding genomic DNA that is not transcribed in the cell or organism;

analysing kinetics of the nucleic acid amplification reaction to derive a ratio of:

(i) said genomic DNA and RNA transcripts of the first gene, to (ii) said region of non-coding DNA, wherein the ratio is representative of the relative amount of (i) and (ii) present within the total nucleic acid sample prior to performing the nucleic acid amplification reaction; and analysing the ratio to assess the transcriptional activity of the cell or organism, wherein:

a ratio of 1 indicates the cell or organism is not viable, and a ratio of more than 1 indicates that the cell or organism is or may be viable.

Embodiment 5. The method of embodiment 4, wherein a ratio of more than: 1.5, 1.7, 1.9, 2, 2.2, 2.4, 2.5, 2.7, 2.9 or 3, indicates that the cell or organism is viable.

Embodiment 6. The method of embodiment 4, wherein a ratio of less than: 1.5, 1.4, 1.3, 1.2 or 1.1 indicates that the cell or organism is not viable.

Embodiment 7. A method for determining whether a cell or an organism is dead, the method comprising:

performing a nucleic acid amplification reaction on total nucleic acid from the cell or organism, wherein the nucleic acid amplification comprises:

contacting the total nucleic acid sample with one or multiple primers capable of amplifying genomic DNA from a first gene and RNA transcribed from the first gene, contacting the total nucleic acid sample with one or multiple primers capable of amplifying a region of non-coding genomic DNA that is not transcribed in the cell or organism;

analysing kinetics of the nucleic acid amplification reaction to derive a ratio of:

(i) said genomic DNA and RNA transcripts of the first gene, to (ii) said region of non-coding DNA, wherein the ratio is representative of the relative amount of (i) and (ii) present within the total nucleic acid sample prior to performing the nucleic acid amplification reaction; and analysing the ratio to assess the transcriptional activity of the cell or organism, wherein:

a ratio of 1 indicates that the cell or organism is dead, and a ratio of more than 1 indicates that the cell or organism is alive or may be alive.

Embodiment 8. The method of embodiment 7, wherein a ratio of more than: 1.5, 1.7, 1.9, 2, 2.2, 2.4, 2.5, 2.7, 2.9 or 3, indicates that the cell or organism is alive.

Embodiment 9. The method of embodiment 7, wherein a ratio of less than: 1.5, 1.4, 1.3, 1.2 or 1.1 indicates that the cell or organism is not alive.

Embodiment 10. A method for detecting transcriptional perturbation within a cell, the method comprising:

performing a nucleic acid amplification reaction on total nucleic acid from the cell or organism, wherein the nucleic acid amplification comprises:

contacting the total nucleic acid sample with one or multiple primers capable of amplifying genomic DNA from a first gene and RNA transcribed from the first gene, contacting the total nucleic acid sample with one or multiple primers capable of amplifying a region of non-coding genomic DNA that is not transcribed in the cell or organism;

analysing kinetics of the nucleic acid amplification reaction to derive a ratio of:

(i) said genomic DNA and RNA transcripts of the first gene, to (ii) said region of non-coding DNA, wherein the ratio is representative of the relative amount of (i) and (ii) present within the total nucleic acid sample prior to performing the nucleic acid amplification reaction; and analysing the ratio to assess the transcriptional activity of the cell or organism, wherein:

a ratio of 1 indicates complete transcriptional perturbation in the cell or organism, and a ratio of more than 1 indicates a lack of transcriptional perturbation in the cell or organism.

Embodiment 11. The method of embodiment 10, wherein a ratio of more than: 1.5, 1.7, 1.9, 2, 2.2, 2.4, 2.5, 2.7, 2.9 or 3, indicates a lack of transcriptional perturbation in the cell or organism.

Embodiment 12. The method of embodiment 10, wherein a ratio of less than: 1.5, 1.4, 1.3, 1.2 or 1.1 indicates partial or complete transcriptional perturbation in the cell or organism.

Embodiment 13. The method of any one of embodiments 1 to 12, comprising generating and a cycle threshold (Ct) value for:
(i) said region of non-coding DNA, and
(ii) said genomic DNA and RNA transcripts of the first gene;
during said nucleic acid amplification reaction and deriving the ratio by comparing said values.

Embodiment 14. The method of any one of embodiments 1 to 13, wherein the method comprises:
generating a cycle threshold value ctA for said genomic DNA and RNA transcripts of the first gene, and, generating a cycle threshold value CtB for said region of non-coding DNA, following commencement of the nucleic acid amplification reaction;
calculating a fold change between the CtB and ctA values using the equation:

$$2^{CtB-CtA} = 2^{\Delta Ct}; \text{ and}$$

generating the ratio using the equation:

$$2^{\Delta Ct}/TR$$

wherein TR is a ratio of copies of the genomic DNA of the first gene to copies of the region of non-coding genomic DNA in the total nucleic acid sample of the cell.

Embodiment 15. The method of any one of embodiments 1 to 14, wherein:
performing the nucleic acid amplification reaction further comprises contacting the total nucleic acid sample with one or multiple primers capable of amplifying genomic DNA from a second gene and RNA transcribed from the second gene, and
the kinetics of the nucleic acid amplification reaction are analysed to derive a ratio representative of the relative amount of
(i) said region of non-coding DNA, to
(ii) said genomic DNA and RNA transcripts of the first and second genes present within the total nucleic acid sample prior to performing the nucleic acid amplification reaction.

Embodiment 16. The method of embodiment 15, wherein the method comprises:
generating a cycle threshold value ctA for said genomic DNA and RNA transcripts of the first and second genes, and, generating a cycle threshold value CtB for said region of non-coding DNA, following commencement of the nucleic acid amplification reaction;
calculating a fold change between the CtB and ctA values using the equation:

$$2^{CtB-CtA} = 2^{\Delta Ct}$$

generating the ratio using the equation $$2^{\Delta Ct}/TR$$

wherein TR is a ratio of copies of the genomic DNA of the first and second genes to copies of the region of non-coding genomic DNA in the total nucleic acid sample of the cell.

Embodiment 17. The method of any one of embodiments 1 to 16, wherein said analysing the ratio comprises comparing the ratio to a threshold ratio derived from performing the method on a series of negative or positive control cells or organisms and deriving a mean threshold ratio value indicative of a phenotype.

Embodiment 18. A method for detecting drug resistance or drug sensitivity in a cell or organism, the method comprising:
performing a first nucleic acid amplification reaction on total nucleic acids obtained from a first sample of the cell or organism that has not been treated with the drug; and
performing a second nucleic acid amplification reaction on total nucleic acids obtained from a second sample of the cell or organism that has been treated with the drug;
wherein each said nucleic acid amplification reaction is performed separately and comprises:
contacting the total nucleic acid sample with one or multiple primers capable of amplifying genomic DNA from a first gene and RNA transcribed from the first gene,
contacting the total nucleic acid sample with one or multiple primers capable of amplifying a region of non-coding genomic DNA that is not transcribed in the cell or organism;
analysing kinetics of each said nucleic acid amplification reaction to derive first and second ratios of
(i) said genomic DNA and RNA transcripts of the first gene, to
(ii) said region of non-coding DNA,
wherein the ratio is representative of the relative amount of (i) and (ii) present in the total nucleic acid sample prior to performing the nucleic acid amplification reaction; and
comparing the ratios to assess whether the cell or organism has resistance to the drug, wherein:
complete drug resistance in the cell or organism is indicated when the first and second ratios are equal, and
sensitivity of the cell or organism to the drug is indicated when the second ratio is lower than the first ratio.

Embodiment 19. The method of embodiment 18, wherein the cell or organism is deemed to have resistance to the drug when the value of second ratio is no more than: 1%, 2%, 5%, 7.5%, 10%, 12%, 15% or 20%; lower than the value of first ratio.

Embodiment 20. The method of embodiment 18, wherein the cell or organism is deemed to be sensitive to the drug when the value of second ratio is at least: 10%, 20%, 30%, 40% or 50%; than the first ratio.

Embodiment 21. The method of any one of embodiments 1 to 20, wherein the amplification method is selected from the group consisting of: polymerase chain reaction (PCR), strand displacement amplification (SDA), helicase dependent amplification (HDA), Recombinase Polymerase Amplification (RPA), loop-mediated isothermal amplification (LAMP), rolling circle amplification (RCA), transcription-mediated amplification (TMA), self-sustained sequence replication (3SR), nucleic acid sequence based amplification (NASBA), reverse transcription polymerase chain reaction (RT-PCR), and any combination thereof.

Embodiment 22. The method of any one of embodiments 1 to 21, wherein the cell is a mammalian cell, a human cell, a plant cell, a bacterial cell, a host cell infected by viruses, or a host cell of infected by bacteria.

Embodiment 23. The method of any one of embodiments 1 to 21, wherein the organism is a bacterium, a virus, a fungi, an algae, an archaeon or a protozoan.

The present invention is generally compatible with current procedures used in research or diagnostic laboratories and can use the same sample types, extraction methods and amplification methods. The nucleic acids (e.g. TNA) to be analysed may be a derived from any suitable source such as, for example, prokaryotic or eukaryotic cells, or from a virus. The present invention can determine the presence or absence of active transcription, an increase or decrease in RNA expression levels or unchanged RNA expression levels.

BRIEF DESCRIPTION OF THE DRAWINGS

Embodiments of the present invention will now be described, by way of non-limiting example only, with reference to the accompanying FIGS. 1-12 as set out below.

FIG. 2A: The methods described herein can be used to determine if cells or pathogens are dead or alive. Evidence of the presence of dead or alive pathogens could in turn provide a method for Test of Cure (TOC). The protocol involves performing VITA PCR amplifying GAT and NED from TNA and then using the resultant Ct values to calculate the VITA Index of the sample. Hypothetical amplification plots are depicted. A sample with no active transcription (dead cells) would be anticipated to have a VITA Index at or near 1. A threshold value can be set using empirical data for specific VITA PCR assays, amplifying specific GAT(s) and NED combinations, present within specific cell types and/or specific pathogens. Cells which are alive and are undergoing active transcription will have a VITA Index above the threshold. FIG. 2B: The methods described herein can be used to determine drug sensitivity or drug resistance. A sample can be split and incubated in the presence or absence of one or more drugs. TNA extracted after incubation can be analysed by VITA PCR to obtain VITA Indices for the treated and untreated sample and the ratio between the VITA Indices gives an indication of drug sensitivity or resistance. Hypothetical amplification plots are depicted. If the sample were sensitive to the drug, the VITA Indices of the sample in the presence of drug would be expected to be lower than in the absence of drug. In contrast, if the sample were resistant to the drug, the VITA Index of the sample in the presence of drug would not be expected to be lower than in the absence of drug and may be similar.

FIGS. 3A-C: Immunofluorescent staining of cells and analysis by PCR. *Chlamydia trachomatis* (serovar D) samples, grown in HEp-2 cells were treated with different concentrations of Azithromycin as described in Example 1, Treatment Protocol A (1.2.1). Specifically, cells were treated with i) No antibiotic, or ii) below the MIC (<MIC, 0.008 μg/mL), iii) at the MIC (0.064 μg/mL) or iv) above the MIC (>MIC 0.512 μg/mL). FIG. 3A shows representative images for the determination of viability of untreated cells and cells treated at each antibiotic dose. These images were obtained through immunofluorescence staining of infected HEp-2 cells and analysed at 100× magnification with a fluorescent microscope IN Cell Analyser 2200 (GE Healthcare Life Sciences). FIG. 3B shows the quantified viability post-infection (PI) measured as the Inclusion Forming Units per mL (IFU/mL) for each antibiotic dose treatment, at concentrations below (<MIC), equal to (MIC) or above the MIC (>MIC), and for untreated cells (No Antibiotic), calculated from the images obtained in panel i. Results were normalised against the value obtained for the sample treated at an antibiotic concentration above the MIC. FIG. 3C shows analysis of TNA from these cells, which were infected with *chlamydia*, and amplified by one set of primer capable of amplifying both Major outer membrane porin (omp1) DNA and omp1 RNA The TNA was amplified by RT-PCR (to amplify omp1 DNA and RNA) and by PCR (to only amplify omp1 DNA). Panel iii depicts the fold change, being the difference (ΔCt) between the Ct of omp1 DNA in PCR and the Ct of omp1 RNA plus omp1 DNA in the RT-PCR, calculated as $2^{\Delta Ct}$ for each antibiotic treatment dose, at concentrations below (<MIC), equal to (MIC) or above the MIC (>MIC), and untreated cells (No Antibiotic).

FIGS. 4A-D: Analysis of assays according to embodiments of the present invention. Analysis of candidate GAT and NED targets by amplification of RNA or TNA samples, and comparison between results for PCR (to amplify DNA only) and RT-PCR (to amplify DNA and RNA). FIGS. 4A and 4B show amplification plots generated using potential GAT primers (omp1), where the template was RNA only (FIG. 4A) or TNA (FIG. 4B). The difference (ΔCt) between Ct of omp1 DNA detection only by PCR (dotted lines), and omp1 DNA plus omp1 RNA detection by RT-PCR, (solid lines) is indicated.

FIGS. 4C and D show amplification plots using potential NED primers (InfAIGR), where the template was RNA only (FIG. 4C) or TNA (FIG. 4D). The differences (ΔCt) between Ct of InfAIGR DNA detection only by PCR (dotted lines), and InfAIGR DNA plus InfAIGR 1 RNA (if present) detection by RT-PCR, (solid lines) is indicated.

FIG. 5A shows the VITA indices for untreated cells (No Antibiotic) and for each antibiotic treatment dose as described in Example 1 and depicted in FIG. 3 panels i and ii. This VITA PCR amplified from TNA and used one gene and its transcripts to measure GAT and one non-transcribed DNA region to measure NED in the single RT-PCR reaction. FIG. 5A shows the RT-PCR data from the samples imaged, quantified in and depicted in FIGS. 3A and B respectively. FIG. 5B shows analysis of *chlamydia* by VITA PCR. The VITA indices for untreated cells (No Antibiotic) and for each antibiotic treatment dose. This VITA PCR amplified two amplicons of a gene and its transcripts (2 GAT) and one non-transcribed NED in the same RT-PCR and hence has a TR is 2 (2 GAT divided by 1 NED).

FIG. 6A schematically depicts the process of sample preparation. FIG. 6B shows analysis of *chlamydia* expression from patient urine sample in comparison to positive (viable) and negative (non-viable) *chlamydia* reference samples obtained through culture methods.

FIGS. 7A-E: Assays and analysis according to embodiments of the present invention. Analysis of *chlamydia* expression by VITA PCR in response to short incubations with antibiotics. FIG. 7A schematically depicts the process of sample preparation, wherein a test sample is either untreated (No drug) or treated with various antibiotics (Plus drug) and then incubated for various time intervals at either room temperature, or at 37° C. with 5% $CO_2$. TNA is then extracted from all samples and time points and amplified by VITA PCR. FIG. 7B shows the VITA Indices obtained by analysis of TNA for each treatment group either with (dark grey) and without (light grey) azithromycin. The ratios of the VITA Indices (ΔVITA) plus and minus azithromycin are indicated above the bars. The VITA Indices were significantly lower following incubation with the drug at 37° C. for either 1 hour or 6 hours indicating the samples were sensitive to azithromycin and this resulted in decreased transcription levels. The magnitude of the ΔVITA Ratio may reflect the extent of killing following incubation for specific times and under specific conditions. FIG. 7C shows the VITA Indices obtained by analysis of TNA for each treatment group with the ratio of the VITA Indices (ΔVITA) indicated above the bars. The decrease in the VITA Index following treatment with 0.128 µg/mL of azithromycin at 37° C. for 30 minutes and 1 hour indicated the samples were sensitive to this antibiotic and this was reflected as decreased transcription levels. FIG. 7D shows the VITA Indices obtained by analysis of TNA for each treatment group of susceptible and resistant strain, when treated with 0.256 µg/mL of rifampicin. The decrease in the VITA Index following antibiotic treatment for the susceptible strain after 5 minutes of incubation at 37° C. supply indicated the samples were sensitive to the antibiotic. Alongside this, the VITA Index for the resistant strain under the same conditions did not change significantly in the presence rifampicin at either time point indicated the samples were indeed resistant to the antibiotic FIG. 7E shows the VITA Indices obtained by analysis of TNA for each treatment group for strain known to be susceptible and resistant, when treated with 0.256 µg/mL of rifampicin for 15 minutes at room temperature. The VITA Indices of the susceptible strain showed a significant decrease in VITA Index in the presence of drug, consistent with sensitivity to Rifampicin; whilst the VITA Index for the resistant strain, under the same conditions, displayed a significant increase in VITA Index, reflecting resistance to rifampicin.

FIGS. 8A-C: Assays and analysis according to embodiments of the present invention. Analysis of *chlamydia* by VITA PCR in response to increasing doses of antibiotic. FIG. 8A schematically depicts the process of sample preparation, treatment without and with various concentrations of the same antibiotic (azithromycin), incubation for 1 hour at 37° C. with 5% $CO_2$ supply, extraction of TNA from untreated samples and samples treated with the various antibiotic concentrations. FIG. 8B displays the VITA Indices obtained by analysis of TNA for each dose of antibiotic and extracted using phenol:chloroform:isoamyl. Statistical differences between treated and untreated samples are represented above the compared to groups. The decrease in the VITA Index following antibiotic treatment indicated samples were sensitive to the antibiotic used. The VITA Indices displayed a decrease with increasing concentration of azithromycin (0.128 µg/mL, 0.192 µg/mL and 0.256 µg/mL respectively), with this correlation producing an $R^2$=0.98. FIG. 8C exhibits the VITA Indices obtained by analysis of TNA for each dose of antibiotic and extracted using a column-based extraction kit. Statistical differences between treated and untreated samples are indicated above the treatment groups. The decrease in the VITA Index following antibiotic treatment demonstrated samples were sensitive to azithromycin and VITA Indices correlated to the doses of antibiotic used 0.128 µg/mL, 0.192 µg/mL, 0.256 µg/mL and 0.512 µg/mL respectively, producing an $R^2$=0.83.

FIG. 9A depicts the VITA Indices obtained for each strain tested (strains 1-3 and 5) following analysis of TNA by VITA PCR for each treatment group. The decrease in VITA Index following treatment with azithromycin (0.256 µg/mL) indicated all strains were susceptible to the antibiotic with disruption caused to transcription. Statistical differences between treated and untreated samples are displayed above the compared samples. FIG. 9B illustrates the VITA Indices obtained for each strain tested (strains 1-3 and 5) following analysis of TNA for each treatment group. The decrease in VITA Index following treatment with doxycycline (0.256 µg/mL) indicated all strains were susceptible to the antibiotic with transcription activity disrupted. Statistical differences between treated and untreated samples are displayed above the compared samples. FIG. 9C shows the VITA Indices obtained for each strain tested (strain 1-5) following analysis of TNA for each treatment group, using the antibiotic rifampicin (0.256 µg/mL). The decrease in VITA Index following treatment indicated strains 1-4 are susceptible to the antibiotic with transcription activity disrupted. Statistical differences between the treated and untreated samples is displayed above the compared groups. The VITA Indices obtained with strain 5, in both untreated and treated sample, were not significantly different and reflected the resistance of this particular strain to Rifampicin. FIG. 9D demonstrates the ΔVITA ratio calculated from each replicate tested for each strain which was treated with Rifampicin depicted in FIG. 9C. Cells were grouped according to their susceptibility profile, with susceptible cells generating a greater ΔVITA ratio compared to resistant cells.

FIGS. 11A-B: Analysis of assays according to embodiments of the present invention. VITA PCR Analysis of *chlamydia* TNA samples containing different viable loads of the organism. FIG. 11A illustrates the VITA Index obtained from each sample containing a determined percentage of viable *chlamydia* in the background of non-viable *chlamydia*. Displaying statistical differences between non-viable sample and viable samples. FIG. 11B depicts the average Ct value for GAT1/2 and NED in each of the samples tested.

FIG. 12: Analysis of assays according to embodiments of the present invention. Analysis of *chlamydia* in TNA samples by an alternative VITA PCR system which targets longer regions for GAT1 and GAT 2. It displays the VITA Indices for untreated cells (No Treatment) and for each antibiotic treatment dose as per Example 1 and FIGS. 3A-B. This VITA PCR amplified two long amplicons of a gene and its transcripts (2 GAT) and one non-transcribed NED in the same reaction and hence has a TR of 2.

DEFINITIONS

Figure 1:
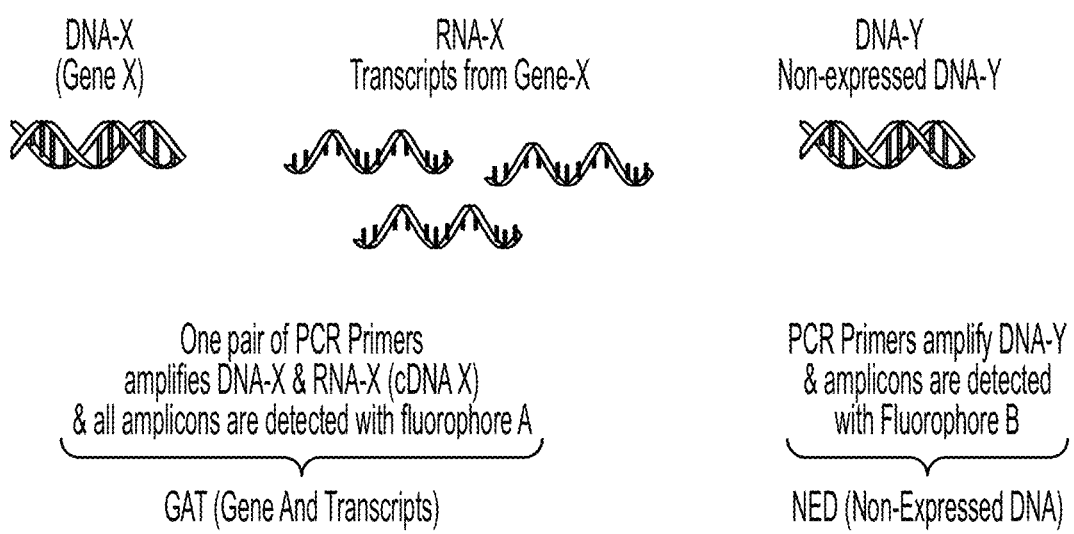
FIG. 1: Schematic showing steps in VITA PCR. A Reverse Transcriptase PCR (RT-PCR) is performed using total nucleic acid as template. This VITA PCR assay has at least one set of primers which is capable of co-amplifying the DNA of a specific gene (DNA-X) together with the RNA transcribed from this gene (RNA-X). It also contains a set of primers targeting a region of DNA which is not transcribed into RNA (DNA-N). During the reverse transcriptase step the RNA-X is copied into cDNA-X and then during PCR thermocycling DNA-X, cDNA-X and DNA-N are all amplified. The signal from the GAT (Gene And Transcript), which measures the sum of amplicons originating from DNA-X plus RNA-X can be read through a single Fluorophore Channel A, whilst the signal from the NED (Non-Expressed DNA), which is a measure of amplicons from DNA-N, can be read through a second Fluorophore Channel B. The difference in Cycle threshold (Ct) values between GAT and NED in a specimen allows an estimate of the fold change (FC) in a specimen observed for these targets, wherein $FC=2^{Ct\ NED-Ct\ GAT}=2^{\Delta Ct}$. The VITA Index can be calculated by dividing the fold change observed in the sample by the theoretical ratio (TR) anticipated in the absence of active transcription, assuming the gene and NED locus are present in equal copy numbers. If one transcript & gene are used to measure the GAT and one DNA sequence is used to measure NED, then the TR=(1×DNA-X) divided by (1×DNA-Y)=1. If two transcripts & genes (X and Z) are used to measure the GAT and one DNA sequence (X) is used to measure NED, then the TR=(1×DNA-X+1×DNA-Z) divided by (1×DNA-Y)=2. The ability to measure GAT using more than one gene(s) and its transcripts allows tests to be built which capture a range of transcripts which may be expressed at various times within the cell cycle. The VITA Index provides a normalized measure of transcriptional activity which can be compared between samples regardless of the amount of sample analysed. Cells which are dead and have no residual RNA detected would be anticipated to have a VITA Index close to 1; and as the level of active transcription increases, the VITA Index will increase correspondingly.
Figure 2A:
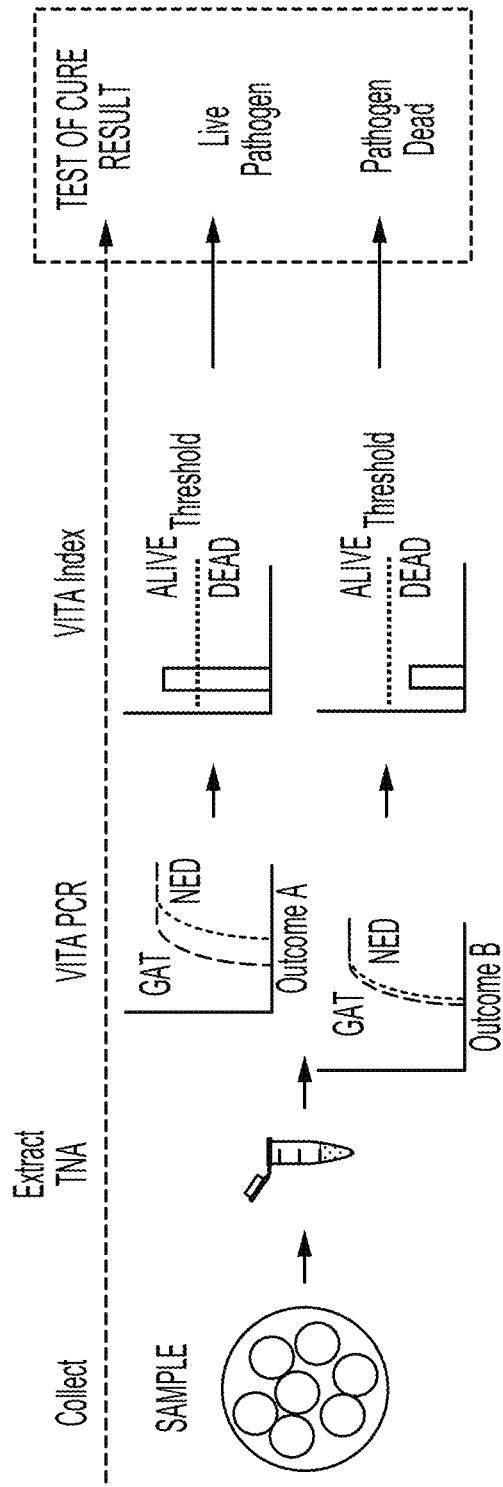
FIGS. 2A, B: Schematics of assays according to embodiments of the present invention.
Figure 2B:
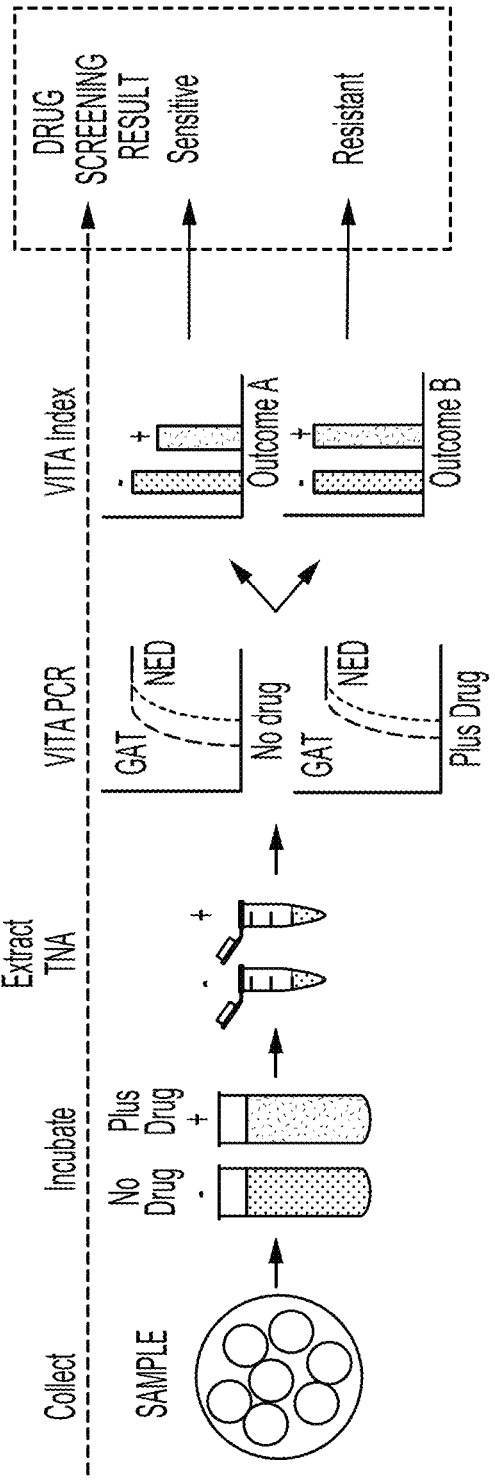
Figures 4A, 4B:
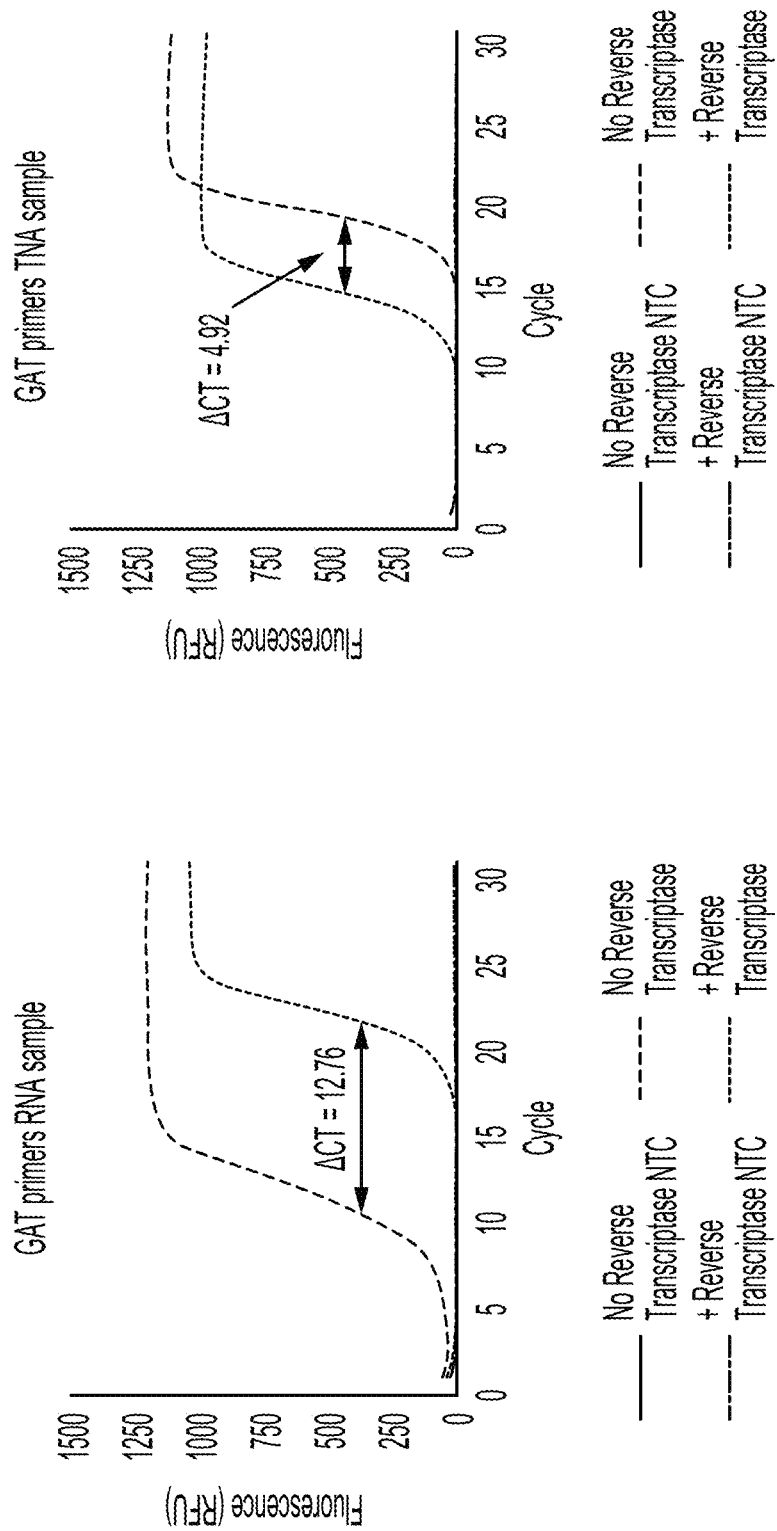

As used in this application, the singular form "a", "an" and "the" include plural references unless the context clearly dictates otherwise. For example, the phrase "polynucleotide" also includes a plurality of polynucleotides.

As used herein, the term "comprising" means "including". Variations of the word "comprising", such as "comprise" and "comprises," have correspondingly varied meanings. Thus, for example, a polynucleotide "comprising" a sequence of nucleotides may consist exclusively of that sequence of nucleotides or may include one or more additional nucleotides.

As used herein, the terms "cycle threshold", "cycle threshold value", "threshold cycle", "threshold cycle value", "Ct" and "Ct value" are used interchangeably and have the same meaning, being the number of amplification cycles required to generate a detectable amount of amplicon during a nucleic acid amplification reaction.

As used herein, the term "amplification" when used in the context of nucleic acids will be understood to encompass any reaction capable of generating copies of one more more nucleic acid template sequence(s), unless clearly indicated otherwise. Non-limiting examples of suitable reactios include polymerase chain reaction (PCR), strand displacement amplification (SDA), helicase-dependent amplification (HDA), Recombinase Polymerase Amplification (RPA), loop-mediated isothermal amplification (LAMP), rolling circle amplification (RCA), transcription-mediated amplification (TMA), self-sustained sequence replication (3SR), and nucleic acid sequence based amplification (NASBA).

As used herein, the term "quantitative value" is intended to encompass any measurement of a given factor by quantity including, for example, quantitative measurements of amplification reaction products (e.g. by Ct value, by amplicon copy number, and the like).

As used herein the term "plurality" means more than one. In certain specific aspects or embodiments, a plurality may mean 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or more, and any integer derivable therein, and any range derivable therein.

As used herein, the term "subject" includes any animal of economic, social or research importance including bovine, equine, ovine, primate, avian and rodent species. Hence, a "subject" may be a mammal such as, for example, a human or a non-human mammal. Also encompassed are microorganism subjects including, but not limited to, bacteria, viruses, fungi/yeasts, protists and nematodes. A "subject" in accordance with the presence invention also includes infectious agents such as prions.

As used herein, the terms "polynucleotide" and "nucleic acid" may be used interchangeably and refer to a single- or double-stranded polymer of deoxyribonucleotide or ribonucleotide bases, or analogues, derivatives, variants, fragments or combinations thereof, including but not limited to DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof. By way of non-limiting example, the source of a nucleic acid may be selected from the group comprising synthetic, mammalian, human, animal, plant, fungal, bacterial, viral, archael or any combination thereof. The terms "polynucleotide" and "nucleic acid" "oligonucleotide" include reference to any specified sequence as well as to the sequence complementary thereto, unless otherwise indicated.

As used herein, the term "total nucleic acid" refers to samples containing both RNA and DNA.

As used herein, the term "GAT" is an acronym for "Gene And Transcript" and refers to the combined measurement of DNA from one gene and RNA transcribed from that gene, or from a group of genes and the RNAs transcribed from those genes. As used herein, the term "NED" is an acronym for "Non-expressed DNA" and refers to the measurement of DNA originating from a region which is not transcribed to RNA.

As used herein, the term "oligonucleotide" refers to a segment of DNA or a DNA-containing nucleic acid molecule, or RNA or RNA-containing molecule, or a combination thereof. Examples of oligonucleotides include nucleic acid targets; substrates, for example, those which can be modified by an MNAzyme; primers such as those used for in vitro target amplification by methods such as PCR; and components of MNAzymes. The term "oligonucleotide" includes reference to any specified sequence as well as to the sequence complementary thereto, unless otherwise indicated. Oligonucleotides may comprise at least one addition or substitution, including but not limited to the group comprising 4-acetylcytidine, 5-(carboxyhydroxylmethyl) uridine, 2'-O-methylcytidine, 5-carboxymethylaminomethyl thiouridine, dihydrouridine, 2'-O-methylpseudouridine, beta D-galactosylqueosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, beta D-mannosylmethyluridine, 5-methoxycarbonylmethyluridine, 5-methoxyuridine, 2-methylthio-N6-isopentenyladenosine, N-((9-beta-ribofuranosyl-2-methylthiopurine-6-yl)carbamoyl)threonine, N-((9-beta-ribofuranosylpurine-6-yl)N-methyl-carbamoyl)threonine, uridine-5-oxyacetic acid methylester, uridine-5-oxyacetic acid (v), wybutoxosine, pseudouridine, queosine, 2-thiocytidine, 5-methyl-2-thiouridine, 2-thiouridine, 4-thiouridine, 5-methyluridine, N-((9-beta-D-ribofuranosylpurine-6-yl)carbamoyl)threonine, 2'-O-methyl-5-methyluridine, 2'-O-methyluridine, wybutosine, 3-(3-amino-3-carboxypropyl)uridine, beta D-arabinosyl uridine, beta D-arabinosyl thymidine.

As used herein, the terms "complementary", and "complementarity" refer to the capacity of nucleotides (e.g. deoxyribonucleotides, ribonucleotides or combinations thereof) to hybridise to each other via either Watson-Crick base-pairing or wobble base pairing. Bonds can be formed via Watson-Crick base-pairing between adenine (A) bases and uracil (U) bases, between adenine (A) bases and thymine (T) bases, between cytosine (C) bases and guanine (G) bases. A wobble base pair is a non-Watson-Crick base pairing between two nucleotides in a polynucleotide duplex (e.g. guanine-uracil, inosine-uracil, inosine-adenine, and inosine-cytosine). Nucleotides referred to as "complementary" or that are the "complement" of each other are nucleotides which have the capacity to hybridise together by either Watson-Crick base pairing or by wobble base pairing between their respective bases.

As used herein, an "enzyme" refers to any molecule which can catalyze a chemical reaction (e.g. amplification of a polynucleotide, cleavage of a polynucleotide etc.)

As used herein, "target amplification" refers to any method that amplified a target nucleic acid including but not limited to the polymerase chain reaction (PCR), strand displacement amplification (SDA), helicase dependent amplification (HDA), Recombinase Polymerase Amplification (RPA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

As used herein, an "amplicon" refers to nucleic acid (e.g. DNA or RNA, or a combination thereof) that is a product of natural or artificial nucleic acid amplification or replication events including, but not limited to, PCR, RT-PCR, SDA, HDA, RPA, LAMP, RCA, TMA, 3SR or NASBA.

As used herein, the terms "nucleic acid enzyme", "catalytic nucleic acid", "nucleic acid with catalytic activity", and "catalytic nucleic acid enzyme" are used herein interchangeably and shall mean a DNA or DNA-containing molecule or complex, or an RNA or RNA-containing molecule or complex, or a combination thereof (i.e. DNA-RNA hybrid molecule or complex), which may recognize at least one substrate and catalyse a modification (such as ligation or cleavage) of the at least one substrate. The nucleotide residues in the catalytic nucleic acids may include the bases A, C, G, T, and U, as well as derivatives and analogues thereof. The terms above include uni-molecular nucleic acid enzymes which may comprise a single DNA or DNA-containing molecule (also known in the art as a "DNA enzyme", "deoxyribozyme" or "DNAzyme") or an RNA or RNA-containing molecule (also known in the art as a "ribozyme") or a combination thereof, being a DNA-RNA hybrid molecule which may recognize at least one substrate and catalyse a modification (such as ligation or cleavage) of the at least one substrate. The terms above include nucleic acid enzymes which comprise a DNA or DNA-containing complex or an RNA or RNA-containing complex or a combination thereof, being a DNA-RNA hybrid complex which may recognize at least one substrate and catalyse a modification (such as ligation or cleavage) of the at least one substrate. The terms "nucleic acid enzyme", "catalytic nucleic acid", "nucleic acid with catalytic activity", and "catalytic nucleic acid enzyme" include within their meaning MNAzymes.

As used herein, the terms "MNAzyme" and "multi-component nucleic acid enzyme" as used herein have the same meaning and refer to two or more oligonucleotide sequences (e.g. partzymes) which, only in the presence of an MNAzyme assembly facilitator (for example, a target), form an active nucleic acid enzyme that is capable of catalytically modifying a substrate. MNAzymes can catalyse a range of reactions including cleavage of a substrate, ligation of substrates and other enzymatic modifications of a substrate or substrates. MNAzymes are also known in the art as "PlexZymes". The MNAzyme only forms when the sensor arms of partzymes A and B hybridize adjacent to each other on the assembly facilitator. The substrate arms of the MNAzyme engage the substrate, the modification (e.g. cleavage) of which is catalyzed by the catalytic core of the MNAzyme, formed by the interaction of the catalytic domains of partzymes A and B. Cleavage of a DNA/RNA chimeric reporter substrate. The MNAzyme may cleave the substrate between a fluorophore and a quencher dye pair, thus generating signal. The terms "multi-component nucleic acid enzyme" and "MNAzyme" comprise bipartite structures, composed of two molecules, or tripartite structures, composed of three nucleic acid molecules, or other multi-partite structures, for example those formed by four or more nucleic acid molecules.

It will be understood that the terms "MNAzyme" and "multi-component nucleic acid enzyme" as used herein encompass all known MNAzymes and modified MNAzymes including those disclosed in any one or more of PCT patent publication numbers WO/2007/041774, WO/2008/040095, WO2008/122084, and related US patent publication numbers 2007-0231810, 2010-0136536, and 2011-0143338 (the contents of each of these documents are incorporated herein by reference in their entirety). Non-limiting examples of MNAzymes and modified MNAzymes encompassed by the terms "MNAzyme" and "multi-component nucleic acid enzyme" include MNAzymes with cleavage catalytic activity (as exemplified herein), disassembled or partially assembled MNAzymes comprising one or more assembly inhibitors, MNAzymes comprising one or more aptamers ("apta-MNAzymes"), MNAzymes comprising one or more truncated sensor arms and optionally one or more stabilizing oligonucleotides, MNAzymes comprising one or more activity inhibitors, multi-component nucleic acid inactive proenzymes (MNAi), and MNAzymes with ligase catalytic activity ("MNAzyme ligases"), each of which is described in detail in one or more of WO/2007/041774, WO/2008/040095, WO2008/122084, US 2007-0231810, US 2010-0136536, and/or US 2011-0143338.

As used herein, the terms "partzyme", "component partzyme" and "partzyme component" refer to a DNA-containing or RNA-containing or DNA-RNA-containing oligonucleotide, two or more of which, only in the presence of an MNAzyme assembly facilitator as herein defined, can together form an "MNAzyme." In certain preferred embodiments, one or more component partzymes, and preferably at least two, may comprise three regions or domains: a "catalytic" domain, which forms part of the catalytic core that catalyzes a modification; a "sensor arm" domain, which may associate with and/or bind to an assembly facilitator; and a "substrate arm" domain, which may associate with and/or bind to a substrate. Partzymes may comprise at least one additional component including but not limited to an aptamer, referred to herein as an "apta-partzyme." A partzyme may comprise multiple components, including but not limited to, a partzyme component with a truncated sensor arm and a stabilizing arm component which stabilises the MNAzyme structure by interacting with either an assembly facilitator or a substrate.

The terms "assembly facilitator" and "MNAzyme assembly facilitator" as used herein refer to entities that can facilitate the self-assembly of component partzymes to form a catalytically active MNAzyme by interaction with the sensor arms of the MNAzyme. As used herein, assembly facilitators may facilitate the assembly of MNAzymes which have cleavage, ligase or other enzymatic activities. In preferred embodiments an assembly facilitator is required for the self-assembly of an MNAzyme. An assembly facilitator may be comprised of one molecule, or may be comprised of two or more "assembly facilitator components" that may pair with, or bind to, the sensor arms of one or more oligonucleotide "partzymes". The assembly facilitator may comprise one or more nucleotide component/s which do not share sequence complementarity with sensor arm/s of the MNAzyme. The assembly facilitator may be a target. The target may be a nucleic acid selected from the group consisting of DNA, methylated DNA, alkylated DNA, RNA, methylated RNA, microRNA, siRNA, shRNA, tRNA, mRNA, snoRNA, stRNA, smRNA, pre- and pri-microRNA, other non-coding RNAs, ribosomal RNA, derivatives thereof, amplicons, or any combination thereof. The nucleic acid may be an "amplicon" and. the amplification may comprise one or more of: PCR, RT-PCR, SDA, HDA, RPA, LAMP, RCA, TMA, 3SR, NASBA or the ligase chain reaction.

The term "detectable effect" as used herein is an effect that can be detected or quantified as an indication that modification of substrate/s has occurred. The magnitude of the effect may be indicative of the quantity of an input such as an assembly facilitator (e.g. a target). The detectable effect may be detected by a variety of methods, including fluorescence spectroscopy, surface plasmon resonance, mass spectroscopy, NMR, electron spin resonance, polarization fluorescence spectroscopy, circular dichroism, immunoassay, chromatography, radiometry, photometry, scintigraphy, electronic methods, electrochemical methods, UV, visible light or infra-red spectroscopy, enzymatic methods or any combination thereof.

The term "substrate" as used herein include any single- or double-stranded polymer of deoxyribonucleotide or ribonucleotide bases, or analogues, derivatives, variants, fragments or combinations thereof, including but not limited to DNA, methylated DNA, alkylated DNA, RNA, methylated RNA, microRNA, siRNA, shRNA, mRNA, tRNA, snoRNA, stRNA, smRNA, pre- and pri-microRNA, other non-coding RNAs, ribosomal RNA, derivatives thereof, amplicons thereof or any combination thereof (including mixed polymers of deoxyribonucleotide and ribonucleotide bases), which is capable of being recognized, acted upon or modified by an enzyme including a catalytic nucleic acid enzyme. A "substrate" may be modified by various enzymatic activities including but not limited to cleavage or ligation. Modification of a "polynucleotide substrate" or "substrate" may provide a "detectable effect" for monitoring the catalytic activity of an enzyme.

A "reporter substrate" as used herein is a substrate that is particularly adapted to facilitate measurement of either the disappearance of a substrate or the appearance of a product in connection with a catalyzed reaction. Reporter substrates can be free in solution or bound (or "tethered"), for example, to a surface, or to another molecule. A reporter substrate can be labelled by any of a large variety of means including, for example, fluorophores (with or without one or more additional components, such as quenchers), radioactive labels, biotin (e.g. biotinylation) or chemiluminescent labels.

The terms "probe" as used herein refers to an oligonucleotide that is used for detection of a target nucleic acid. Non-limiting examples of probes include TaqMan probes; Molecular Beacon probes; and nucleic acid enzyme substrates capable of catalytic modification by a nucleic acid enzyme.

As used herein, the term "base" will be understood to have the same meaning as the term "nucleotide".

Any description of prior art documents herein, or statements herein derived from or based on those documents, is not an admission that the documents or derived statements are part of the common general knowledge of the relevant art.

For the purposes of description all documents referred to herein are hereby incorporated by reference in their entirety unless otherwise stated.

Abbreviations

The following abbreviations are used herein and throughout the specification:
GAT: Gene And Transcript
NED: Non-Expressed DNA
FC: Fold Change
TR: Theoretical ratio
Ct: Threshold Cycle/Cycle threshold
DMEM: Dulbecco's Modified Eagle medium
LLE: Liquid-Liquid extraction
MOL Multiplicity of Infection
PI: Post-infection
PT: Post-treatment
TNA: Total Nucleic Acid
IF: immunofluorescence
IFU: Inclusion Forming Units
MIC: Minimum Inhibitory Concentration
TOC: Test of Cure
NAAT: Nucleic Acid Amplification Technology
STI: Sexually Transmitted Infection
AMR: antimicrobial resistance
EMA: ethidium monoazide
PMA: propodium monoazide
MNAzyme: multi-component nucleic acid enzyme, or multipartite nucleic acid enzyme;
Partzyme: Partial enzyme containing oligonucleotide;
ave; average
PCR: polymerase chain reaction;
gDNA: genomic DNA
dsDNA: double stranded DNA
rc: reverse complement
NTC: No template control
qPCR: Real-time quantitative PCR
$R^2$; Correlation coefficient
nM; Nanomolar
mM; Millimolar
µL; Microlitre
dNTP; Deoxyribonucleotide triphosphate
NF-$H_2O$: nuclease-free water;
F: fluorophore;
Q: quencher;
N=A, C, T, G, or any analogue thereof;
N'=any nucleotide complementary to N, or able to base pair with N;
W: A or T;
R: A, G, or AA;
rN: any ribonucleotide base;

rR: A or G;
rY: C or U;
M: A or C;
H: A, C, or T;
D: G, A, or T;
JOE or 6-JOE: 6-carboxy-4',5'-dichloro-2',7'-dimethoxyfluorescein;
FAM or 6-FAM: 6-Carboxyfluorescein.
BHQ1: Black Hole Quencher 1
BHQ2: Black Hole Quencher 2
RT-PCR: reverse transcription polymerase chain reaction
SDA: strand displacement amplification
HDA: helicase dependent amplification
RPA: Recombinase Polymerase Amplification
LAMP: loop-mediated isothermal amplification
RCA: rolling circle amplification
TMA: transcription-mediated amplification
3SR: self-sustained sequence replication
NASBA: nucleic acid sequence based amplification
IB: Iowa Black® FQ
IBR: Iowa Black® RQ
mRNA: messenger RNA
tRNA: transfer RNA
rRNA: ribosomal RNA

DETAILED DESCRIPTION

The following detailed description conveys exemplary embodiments of the present invention in sufficient detail to enable those of ordinary skill in the art to practice the present invention. Features or limitations of the various embodiments described do not necessarily limit other embodiments of the present invention or the present invention as a whole. Hence, the following detailed description does not limit the scope of the present invention, which is defined only by the claims.

The present invention provides methods capable of detecting the presence, absence and/or perturbation of transcription in cells, organisms, viruses and the like. The methods may be used, for example, to detect the presence or absence of active transcription; to detect perturbation or alteration of transcription levels in response to agents or in disease states; to detect the absence of active transcription in samples containing dead cells and associated cell debris; and/or to differentiate between live and dead cells. By way of non-limiting example, when a subject is infected with bacteria, antibiotics can be administered with the aim of clearing the infection. For such infections a test of cure (TOC) is desirable to confirm successful clearance of bacteria. Previously reported methods for measuring viability of bacteria include protocols for measuring bacterial RNA or bacterial DNA. The problem with these approaches is that residual RNA and or DNA associated with dead cells or cell debris may persist for considerable time following cell death and cure. Further, methods that attempt to normalise levels of RNA using DNA, for example AST, require accurate quantification of extracted nucleic acids.

The present invention provides, among other things, improved methods for differentiating between specimens containing viable cells or pathogens undergoing active transcription and those containing dead cells or nucleic acid debris. Further, the invention provides improved methods for normalising of data relating to measurements of expressed RNA and which allow inter-sample comparison without the need the quantify the concentration of total TNA present in each of the sample. Since the method allows inter-sample comparison and elucidation of upregulation or downregulation the data generated using this invention can be represented in the format of heat maps.

Vita Index

The strategy involves amplification of specific genes and their RNA transcripts which are then normalised to a specific DNA sequence which is known to not be transcribed. During RT-PCR, primers which target a specific transcript will also amplify the gene from which it was transcribed. A measure of a gene and its associated transcripts is termed herein as GAT (Gene And Transcript). Further, during RT-PCR, if primers are present for a region of DNA which is not transcribed into RNA then this DNA only can also be amplified. This is referred to as NED (Non-Expressed_DNA). Target amplification protocols for the simultaneous estimation of GAT and NED are termed VITA (Viable Transcript Analysis) tests, and hence when amplification is by PCR the method is termed VITA PCR.

Analysis of VITA PCR allows measurement of the levels of active transcription which can be calculated in various manners. By way of example, the data can be used to obtain a VITA Index which equals the Fold Change (FC) for the Specimen calculated as $2^{\Delta Ct}$ divided by Theoretical Ratio (TR) anticipated in the absence of active transcription (residual DNA only). For, example the difference in Ct values between GAT and NED in a specimen allows an estimate of the FC observed for GAT (DNA plus RNA) versus DNA only (NED), wherein the $FC=2^{\Delta Ct}=2^{(Ct\ NED-Ct\ GAT)}$. The TR anticipated in the absence of active transcription from GAT equals the number of genes amplified when calculating the GAT divided by the number of sequences amplified to calculate the NED. Assuming the NED is measured for a single DNA sequence, then if GAT measures amplification a single gene, the TR=number of primer sets for GAT divided by the number of primer sets for NED=1/1=1; if GAT measures amplification of two genes (or regions) the TR=2/1=2, and if GAT measures amplification of three genes the TR would be 3/1=3 and so on. For example, the VITA Index for a specimen with a Ct (GAT) of 10 and a Ct (NED) of 13 would have a FC value=$2^{\Delta Ct}=2^3=8$ which would result in a VITA Index of 8 (if TR=1) or a VITA Index of 4 (if TR=2).

The VITA Index provides a measure of transcriptional activity with the cell population which is valid regardless of whether the cells are (i) viable, (ii) dead (with or without total clearance of residual, but detected, low levels of nucleic acids) or (iii) under some level of metabolic stress due to the presence of an external stimuli, for example the presence of a compound or drug.

The approach overcomes the problems encountered by previous investigators who have tried to use either RNA or DNA as a marker of the presence of live cells. These studies have shown that in some cases RNA and/or DNA can persist for weeks following cell death. The VITA Index provides a measure of levels of active transcription per gene copy as a method to establish the presence of live organisms. By way of example, this protocol could be used for assessing test of cure (TOC) in patients who have been given antibiotics to treat a bacterial infection.

Further, the method can measure more subtle perturbations of transcriptional activity. For example if cells are incubated in the presence of a compound which has deleterious effects on cell viability and/or vitality, the impact of this compound can be quantified using the VITA Index. An example of an application whereby this measure would be useful would be when specimens containing infectious bacteria are incubated in the presence of antibiotics and analysed using VITA PCR. If the bacteria are sensitive to the antibiotic then the VITA Index will decrease. Conversely if bacteria are resistant to the antibiotic then the Index would not change significantly.

Amplification Reactions

The methods of the present invention can be applied to quantitative measurements of products arising from nucleic acid amplification reactions. Any nucleic acid amplification reaction capable of generating amplicons from target DNA and/or target RNA (e.g. mRNA) sequences can be used. For example, polymerase chain reaction (PCR) amplifications such as reverse-transcriptase PCR (RT-PCR), quantitative PCR (qPCR), and/or digital PCR (dPCR) may be used. Other non-limiting examples of suitable amplification reactions include strand displacement amplification (SDA), loop-mediated isothermal amplification (LAMP), rolling circle amplification (RCA), recombinase polymerase amplification (RPA), helicase dependent amplification (HDA), strand invasion based amplification (SIBA), transcript-mediated amplification (TMA), self-sustained sequence replication (3SR), nucleic acid sequence based amplification (NASBA), and combinations thereof.

Quantitative measurements of products arising from the amplification reactions can be made using any suitable methods known in the art. The methods may be based, for example, on amplicon copy number, cycle threshold (Ct) and the like, and involve, for example, measuring fluorescence.

Test Subjects

The methods of the present invention can be applied to any suitable subject in which the degree of transcription is of interest (for example, as a measure of any one or more of transcription level, perturbation of transcription, viability, death, response to agents such as drugs and other compounds, and so on).

In some embodiments, the subject is a cell, or a population of cells. The cells may be unicellular organisms (e.g. bacteria, archae, protozoa, unicellular algae, unicellular fungi, unicellular amoeba). In other embodiments, the subject is a virus.

Cells and viruses analysed in accordance with the methods of the present invention may be components of a biological sample. Non-limiting examples of biological samples include whole blood or a component thereof (e.g. blood cells, plasma, serum), urine, saliva, lymph, bile fluid, sputum, tears, cerebrospinal fluid, bronchioalveolar lavage fluid, synovial fluid, semen, ascitic tumour fluid, breast milk and pus.

Exemplary Embodiments

In some embodiments the present invention provides methods for determining a combined transcription normalised value (nV±), which is predictive of a presence or an absence of transcriptional activity in a cell, organism or virus (and the like). Similar methods can be applied for determining the differences in transcriptional activity between two populations of samples, such as population of the cells, organisms, or viruses known to be (i) resistant to the drug and (ii) sensitive to the drug.

By way of non-limiting example only:
nV± may be calculated as a midpoint between the critical point in the lower-tailed test of nV+ and the critical point in the upper-tailed test nV−, both with 95% confidence level.

$$nV\pm=((nV+-1.645*\delta+)+(nV-+1.645*\delta-))/2$$

where:
nV+ is the mean of nV values obtained from individuals of a population of the cells, organisms, or viruses known to have transcriptional activity.
nV− is the mean of nV values obtained from individuals of a population of the cells, organisms, or viruses known not to have transcriptional activity.
δ+ is the standard deviation of nV values obtained from individuals of a population of the cells, organisms, or viruses known to have transcriptional activity and the critical point.
δ− is the standard deviation nV values obtained from individuals of a population of the cells, organisms, or viruses known not to have transcriptional activity.

EXAMPLES

The present invention will now be described with reference to the following specific examples, which should not be construed as in any way limiting.

Example 1: In Vitro Generation of *Chlamydia* Samples in Presence or Absence of Antibiotics, Analysis of Viability Using Immunofluorescence and Methods for Extraction of TNA from Samples 1.1 Culture

*Chlamydia trachomatis* (serovar D, lab strain UW-3/Cx) samples were grown in HEp-2 cells and either not treated (not incubated with the antibiotic Azithromycin) to reproduce a Positive Control for "Alive bacteria", or incubated with different concentrations of Azithromycin, to create samples which simulate dead bacteria. (Azithromycin is the first line treatment of chlamydial genital infections). The conditions were as follows.

The human epithelial cell line (HEp-2) (ATCC® CCL-23™) were grown in Dulbecco's Modified Eagle medium (DMEM) (Sigma-Aldrich) supplemented with 10% heat-inactivated Fetal Bovine Serum (FBS) (Sigma-Aldrich), 100 mg/mL Streptomycin (Invitrogen Corporation), 50 mg/mL Gentamicin (Life Technologies) and 20 mM Glutamine (Sigma Aldrich), incubated at 37° C. with 5% $CO_2$. *Chlamydia trachomatis* (serovar D) was inoculated on a HEp-2 monolayer, present on a flat bottomed 6-well plate (Thermo Fisher) at a Multiplicity of Infection (MOI) of 1. The infection was completed by centrifugation-assisted inoculation at 500 g for 30 minutes at a temperature of 28° C. and subsequently incubated, under conditions specified above.

1.1.1 Treatment Protocol A

At 4 hours post-infection (PI), DMEM was replaced with addition of variable doses of the antibiotic Azithromycin (Sigma Aldrich) and again incubated at 37° C. with 5% $CO_2$ until harvested. The different antibiotic concentrations used were i) No antibiotic (0 µg/mL), ii)<MIC (0.008 µg/mL), iii) MIC (0.064 µg/mL) and iv)>MIC (0.512 µg/mL). The "MIC dose" chosen for these experiments is slightly higher than that observed in the laboratory using this current strain; however, it was specifically chosen to ensure reproducible killing of the bacteria. The dose used is also consistent with documented MIC analysis in the literature. At 44 hours PI, cells were harvested using sucrose-phosphate-glutamate (SPG) buffer (250 mM sucrose, 10 nM sodium phosphate and 5 mM L-glutamate). Half the volume was stored for viability counts through immunofluorescent staining (See 1.2 Viability/Immunofluorescence staining); the other half was kept for extraction of TNA and/or RNA. Samples were stored at −80° C. until further processing. Each condition was cultured in triplicate.

1.1.2 Treatment Protocol B

At 4 hours PI, DMEM was replaced, with addition of cycloheximide and incubation was continued. Once in an exponential growth phase, 24 hours PI, treatment was applied. This was achieved by replacing the DMEM for each infection, with addition of either i) no antibiotic, or ii) antibiotic at a level higher than the MIC for azithromycin (0.128 μg/mL). Samples were then harvested for either 30 minutes, 1 hour or 6 hours Post Treatment (PT) using SPG buffer and stored at −80° C. until further processing.

1.1.3 Treatment Protocol C

After infection, there was no change of media at the 4 hour time point, essentially creating an unsynchronised population, which would be more similar to in vivo conditions. Once at an exponential growth phase, 20 hours PI, treatment was applied. This was achieved by replacing the DMEM for each well, with addition of either i) no antibiotic, or ii) antibiotic (0.256 μg/mL of Rifampicin). Samples were then either incubated at 37° C. with 5% $CO_2$, and harvested after 5 minutes PT; or incubated at room temperature and harvested after 15 minutes PT. SPG buffer was used for harvest and TNA was extracted immediately after. Strains used for this treatment protocol were Strain 1) serovar D lab strain (UW-3/Cx), susceptible to rifampicin, and Strain 5) serovar L2 lab created mutant strain, resistant to Rifampicin.

1.1.4 Treatment Protocol D

After infection, there was no change of media at the 4 h time point. Once in an exponential growth phase, either 20 or 24 hours PI, cells were treated with varying doses of azithromycin achieved by replacing the DMEM in each well with addition of desired amount of antibiotic. Doses of antibiotic treatment added to the infection were i) no antibiotic, ii) 0.128 μg/mL, iii) 0.192 μg/mL, iv) 0.256 μg/mL and v) 0.512 μg/mL. Samples were then incubated at 37° C. with 5% $CO_2$ and harvested at 1 hour PT, using SPG buffer and stored at −80° C. until further processing or extracted immediately after harvest.

1.1.5 Treatment Protocol E

After infection, there was no change of media at the 4 h time point. Once in an exponential growth phase, 20 hours PI, cells were treated with a single dose of different antibiotics. Antibiotics used were i) Azithromycin, ii) Doxycycline and iii) Rifampicin, each at a dose of 0.256 μg/mL. Strains used for this treatment protocol were Strain 1) serovar D lab strain (UW-3/Cx), Strain 2) serovar L2 wild type lab strain (434/Bu), Strain 3) serovar L2 lab created mutant strain, resistant to trimethoprim, Strain 4) serovar L2 lab created mutant strain, resistant to Spectinomycin and Strain 5) serovar L2 lab created mutant strain, resistant to Rifampicin. MIC for all serovars and each antibiotic was predetermined, using standard procedures documented in literature, and listed in the table below. According to the MIC analysis (Table 1), all strains used were susceptible to Azithromycin and Doxycycline antibiotics. Strains 1, 2, 3 and 4 are also susceptible to rifampicin, whilst strain 5 is resistant to that same antibiotic. Samples were then incubated at 37° C. with 5% $CO_2$ and harvested at 1 hour PT, using SPG buffer and extracted immediately. Two biological replicates were obtained for each condition.

TABLE 1

Minimum inhibitory concentration (MIC) of antibiotics used for antibiotic susceptibility testins

| | Antibiotic dose (μg/mL) | | | | |
|---|---|---|---|---|---|
| | Strain 1 | Strain 2 | Strain 3 | Strain 4 | Strain 5 |
| Azithromycin | 0.032 | 0.032 | 0.016 | 0.016 | 0.032 |
| Doxycycline | 0.128 | 0.064 | 0.032 | 0.064 | 0.064 |
| Rifampicin | 0.008 | 0.004 | 0.004 | 0.004 | 8.192 |

1.1.6 Treatment Protocol F

At 4 hours PI, DMEM was replaced with addition of cycloheximide (1 μg/mL) to synchronise the infection and halt the production of proteins by the host-cell. At this time point, addition of antibiotic was also carried out, with half the number of wells left untreated and the other half treated with a high dose of the antibiotic Azithromycin. Cells were again incubated at 37° C. with 5% $CO_2$ until harvested. The different conditions used were i) No antibiotic representing "Alive CT" or ii) Plus antibiotic (0.512 μg/mL) —representing "Dead CT". At 44 hours PI the cells were harvested using SPG buffer and mixed at different ratios to create samples with varying percentages of viable and non-viable cells, as per the table below. Half the volume was stored for viability counts through immunofluorescent staining (See 1.2 Viability/Immunofluorescence staining; data not included); the other half was kept for extraction of TNA. These were then stored at −80° C. until further processing.

| Viable load | "Alive" sample volume (uL) | "Dead" sample volume (uL) | Total volume (uL) | Total volume used in extraction (uL) |
|---|---|---|---|---|
| 0% | 0 | 500 | 500 | 300 |
| 0.1% | 0.5 | 499.5 | 500 | 300 |
| 0.2% | 1 | 499 | 500 | 300 |
| 0.5% | 2.5 | 497.5 | 500 | 300 |
| 1% | 5 | 195 | 500 | 300 |
| 10% | 50 | 450 | 500 | 300 |
| 20% | 100 | 400 | 500 | 300 |
| 50% | 250 | 250 | 500 | 300 |
| 100% | 500 | 0 | 500 | 300 |

1.2 Viability/Immunofluorescence Staining

Samples harvested for viability count were serially diluted and cultured on a fresh HEp-2 monolayer, present on a flat bottomed 96 well plate (Nunc™, Thermo Fisher). The infection was completed by centrifugation-assisted inoculation at 500 g for 30 minutes at a temperature of 28° C. and subsequently incubated at 37° C. with 5% $CO_2$. Each sample was cultured in triplicates. At 38 hours PI the cultures were fixed with methanol and stained for microscopy.

Direct immunofluorescence (IF) staining was performed using antibodies against CtHtrA, MOMP (Biodesign), and secondary antibodies conjugated to Alexa fluor dyes (Invitrogen). DAPI (4', 6-Diamidino-2-Phenylindole, Dilactate) (Invitrogen) was also added for host cell staining. The specimens were examined at a 100× magnification with the fluorescent microscope IN Cell Analyser 2200 (GE Healthcare Life Sciences). HEp-2 cells displayed a blue colour, whilst *chlamydia* inclusions were presented in green. Inclusion forming units (IFU $mL^{-1}$) was determined by counting inclusions from 10 representative fields of view, for each well and each serial dilution. Extrapolation of the field of view size to the size of wells was done to calculate the total number of inclusion in a given well. Dilutions and volumes added were also accounted for.

Immunofluorescent imaging of cells treated as described in Treatment Protocol A (1.1.1) are shown in FIG. 3A and the results obtained by counting IFU/ml from these images are shown in FIG. 3B; with results normalised to the value obtained for cells treated above the MIC (>MIC). Cells which were untreated, and treated with various doses of antibiotic, each had different numbers of infective units of *chlamydia*.

1.3 Total Nucleic Acid (TNA) Extraction 1.3.1 Extraction Protocol A

Samples harvested for TNA extraction were thawed on ice and cell debris was pelleted at 800 g for 10 minutes at 4° C., followed by centrifugation of the supernatant at 14000 rpm for 20 minutes at 4° C. The pellet was re-suspended in a proteinase K digestion mix (10 mg/mL Proteinase K (Ambion), 1 mM Tris pH7.5, 0.5M EDTA, 5M NaCl, 10% SDS and nuclease free water (Ambion) and incubated at 56° C. for 60 minutes. Following digestion, Phenol:Chloroform:Isoamyl (25:24:1, pH 6.5-6.9, Sigma Aldrich) was added to the mix, vortexed vigorously and centrifuged for 5 minutes at maximum speed. The upper phase was kept with addition of sodium acetate (3M, pH5.2, Sigma Aldrich) and 100% ethanol (Sigma Aldrich). This was again vortexed and incubated for 20 minutes (10 minutes at room temperature and 10 minutes at −20° C.). TNA was then pelleted at high speed (14000 rpm) for 10 minutes, following two washing steps using 70% ethanol. The pellet was then air dried for 15 minutes before elution in 50 µL of water. The eluate was quantified and stored at −80° C.

1.3.2 Extraction Protocol B

Samples harvested were thawed on ice, followed by pelleting of cells at 14000 rpm for 20 min at 4° C. Following this step, the manufacturer's instructions for simultaneous extraction of DNA and RNA were followed, using the PuriSpin FireMonkey extraction kit (RevoluGen).

1.3.3 Extraction Protocol C

Samples harvested were thawed on ice, followed by pelleting of cells at 14000 rpm for 20 min at 4° C. Following this step, the manufacturer's instructions for Purification of Total RNA from Animal Cells, with additional on-column DNase digestion were followed. The extraction was done using the RNeasy Mini Kit (Qiagen).

Example 2: Analysis of a Gene and its Transcripts in Untreated and Treated Cells in a Two Well Assay The following example estimates levels of DNA and GAT in TNA samples extracted from HEp-2 cells infected with *Chlamydia trachomatis* (serovar D). TNA was extracted from cells which were not incubated with antibiotic (untreated, viable cells), and from cells incubated with antibiotic at a concentration eight times below the MIC (<MIC), at the MIC (MIC) or at 8 times greater than the MIC (>MIC), as described in example 1 (1.1.1 Treatment Protocol A). *Chlamydia* DNA and RNA was amplified using primers targeting the omp1 gene and its transcripts. The levels of GAT were estimated by RT-PCR wherein both the omp1 gene and its transcripts (DNA plus RNA) were amplified. The levels of the omp1 gene only (DNA only) were measured in a separate PCR which lacked reverse transcriptase.

2.1 Partzyme Oligonucleotides

Partzymes were designed to assemble into active MNAzymes when they bound to amplicons generated by amplification of both the omp1 gene or omp1 transcripts. Once assembled, the MNAzyme could cleave the reporter substrate Sub2-FB. The sequences of Partzyme A and Partzyme B are listed below, from 5' to 3'. Bases in bold hybridize with the target, underlined bases form part of the catalytic core in the assembled MNAzyme and bases in italic refer to sequence which hybridizes to the substrate.

Partzyme A omp1_A4/2-P
SEQ ID NO: 1
TGGTCTCGAGCATTGAACGA<u>ACAACGA</u>*GAGGAAACCTT*/3Phos/

Partzyme B omp1_B5/2-P
SEQ ID NO: 2
*TGCCCAGGGAGGCTAGCT*CATGTTCTCGATTAAGGCTG/3Phos/

2.2 Reporter Substrate

In the current example, the substrate was end-labelled with a 6-FAM moiety at the 5' end (indicated by a "F" in the name of the substrate below) and an IABkFQ quencher moiety at the 3' end (indicated by an "IB" in the name of the substrate below). Cleavage of the substrate was monitored at 516 nm (FAM emission wavelength) with excitation at 492 nm (FAM excitation wavelength). The reporter substrate for this example is shown below with the sequence, 5' to 3'. The lower case bases represent RNA and the upper case bases represent DNA.

Sub2-FB
SEQ ID NO: 3
AAGGTTTCCTCguCCCTGGGCA 2.3 PCR Primers for Amplification of the Omp1 Gene and Transcripts In vitro amplification of TNA template extracted from cells infected with *Chlamydia trachomatis* was performed using the primers listed below. The Forward and Reverse primers were used to amplified DNA within the omp1 gene by PCR, and both DNA and RNA within the omp1 gene and transcripts by RT-PCR. All sequences are written 5' to 3'.

Forward primer 5omp1:
SEQ ID NO: 4
CTTCTTCCTGGGACGAACG

Reverse primer 3omo1:
SEQ ID NO: 5
TGGCCTGAGGAATGTCTTGC 2.4 Preparation of TNA

RNA and DNA (TNA) were co-extracted from *Chlamydia trachomatis* (serovar D) which had been cultured in HEp-2 cells as per example 1 (1.1 Culture and 1.1.1 Treatment Protocol A). Extraction was performed as a liquid-liquid extraction (LLE) technique, using phenol:chloroform:isoamyl, also described in example 1 (1.3 Total Nucleic Acid (TNA) extraction, 1.3.1 Extraction Protocol A).

2.5 PCR and RT-PCR mixes

Both PCR and RT-PCR mixes contained 40 nM of 5' primer, 200 nM of 3' primer, 200 nM of partzyme A, 200 nM of partzyme B, 200 nM of Sub2-FB, 1× SensiFAST Probe No-ROX Mix (Bioline), 8 mM MgCl$_2$ (Bioline), and nuclease free water (Ambion) in a total volume of 20 µL. In addition RT-PCR mixes contained 0.2 U/µL RiboSafe RNase Inhibitor (Bioline) and 0.2 µL of Reverse Transcriptase (Bioline). Reactions were performed in triplicate on a BioRad® CFX96 thermocycler using the same cycling parameters: 48° C. for 10 minutes, 95° C. for 2 min, 10 cycles of 95° C. for 5 seconds and 61° C. for 30 seconds (minus 0.5° C. per cycle), and 30 cycles of 95° C. for 5 seconds and 52° C. for 50 seconds. RT-PCR and PCR mixes contained either 5 μL of TNA template (1/100 dilution) or no template (dH$_2$O).

2.6 Results

*Chlamydia* DNA and RNA (GAT), or DNA only, was amplified by RT-PCR and PCR respectively using TNA extracted from viable untreated cells and from cells incubated with antibiotic at concentrations below (<MIC), equal to (MIC) or above the MIC (>MIC). Table 2 shows the threshold cycle (Ct) values measured for each reaction type and sample. The ΔCt was calculated as the differences between the Ct values for the PCR (DNA only) and RT-PCR (GAT) obtained from amplification plots. In turn, the fold change (ratio of the numbers of copies of RNA plus DNA (GAT) versus DNA only, which would theoretically lead to those ΔCt values, was estimated as $2^{\Delta Ct}$ and plotted in FIG. 3C. The results were then compared to the viability in each cell population (FIG. 3B).

TABLE 2

Results of PCR and RT-PCR analysis of TNA from treated and untreated samples

| Sample | Threshold (Ct) | | ΔCt (CtA − CtB) | Fold Change $2^{\Delta Ct}$ |
| --- | --- | --- | --- | --- |
| | A: PCR amplifying OmpI DNA only | B: RT-PCR amplifying OmpI DNA and omp1 RNA | | |
| No Antibiotic | 11.42 | 10.33 | 1.10 | 2.14 |
| <MIC | 13.96 | 12.76 | 1.19 | 2.29 |
| MIC | 21.88 | 21.42 | 0.47 | 1.38 |
| >MIC | 21.84 | 21.47 | 0.37 | 1.29 |
| No TNA | No Ct | No Ct | | |

Theoretically, if cells were no longer infected with *chlamydia*, no transcripts or only very low residual levels of transcripts or their fragments would be detectable. Similarly, only low residual levels of genomic DNA, or fragments of this, would be detectable, however, the amount of DNA detected could be anticipated to be greater than the amount of RNA since DNA is inherently more stable than RNA.

Analysis of results shows that when TNA samples, extracted from untreated samples, or from samples treated at below the MIC, were amplified then the Ct value for RT-PCR observed was lower than that observed for the PCR (Table 2), consistent with active transcription In these samples. For reactions using TNA from culture treated at the MIC level or above, the Δ Ct values were lower (Table 2), consistent with little or no transcription.

Previous studies have shown that detection of either DNA or RNA per sec is not a reliable measure of clearance of *Chlamydia trachomatis*. The data from this example demonstrates that the ratios of the fold changes between DNA (measured by PCR) and GAT, (DNA plus RNA, measured by RT-PCR) has a similar trend as the measure of viability (PI) for untreated and treated cells as evidenced by comparison of graph in FIGS. 3B-C. Whilst this example demonstrates the utility of examining RNA and DNA ratios, this experiment does not exemplify the invention as the DNA only target is still expressed in both reactions. As such determination of the DNA/RNA versus DNA only required two parallel reactions performed with and without reverse transcriptase. This makes direct comparison of results more difficult. As such a more preferred approach would use a method as per the invention wherein different nucleic acid subpopulations (DNA only versus DNA plus RNA) could be co-amplified in a single VITA RT-PCR.

Example 3: Screening of GAT and NED Targets

The following example demonstrates the methods of screening for appropriate targets for GAT and NED assays. Nucleic acids were extracted from HEp-2 cells infected with *Chlamydia trachomatis* (serovar D). TNA and RNA were extracted from viable cells harvested at 24 h PI. Nucleic acids were then amplified using primer pairs targeting the selected gene and its transcripts (GAT), or an non-transcribed gene only (NED). The appropriateness of each a target was determined by comparison of the (i) detection of RNA by RT-PCR in total RNA, wherein both the gene and its transcripts would be detected and (ii) detection of DNA by PCR wherein only the gene DNA would be detected. In theses experiment it would be predicted atht the Ct of GAT to display a difference between both reactions, whereas the Ct of NED should display no difference.

3.1 Partzyme Oligonucleotides

Partzymes were designed to assemble into active MNAzymes when they bound to amplicons generated by amplification of either the omp1 gene or omp1 transcripts. Once assembled, the MNAzyme could cleave the reporter substrate Sub102(20)-FB. A second pair of partzymes was designed to assemble into an active MNAzymes when bound to amplicons generated by amplification of a non-transcribed DNA region denoted infA_IGR thus providing a measure of NED. Once assembled, this MNAzyme could cleave the reporter substrate Sub72-A1B. The sequences of Partzyme A and Partzyme B for each MNAzyme are listed below, from 5' to 3'. Bases in bold hybridize with the target, underlined bases form part of the catalytic core in the assembled MNAzyme and bases in italic refer to sequence which hybridizes to the substrate.

```
Partzyme A for GAT omp1_A4/102-P
                                        SEQ ID NO: 6
TGGTCTCGAGCATTGAACGAACAACGAGGGACGTCGA/3Phos/

Partzyme B for GAT omp1_B5/102(20)-P
                                        SEQ ID NO: 7
CGGTAGAGGAGGCTAGCTCATGTTCTCGATTAAGGCTG/3Phos/

Partzyme A for NED CTinfAIGR_A4/72-P
                                        SEQ ID NO: 8
TCGACTAAACAGAAAATGTCAAAACAACGAGAGGCGTGAT/3Phos/

Partzyme B for NED CTinfAIGR_B5/72-P
                                        SEQ ID NO: 9
CTGGGAGGAGAGGCTAGCTCAACTTGTCAAAAAACAGAAGG/3Phos/
```

3.2 Reporter Substrate

In the current example, two different reporter substrates were used, each labelled with distinct fluorophores. Sub102 (20)-FB was end-labelled at the 5' end with 6-FAM and with IABkFQ at the 3' end, and its cleavage was monitored at 516 nm with excitation at 492 nm. Sub72-A1B was labelled with ATTO™ Rho101 at the 5' end and with IAbRQSp at the 3' end, and its cleavage was monitored at 609 nm with excitation at 592 nm. The reporter substrates for this example are shown below with the sequence, 5' to 3'. The lower case bases represent RNA and the upper case bases represent DNA.

```
for GAT Sub102(20)-FB
                                     SEQ ID NO: 10
TCGACGTCCCguCCTCTACCG for NED Sub72-A1B
                                     SEQ ID NO: 11
ATCACGCCTCguCTCCTCCCAG
```

3.3 PCR Primers for Amplification GAT and NED

In vitro amplification of TNA and RNA template extracted from cells infected with *Chlamydia trachomatis* was performed using the primers listed below. The Forward and Reverse primers were used to amplify a region of the omp1 gene and transcripts (GAT) and infA_IGR DNA (NED) by PCR and RT-PCR. All sequences are written 5' to 3'.

```
Forward primer for GAT 5omp1:
                                     SEQ ID NO: 4
CTTCTTCCTGGGACGAACG Reverse primer for GAT 3omp1:
                                     SEQ ID NO: 5
TGGCCTGAGGAATGTCTTGC Forward primer for NED 5CTinfAIGR_2
                                     SEQ ID NO: 12
GAGAGAGTGATTATATCGACTAA Reverse primer for NED 3CTinfAIGR_1
                                     SEQ ID NO: 13
CAAGAGAGAATGTCAAAAGATAC
```

3.4 Preparation of TNA and RNA

Nucleic acids were extracted from *Chlamydia trachomatis* (serovar D) which had been cultured in HEp-2 cells, as described in example 1 (1.1 Culture). At 4 hoursPI, DMEM was replaced with cycloheximide, to synchronise the infection and stop protein synthesis by the host. Cells were again incubated at 37° C. with 5% $CO_2$ until harvested at 24 h post-infection, at an exponential growth phase of the bacteria.

Extraction of TNA was performed as a LLE technique, using phenol:chloroform:isoamyl, also described in example 1 (1.3 Total Nucleic Acid (TNA) extraction, 1.3.1 Extraction Protocol A). with the following modification; cell debris pelleting step was not performed during extraction of the samples in this example.

Extraction of RNA was performed using the RNeasy Mini Kit (Qiagen), as defined in example 1 (1.3 Total Nucleic Acid (TNA) extraction, 1.3.3 Extraction Protocol C) and following manufacturer's instructions for Purification of Total RNA from Animal Cells with additional on-column DNase digestion.

3.5 PCR and RT-PCR Mixes

Both PCR and RT-PCR mixes contained 40 nM of 5' primer, 200 nM of 3' primer, 200 nM of partzyme A, 200 nM of partzyme B, 200 nM of Sub2-FB for GAT and 200 nM of Sub72-A1B for NED, 1x SensiFAST Probe No-ROX Mix (Bioline), 8 mM $MgCl_2$ (Bioline) and nuclease free water (Ambion) in a total volume of 20 µL. In addition RT-PCR mixes contained 0.2 U/µL RiboSafe RNase Inhibitor (Bioline) and 0.2 µL of Reverse Transcriptase (Bioline). Reactions were performed on a BioRad® CFX96 thermocycler using the same cycling parameters: 48° C. for 10 minutes, 95° C. for 2 min, 10 cycles of 95° C. for 5 seconds and 61° C. for 30 seconds (minus 0.5° C. per cycle), and 30 cycles of 95° C. for 5 seconds and 52° C. for 50 seconds. RT-PCR and PCR mixes contained either 5 µL of TNA or RNA template (1/100 dilution) or no template ($dH_2O$).

3.6 Results

*Chlamydia* DNA and RNA, or DNA only, was amplified by RT-PCR and PCR respectively in RNA and TNA samples, harvested from viable untreated cells at 24 hours PI. Table 3A denotes the amplicon types and origin from reactions performed. Table 3B shows the threshold cycle (Ct) values measured for each reaction type and sample. The ΔCt was calculated as the differences between the Ct values for the PCR (DNA only) and RT-PCR (DNA and RNA) obtained from amplification plots (FIGS. 4A-D).

TABLE 3A

Potential Amplicon Types and Origin

| | | Nucleic Acid Species with potential to generate amplicons | |
|---|---|---|---|
| | Sample | PCR | RT-PCR |
| Omp 1 GAT | RNA | Contaminating DNA (omp1 gene) | RNA - omp1 transcripts Contaminating DNA (Omp1 gene) |
| | TNA | Genomic DNA - omp1 gene | Genomic DNA and RNA - omp1 gene and omp1 transcript |
| InfAIG NED | RNA | Contaminating DNA (infAIGR DNA) | Contaminating DNA (infAIGR DNA) |
| | TNA | Genomic DNA infAIG DNA | Genomic DNA infAIG DNA |

TABLE 3B

Threshold Values from PCR and RT-PCR analysis of TNA and RNA samples

| | | Threshold (Ct) | | |
|---|---|---|---|---|
| | Sample | DNA only (PCR) | DNA and RNA (RT-PCR) | ΔCt PCR – RT-PCR |
| Omp 1 GAT | RNA | 19.85 | 7.09 | 12.76 |
| | No RNA | No Ct | No Ct | |
| | TNA | 17.36 | 12.44 | 4.92 |
| | No TNA | No Ct | No Ct | |
| InfAIG NED | RNA | 20.12 | 19.29 | 0.83 |
| | No RNA | No Ct | No Ct | |
| | TNA | 18.31 | 18.36 | −0.05 |
| | No TNA | No Ct | No Ct | |

The results using candidate GAT primers and TNA (Table 3 B) suggest that the omp1 primers are capable of amplification of both omp1 DNA and omp1 RNA (FIGS. 4A-B) and thus fit the criteria for suitability as GAT primers. Further, since the Ct for the RT-PCR is 4.92 cycles ahead of the Ct of the PCR this suggests there are many copies of RNA per omp1 DNA gene copy, in the TNA sample. This is also supported by the results using omp1 primers on RNA (FIG. 4A), where there was a large Ct difference of 11.51 observed between the RT-PCR and PCR results, reflecting strong amplification of omp1 RNA in purified RNA samples and only a very late Ct detected for the PCR which is most likely due to small amounts of contaminating DNA in the RNA preparation.

The results using candidate NED primers and TNA (Table 3 B) suggest that the InfAIGR primers are capable of amplification of the infA intergenic DNA sequence (FIG. 4D). Further, since the Ct for the RT-PCR the PCR are very similar (ΔCt–0.05) this demonstrates that these NED primers do not amplify additional RNA sequence in the TNA consistent with a lack of RNA transcription associated with this sequence. As such, these primers fit the criteria for suitability as NED primers. This is also supported by the results using InfAIGR primers on RNA (FIG. 4C), where only late Ct values are generated, which are similar for PCR and RT-PCR, and as before, likely to merely represent amplicons generated from contaminating DNA in the RNA preparation.

This example provides a method which is suitable for screening candidate sequences for use as GAT primers or for use as NED primers. Further, the example shows evidence of contaminating DNA in a purified RNA preparation, despite performing additional DNase digestion procedure during extraction. The observation highlights the need for improved methods, such as VITA PCR, as it is most likely contaminating DNA is the source of at least some false positives observed when amplification of RNA is used as a measure of cell viability in specimens, including clinical specimens. Previous studies have shown that detection of either RNA (or DNA) per sec is not a reliable measure of clearance of *Chlamydia trachomatis*

Example 4—Analysis of GAT and NED in Untreated and Treated Cells by VITA PCR

The following example estimates levels of NED and GAT in TNA samples extracted from HEp-2 cells infected with *Chlamydia trachomatis* (serovar D). TNA was extracted from cells which were not incubated with antibiotic (untreated, viable cells), and from cells incubated with antibiotic at a concentration eight times below the MIC (<MIC), at the MIC (MIC) or at 8 times greater than the MIC (>MIC), as described in example 1, Treatment Protocol A (1.1.1). *Chlamydia* DNA and RNA (GAT) was amplified by RT-PCR using primers targeting the omp1 gene and its transcripts. *Chlamydia* DNA only (NED) was co-amplified in the same RT-PCR using primers targeting a region of genomic DNA, designated infAIGR, which is not transcribed. The Ct values for GAT and NED were determined.

4.1 Partzyme Oligonucleotides

Partzymes were designed to assemble into an active MNAzymes when they bound to amplicons generated by amplification of both the omp1 gene and omp1 transcripts. Once assembled, this MNAzyme could cleave the reporter substrate Sub2-FB. A second pair of partzymes was designed to assemble into an active MNAzymes when bound to amplicons generated by amplification of an non-transcribed region denoted infA_IGR. Once assembled, this MNAzyme could cleave the reporter substrate Sub72-A1B. The sequences of Partzyme A and Partzyme B are listed below, from 5' to 3'. Bases in bold hybridize with the target, underlined bases form part of the catalytic core in the assembled MNAzyme and bases in italic refer to sequence which hybridizes to the substrate.

```
Partzyme A for GAT omp1_A4/2-P
                                      SEQ ID NO: 1
TGGTCTCGAGCATTGAACGAACAACGAGAGGAAACCTT/3Phos/

Partzyme B for GAT omp1_B5/2-P
                                      SEQ ID NO: 2
TGCCCAGGGAGGCTAGCTCATGTTCTCGATTAAGGCTG/3Phos/

Partzyme A for NED CTinfAIGR_A4/72-P
                                      SEQ ID NO: 8
TCGACTAAACAGAAAATGTCAAAACAACGAGAGGCGTGAT/3Phos/

Partzyme B for NED CTinfAIGR_B5/72-P
                                      SEQ ID NO: 9
CTGGGAGGAGAGGCTAGCTCAACTTGTCAAAAAACAGAAGG/3Phos/
```

4.2 Reporter Substrates

In the current example, two different reporter substrates were used, each labelled with distinct fluorophores. Sub2-FB was end-labelled at the 5' end with 6-FAM and IABkFQ at the 3' end, and its cleavage was monitored at 516 nm with excitation at 492 nm. Sub72-A1B was labelled with ATTO™ Rho101 at the 5' end and with IAbRQSp at the 3' end, and its cleavage A1B was monitored at 609 nm with excitation at 592 nm. The reporter substrate for this example is shown below with the sequence, 5' to 3'. The lower case bases represent RNA and the upper case bases represent DNA.

```
Sub2-FB for GAT
                                      SEQ ID NO: 3
AAGGTTTCCTCguCCCTGGGCA Sub72-A1B for NED
                                      SEQ ID NO: 11
ATCACGCCTCguCTCCTCCCAG
```

4.3 PCR Primers for Amplification of the Omp1 Gene and Transcripts

In vitro amplification of TNA template extracted from cells infected with *Chlamydia trachomatis* was performed using the primers listed below. The Forward and Reverse primers were used to amplified omp1 RNA and DNA (GAT) and inf_AGR DNA (NED) by RT-PCR. All sequences are written 5' to 3'.

```
Forward primer for GAT 5omp1:
                                      SEQ ID NO: 4
CTTCTTCCTGGGACGAACG Reverse primer for GAT 3omp1:
                                      SEQ ID NO: 5
TGGCCTGAGGAATGTCTTGC Forward primer for NED 5CTinfAIGR_2
                                      SEQ ID NO: 12
GAGAGAGTGATTATATCGACTAA Reverse primer for NED 3CTinfAIGR_1
                                      SEQ ID NO: 13
CAAGAGAGAATGTCAAAAGATAC
```

4.4 Preparation of TNA

RNA and DNA (TNA) were co-extracted from *Chlamydia trachomatis* (serovar D) which had been cultured in HEp-2 cells as per example 1 (1.1 Culture, 1.1.1 Treatment Protocol A). Extraction was performed as a LLE technique, using phenol:chloroform:isoamyl, also described in example 1 (1.3 Total Nucleic Acid (TNA) extraction, 1.3.1 Extraction Protocol A).

4.5 Reaction Components

All reactions contained 40 nM of each Forward primer, 200 nM of each Reverse primer, 200 nM of each partzyme A, 200 nM of each partzyme B, 200 nM of each substrate, 1× SensiFAST Probe No-ROX Mix (Bioline), 2 mM MgCl$_2$ (Bioline), 0.2 U/μL RiboSafe RNase Inhibitor (Bioline), 0.2 μL of Reverse Transcriptase enzyme (Bioline) and nuclease free water (Ambion) in a total volume of 20 μL. All reactions were performed in triplicate on a BioRad® CFX96 thermocycler. The cycling parameters were 48° C. for 10 minutes, 95° C. for 2 min, 10 cycles of 95° C. for 5 seconds and 61° C. for 30 seconds (with a 0.5° C. decrease in temperature per cycle), and 30 cycles of 95° C. for 5 seconds and 52° C. for 50 seconds. The reactions contained either 5 μL of TNA template (1/100 dilution) or no target (dH$_2$O).

4.6 Results

Figure 5A:
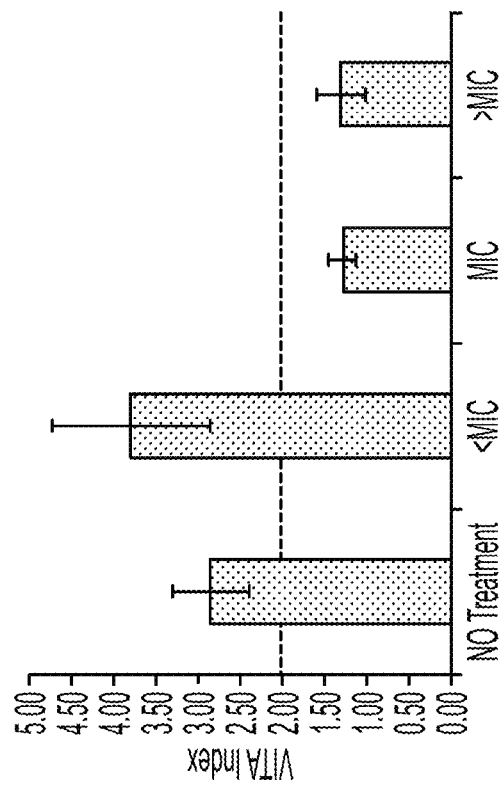
FIGS. 5A-B: Analysis of assays according to embodiments of the present invention. Analysis of *chlamydia* by VITA PCR.

*Chlamydia* DNA and RNA (GAT), or DNA only (NED), were co-amplified in single RT-PCR from TNA extracted from viable untreated cells and from cells incubated with antibiotic at concentrations below (<MIC), equal to (MIC) or above the MIC (>MIC) (FIG. 5 panel i). Table 4 shows the threshold cycle (Ct) values measured for the GAT or NED in each sample. The ΔCt was calculated as the differences between the Ct values of the NED and GAT signals. In turn, the fold change (ratio of GAT to NED) which would theoretically lead to those ΔCt values was estimated as $2^{\Delta Ct}$ (Table 4) and VITA indices were plotted in FIG. 5A. The results were then compared to the viability in each cell population (FIGS. 3A-B).

TABLE 4

Results of VITA PCR (duplex RT-PCR) analysis of TNA from treated and untreated samples

| Sample | Threshold (Ct) GAT | Threshold (Ct) NED | ΔCt NED − GAT | FC = $2^{\Delta Ct}$ | VITA Index |
|---|---|---|---|---|---|
| No Antibiotic | 10.68 | 12.08 | 1.40 | 2.63 | 2.63 |
| <MIC | 12.86 | 14.33 | 1.47 | 2.77 | 2.77 |
| MIC | 21.81 | 22.38 | 0.58 | 1.49 | 1.49 |
| >MIC | 21.87 | 22.47 | 0.60 | 1.51 | 1.51 |
| No TNA | No Ct | No Ct | | | |

Theoretically, if cells were no longer infected with *chlamydia* only very low residual levels of transcripts or their fragments would be detectable. Similarly, only low residual levels of genomic DNA, or fragments of this, would be detectable. The amount of DNA detected could be anticipated to be greater than the amount of RNA since DNA is inherently more stable than RNA. Analysis of results shows that when TNA samples, extracted from samples that were untreated or treated below the MIC, were amplified the Ct value for GAT was lower than the NED (Table 4) consistent with active transcription. For GAT and NED from TNA treated with at the MIC level or above, the differences in Ct value were small (Table 4), indicating little or no transcription. The fold change and VITA Indices were calculated for the four sample types. Since only a single gene and its transcripts were used to calculate the GAT, and only a single non-transcribed region was used to calculate NED, then the fold change and VITA Indices are equal (Table 4).

Previous studies have shown that detection of either DNA or RNA per sec is not a reliable measure of clearance of *Chlamydia trachomatis*. The data from this example demonstrates that the VITA Indices correlate with the measure of viability (PI) for untreated and treated cells as evidenced by comparison of graph in FIG. 5A and FIGS. 3A-B. This example demonstrates that GAT and NED can be measured in a single reaction and the results can be used to calculate VITA Indices which correlate with the observed viability of cells and response to the presence of antibiotics. The example provides a rapid method useful for detection of viability, in this case viability of *chlamydia*. Further it could provide the basis for a Test of Cure (TOC) in patient specimens by determining whether or not an infection has been cleared.

Example 5—Use of Two Regions within a Gene and Corresponding Transcripts to Measure GAT by VITA PCR Using TNA from Untreated and Treated Cells The following example estimates levels of NED and GAT in TNA samples extracted from HEp-2 cells infected with *Chlamydia trachomatis* (serovar D). TNA was extracted from cells which were not incubated with antibiotic (untreated, viable cells), and from cells incubated with antibiotic at a concentration eight times below the MIC (<MIC), at the MIC (MIC) or at 8 times greater than the MIC (>MIC), as described in example 1, Treatment Protocol A (1.2.1). *Chlamydia* DNA and RNA (GAT) was amplified by RT-PCR using primers targeting two different locations of the omp1 gene and its transcripts (GAT1/2). *Chlamydia* DNA only (NED) was co-amplified in the same RT-PCR using primers targeting a region of genomic DNA, designated infAIGR (infA intergenic region), which is not transcribed. The Ct values for GAT1/2 and NED were obtained.

5.1 Partzyme Oligonucleotides

Partzymes were designed to assemble into two active MNAzymes when they bound to amplicons generated by amplification of either the omp1 gene or omp1 transcripts. These two MNAzymes were capable of binding to two different amplicons derived by amplification of two separate regions of omp1 (a GAT1 and a GAT2 region). Once assembled, both MNAzymes could cleave the same reporter substrate Sub2-FB. A third pair of partzymes was designed to assemble into an active MNAzymes when bound to amplicons generated by amplification of an non-transcribed DNA region denoted infA_IGR thus providing a measure of NED. Once assembled, this MNAzyme could cleave the reporter substrate Sub72-A1B. The sequences of partzyme A and Partzyme B for each MNAzyme are listed below, from 5' to 3'. Bases in bold hybridize with the target, underlined bases form part of the catalytic core in the assembled MNAzyme and bases in italic refer to sequence which hybridizes to the substrate.

Partzyme A for GAT1 omp1_A4/2-P

SEQ ID NO: 1

TGGTCTCGAGCATTGAACGAACAACGAGAGGAAACCTT/3Phos/

Partzyme B for GAT1 omp1_B5/2-P

SEQ ID NO: 2

*TGCCCAGGGAGGCTAGCT*CATGTTCTCGATTAAGGCTG/3Phos/

PartzymeA for GAT2 CTomp1_A4/2-P

SEQ ID NO: 14

TTGCACCACTTGGTGTGACGAACAACGAGAGGAAACCTT/3phos/

Partzyme B for GAT2 CTomp1_B5/2-P

SEQ ID NO: 15

*TGCCCAGGGAGGCTAGCT*TATCAGCATGCGTGTGGGTT/3phos/

Partzyme A for NED CTinfAIGR_A4/72-P

SEQ ID NO: 8

TCGACTAAACAGAAAATGTCAAAACAACGAGAGGCGTGAT/3Phos/

Partzyme B for NED CTinfAIGR_B5/72-P

SEQ ID NO: 9

*CTGGGAGGAGAGGCTAGCT*CAACTTGTCAAAAAACAGAAGG/3Phos/

5.2 Reporter Substrates

In the current example, two different reporter substrates were used, each labelled with distinct fluorophores, as per example 4 (4.2 Reporter substrates).

5.3 PCR Primers for Amplification of GAT1, GAT2 and NED

In vitro amplification of TNA template extracted from cells infected with *Chlamydia trachomatis* was performed using the primers listed below. The Forward and Reverse primers were used to amplify two regions of the omp1 gene and transcripts (GAT1 and GAT2) and infA_IGR DNA (NED) by RT-PCR. All sequences are written 5' to 3'.

```
Forward primer for GAT1 5omp1
                               SEQ ID NO: 4
CTTCTTCCTGGGACGAACG Reverse primer for GAT1 3omp1
                               SEQ ID NO: 5
TGGCCTGAGGAATGTCTTGC Forward primer for GAT2 5CTomp1_1
                               SEQ ID NO: 16
TTTCGGCGGAGATCCTTGCGATCC Reverse primer for GAT2 3CTomp1_2
                               SEQ ID NO: 17
CGAAAACAAAGTCACCGTAGTAACC Forward primer for NED 5CTinfAIGR_2
                               SEQ ID NO: 12
GAGAGAGTGATTATATCGACTAA Reverse primer for NED 3CTinfAIGR_1
                               SEQ ID NO: 13
CAAGAGAGAATGTCAAAAGATAC
```

5.4 Preparation of TNA

RNA and DNA (TNA) were co-extracted from *Chlamydia trachomatis* (serovar D) which had been obtained through in-vitro methods, cultured in HEp-2 cells, as described in example 1 (1.1 Culture, 1.1.1 Treatment Protocol A). Extraction was performed as a LLE technique, using phenol:chloroform:isoamyl, also described in example 1 (1.3 Total Nucleic Acid (TNA) extraction, 1.3.1 Extraction Protocol A).

5.5 Reaction Components

All reactions contained 40 nM of each Forward primer, 200 nM of each Reverse primer, 200 nM of each partzyme A, 200 nM of each partzyme B, 400 nM of each substrate SEQ ID NO 3 and 200 nM of substrate SEQ ID NO 11, 1× SensiFAST Probe No-ROX Mix (Bioline), 2 mM $MgCl_2$ (Bioline), 0.2 U/µL RiboSafe RNase Inhibitor (Bioline), 0.2 µL of Reverse Transcriptase enzyme (Bioline) and nuclease free water (Ambion) in a total volume of 20 µL. All reactions were performed in triplicate on a BioRad® CFX96 thermocycler. The cycling parameters were 48° C. for 10 minutes, 95° C. for 2 min, 10 cycles of 95° C. for 5 seconds and 61° C. for 30 seconds (with a 0.5° C. decrease in temperature per cycle), and 30 cycles of 95° C. for 5 seconds and 52° C. for 50 seconds. The reactions contained either 5 µL of TNA template (1/100 dilution) or no target ($dH_2O$).

5.6 Results

Figure 5B:
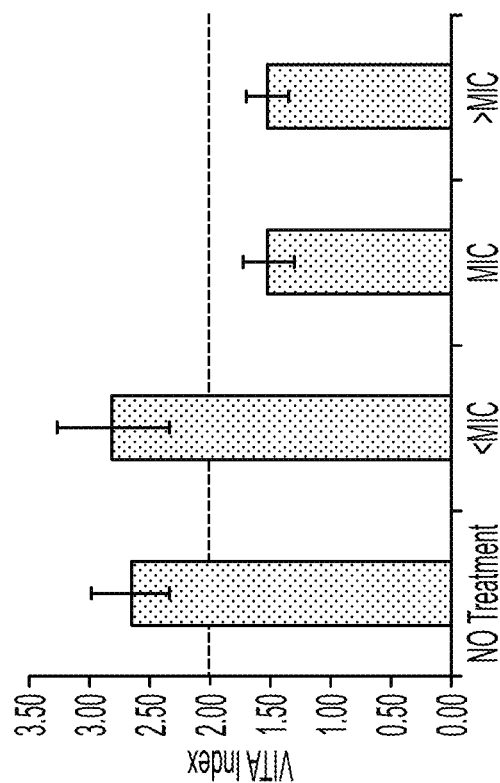

*Chlamydia* DNA and RNA from 2 regions within the omp1 gene and transcripts (GAT1 and GAT2), and one NED region, were co-amplified in single RT-PCR from TNA extracted from viable untreated cells and from cells incubated with antibiotic at concentrations below (<MIC), equal to (MIC) or above the MIC (>MIC) (FIG. 5B). Table shows the threshold cycle (Ct) values measured for NED, and for the combined signals from GAT1 and GAT2 (GAT1/2), in each sample. The ΔCt was calculated as the differences between the Ct values of the NED and GAT1/2. In turn, the fold change (ratio of GAT to NED) which would theoretically lead to those ΔCt values was estimated as $2^{\Delta Ct}$ and shown in Table 5. The VITA Indices were calculated by dividing the FC by the TR, in this instance 2. The results were then compared to the viability in each cell population.

TABLE 5

Results of triplex RT-PCR analysis of TNA from treated and untreated samples

| Sample | Threshold (Ct) | | ΔCt | FC | TR 2×GAT/ 1×NED | VITA Index |
|---|---|---|---|---|---|---|
| | GAT1/2 | NED | | | | |
| No Antibiotic | 9.23 | 11.71 | 2.48 | 5.57 | 2 | 2.79 |
| <MIC | 11.30 | 14.17 | 2.87 | 7.32 | 2 | 3.66 |
| MIC | 20.83 | 22.15 | 1.32 | 2.49 | 2 | 1.25 |
| >MIC | 20.83 | 22.16 | 1.33 | 2.52 | 2 | 1.26 |
| No TNA | No Ct | No Ct | | | | |

Analysis of results shows that when TNA samples, extracted from untreated or treated samples below the MIC, were amplified the Ct value for GAT1/2 was lower than the NED (Table 5) consistent with active transcription. For GAT1/2 and NED from TNA treated with at the MIC level or above, the differences in Ct value were small (Table 5) indicating little or no transcription. The fold change and VITA Indices were calculated for the four sample types. Since two genes and their transcripts were used to calculate the GAT1/2, and only a single non-transcribed region was used to calculate NED, then the fold change is divided by the TR to calculate the VITA Indices (Table 5).

The ability to incorporate multiple primers sets capable of amplifying both DNA and its associated RNA transcripts is in fact highly desirable, as specific genes may only be expressed during certain stages in the development cycle of, for example, bacteria. An assay containing multiple genes expressed, preferably at high levels under different conditions, could ensure expression will consistently be detectable in desperate conditions.

Example 6—Use of VITA PCR on Clinical Specimens

The following example estimates levels of GAT relative to NED in a clinical sample. The urine sample was obtained from a symptomatic patient with successive treatment failures to the first line antibiotic azithromycin. TNA was extracted from the sample and tested alongside reference material extracted from HEp-2 cells infected with *Chlamydia trachomatis* (serovar D) confirmed to be alive/viable (Positive reference) or dead (Negative reference). *Chlamydia* DNA and RNA was amplified by RT-PCR using primers targeting two different locations of the omp1 gene and its transcripts to measure GAT. Another region of *Chlamydia* DNA was co-amplified in the same RT-PCR using primers targeting a region of genomic DNA which is not transcribed to measure NED. The levels of GAT and NED were determined and used to calculate the VITA Indices.

6.1 VITA PCR Analysis of GAT1, GAT2 and NED

Partzyme oligonucleotides, Reporter substrates and PCR primers used for amplification and detection of GAT1, GAT2 and NED were as per example 5 (5.1, 5.2 and 5.3 respectively).

6.2 Preparation of TNA

Clinical Sample:

RNA and DNA (TNA) were co-extracted from a clinical specimen of urine, that had been obtained from a patient with successive treatment failure to first line antibiotic treatment. A total of 8 mL of urine was pelleted, followed by extraction of nucleic acids, performed using the FireMonkey PuriSpin extraction kit, as described in example 1 (1.3 Total Nucleic Acid (TNA) extraction, 1.3.2 Extraction Protocol B), following the manufacturer's instructions for the simultaneous extraction of both DNA and RNA.

Reference Material:

RNA and DNA (TNA) were co-extracted from *Chlamydia trachomatis* (serovar D) which had been obtained through in-vitro methods, cultured in HEp-2 cells, treated with high dose of azithromycin antibiotic (0.512 μL/mL) and confirmed to be "Dead" or Not treated and confirmed to be "Alive", as described in example 1. The viability status of these reference samples had been confirmed through Immunofluorescence staining. Extraction was performed as a liquid-liquid extraction (LLE) technique, using phenol:chloroform:isoamyl, also described in example 1, (1.3 Total Nucleic Acid (TNA) extraction, 1.3.1 Extraction Protocol A)

6.3 Reaction Components

The RT-PCR conditions used were as described in Example 5 (5.5) with the following modifications; 0.1 μL of Reverse Transcriptase enzyme (Bioline) was added in a total reaction volume of 10 μL, which contained either 2.5 μL of TNA extracted from clinical sample (neat), 2.5 μL of each reference TNA sample (1/100 dilution) or no target (dH$_2$O).

6.4 Results

Figure 6B:
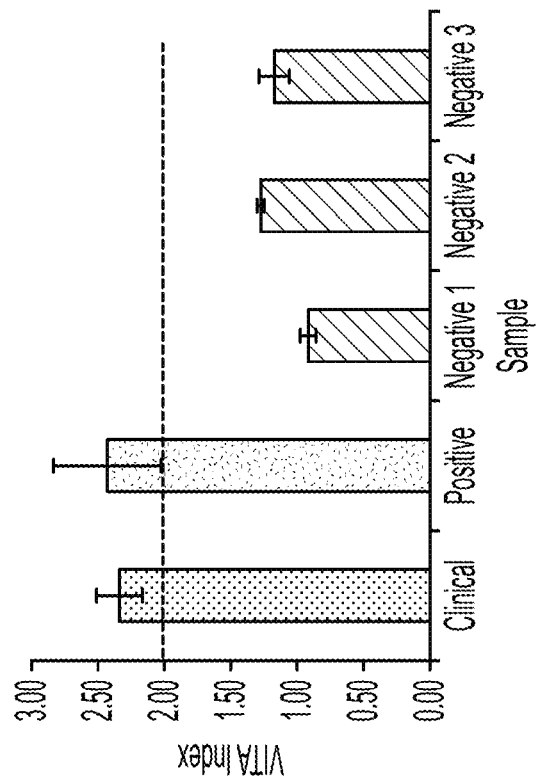
FIGS. 6A-B: Assay and analysis according to an embodiment of the present invention. Analysis of *chlamydia* VITA PCR from a patient urine sample.
Figure 6A:
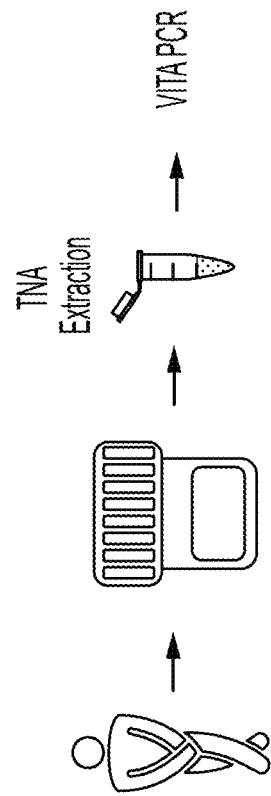

*Chlamydia* DNA and RNA from 2 regions within the omp1 gene and transcripts (GAT1 and GAT2), and one NED region, were co-amplified and detected in single RT-PCR from TNA extracted from a clinical sample of urine (FIG. 6A). Amplification of the clinical sample was compared to reference samples derived from *chlamydia* cultures, either "Alive CT" (samples not treated) or "Dead CT" (treated with high doses of azithromycin) (FIG. 6B). The ΔCt was calculated as the differences between the Ct values of the NED and GAT1/2 signals. In turn, the fold change (difference between the GAT1/2 and NED) which would theoretically lead to those ΔCt values was estimated as $2^{\Delta Ct}$ and shown in Table 6.

It would be predicted that the clinical sample, being derived from a symptomatic patient would contain viable bacteria. In turn this expectedly would result in a similar VITA Index between the clinical sample and the Alive CT reference (Positive), since both would contain higher levels of transcript present.

Analysis of results shows that when the clinical sample, extracted from urine, was amplified the Ct value for GAT1/2 was lower than the NED (Table 6). This is consistent with active transcription and similar to that observed with the reference sample, Alive CT (positive) (Table 6). For all three Dead CT reference samples (Negative 1-3), the Ct values for GAT1/2 and NED were more similar (Table 6). The ΔCt, fold change and VITA Index were calculated for all the samples (Table 6). Since two genes and their transcripts were used to calculate the GAT1/2, and only a single non-transcribed region was used to calculate NED, then the fold change is double that of the VITA Indices (Table 6). Comparison of VITA indices of the clinical sample and the Alive CT demonstrated no difference, correlating with detection of a viable population (FIG. 6 panel ii). Contrary, comparison of VITA indices of the clinical sample and Dead CT samples, demonstrated a difference in the VITA indices. These were higher for the clinical sample than the dead CT samples (FIG. 6B) consistent with decreased or no transcriptional activity in the Dead CT samples which had been treated with high dose of azithromycin and confirmed to not be viable.

The data from this example demonstrated that the GAT1/2 and NED can be measured in a single reaction and results of this used to calculate VITA indices. The comparison between VITA indices of the clinical sample and those of the reference material, demonstrated an accurate call on viability of cells in the clinical sample. This indicates the positive performance of the technology on clinical specimens and it's applicability in a clinical setting. The ability to differentiate between dead and alive cells could have application in determining whether a patient has successfully cleared an infection or not following treatment with antibiotics. The tests could provide an initial diagnosis or a "Test of Cure".

TABLE 6

Results of a triplex RT-PCR analysis of TNA from a clinical specimen in comparison to reference material

| Sample | Threshold (Ct) GAT1/2 | NED | ΔCt NED − GAT | FC | TR 2xGAT/ 1xNED | VITA Index |
|---|---|---|---|---|---|---|
| Clinical sample | 14.33 | 16.56 | 2.23 | 4.86 | 2 | 2.34 |
| Positive (Alive CT) | 9.16 | 11.44 | 2.28 | 4.68 | 2 | 2.43 |
| Negative 1 (Dead CT 1) | 20.96 | 21.83 | 0.88 | 1.83 | 2 | 0.92 |
| Negative 2 (Dead CT 1) | 22.38 | 23.73 | 1.35 | 2.55 | 2 | 1.27 |
| Negative 3 (Dead CT 1) | 21.72 | 22.95 | 1.23 | 2.35 | 2 | 1.17 |
| No TNA | No Ct | No Ct | | | | |

Example 7—Antibiotic Susceptibility Testing Using VITA PCR

The following example estimates the change of GAT levels in TNA samples, extracted from HEp-2 cells infected with *Chlamydia trachomatis* (serovar D). TNA was extracted from cells, which at an exponential growth phase, 24 hours post infection, were either treated with antibiotic at the MIC or not treated (control), as described in example 1, Treatment B (1.1.2). *Chlamydia* DNA and RNA was amplified by RT-PCR using primers targeting two different locations of the omp1 gene and its transcripts to measure GAT. Another region of *Chlamydia* DNA was co-amplified in the same RT-PCR using primers targeting a region of genomic DNA which is not transcribed to measure NED. The levels of GAT and NED were estimated and used to calculate VITA Index.

7.1 VITA PCR Analysis of GAT1, GAT2 and NED

Partzyme oligonucleotides, Reporter substrates and PCR primers used for amplification and detection of GAT1, GAT2 and NED were as per example 5 (5.1, 5.2 and 5.3 respectively). The RT-PCR reaction conditions used were as described in Example 5 (5.5). These reactions contained either 5 μL of TNA template (1/1000 dilution) or no target (dH$_2$O).

7.2 Preparation of TNA

RNA and DNA (TNA) were co-extracted from *Chlamydia trachomatis* (serovar D) which had been cultured in HEp-2 cells, as described in example 1 (1.1 Culture, 1.1.2 Treatment Protocol B). Extraction was performed as a LLE technique, using phenol:chloroform:isoamyl, also described in example 1 (1.3 Total Nucleic Acid (TNA) extraction, 1.3.1 Extraction Protocol A) with the following modification; cell debris pelleting step was not performed during extraction of the samples in this example.

7.3 Results

*Chlamydia* DNA and RNA from 2 regions within the omp1 gene and transcripts (GAT1 and GAT2), and one NED region, were co-amplified and detected in single RT-PCR from TNA extracted from *chlamydia* cultures. These cultures were treated with antibiotic or left untreated (control) at an exponential growth phase and harvested at 1 and 6 hours post treatment (FIG. 7A). Table 4 shows the threshold cycle (Ct) values measured for the GAT1/2 and NED in each sample. The ΔCt was calculated as the differences between the Ct values of the NED and GAT1/2 signals. In turn, the fold change (difference between the GAT1/2 and NED) which would theoretically lead to those ΔCt values was estimated as $2^{\Delta Ct}$ and shown in Table 7. The results were then compared between no treatment reactions (control) and those treated with antibiotic at each time point (FIG. 7B).

It would be predicted that cells susceptible to antibiotic treatment would have a decrease in levels of transcription, as the presence of antibiotic would be anticipated to disrupt the normal functioning of the cells. In turn this would result in a decrease in the VITA Index of these cells compared to control (non-treated cells).

Analysis of results shows that when TNA samples, extracted from untreated and treated groups, were amplified the Ct value for GAT1/2 was lower than the NED (Table 7). This is consistent with active transcription in all four samples. The fold change and VITA Indices were calculated for the samples and different time points post treatment (Table 7). Since two genes and their transcripts were used to calculate the GAT1/2, and only a single un-transcribed region was used to calculate NED, then the fold change is double that of the VITA Indices (Table 7). Comparison of VITA indices of the untreated and treated samples, at both time points, demonstrated a difference in the VITA indices for treated samples, being lower than untreated samples (FIG. B) consistent with decreased transcriptional activity in the presence of antibiotic. The ΔVITA Ratio is calculated by dividing the VITA Index (no antibiotic) by the VITA Index with antibiotic.

The data from this example demonstrates that the GAT1/2 and NED can be measured in a single reaction and results of this used to calculate VITA indices. The comparison between VITA indices of treated and untreated cells, calculated as ΔVITA ratio, demonstrated a response to the presence of antibiotic. This indicates antibiotic susceptibility of the cells. Further, it shows this susceptibility can be ascertained at various time points including at 1 h or 6 h post treatment.

TABLE 7

Results of a triplex RT-PCR analysis of TNA from treated and untreated samples, harvested at different time points post treatment (PT)

| | | Threshold (Ct) | | | | VITA | ΔVITA |
|---|---|---|---|---|---|---|---|
| | Sample | GAT1/2 | NED | ΔCt | FC | Index | A/B |
| 1 h PT | A No Antibiotic | 12.95 | 18.39 | 5.44 | 43.51 | 21.76 | 3.77 |
| | B Plus Antibiotic | 11.76 | 15.29 | 3.53 | 11.55 | 5.78 | |
| 6 h PT | A No Antibiotic | 10.88 | 16.81 | 5.93 | 60.83 | 30.41 | 2.12 |
| | B Plus Antibiotic | 12.69 | 17.53 | 4.84 | 28.71 | 14.35 | |

Example 8—Antibiotic Susceptibility Testing with Azithromycin Using VITA PCR with Shorter Incubation Time The following example estimates the change of GAT levels relative to NED in TNA samples extracted from HEp-2 cells which had been infected with *Chlamydia trachomatis* (serovar D). TNA was extracted from cells, which had been either treated with antibiotic at the MIC, or not treated (control), at 24 hours post infection whilst in an exponential growth phase. Treatment was as described in example 1, Treatment B (1.1.2) using Azithromycin (0.128 µg/mL). To obtain a GAT measure, *Chlamydia* DNA and RNA were amplified by RT-PCR using primers targeting two different locations of the omp1 gene and its transcripts. To measure NED, another region of *Chlamydia* DNA was co-amplified in the same RT-PCR using primers targeting a region of genomic DNA which is not transcribed. The levels of GAT and NED were estimated and used to calculate VITA Index. Further to this the VITA Indices of treated and untreated samples were used to calculate the ΔVITA ratio.

8.1 VITA PCR Analysis of GAT1, GAT2 and NED

Partzyme oligonucleotides, Reporter substrates and PCR primers used for amplification and detection of GAT1, GAT2 and NED were as per example 5 (5.1, 5.2 and 5.3 respectively). The RT-PCR conditions used were as described in Example 5 (5.5) and reactions contained either 5 µL of TNA template (1/1000 dilution) or no target (dH$_2$O).

8.2 Preparation of TNA

RNA and DNA (TNA) were co-extracted from *Chlamydia trachomatis* (serovar D) which had been cultured in HEp-2 cells, as described in example 1 (1.1 Culture, 1.1.2 Treatment Protocol B). Extraction was performed as a LLE technique, using phenol:chloroform:isoamyl, also described in example 1 (1.3 Total Nucleic Acid (TNA) extraction, 1.3.1 Extraction Protocol A) with the following modification; cell debris pelleting step was not performed during extraction of the samples in this example.

8.3 Results

*Chlamydia* DNA and RNA from 2 regions within the omp gene and transcripts (GAT1 and GAT2), and one NED region, were co-amplified and detected in single RT-PCR from TNA extracted from *chlamydia* cultures. These cultures were treated with antibiotic or left untreated (control) at an exponential growth phase and harvested at 30 min or 1 hour post treatment with 0.128 µg/mL of Azithromycin (FIG. 7A). Table 8 shows the threshold cycle (Ct) values measured for the GAT1/2 and NED in each sample. The ΔCt was calculated as the differences between the Ct values of the NED and GAT1/2 signals. In turn, the fold change (difference between the GAT1/2 and NED) which would theoretically lead to those ΔCt values was estimated as $2^{\Delta Ct}$ and shown in Table 8. The results were then compared between no treatment reactions (control) and those treated with antibiotic at each time point (FIG. 7C).

TABLE 8

Results of a triplex RT-PCR analysis of TNA from treated and untreated samples, harvested at different time points post treatment (PT)

| | | Threshold (Ct) | | | Fold | VITA | ΔVITA Ratio |
|---|---|---|---|---|---|---|---|
| | Sample | GAT1/2 | NED | ΔCt | Change | Index | A/B |
| 30 min PT | A No Antibiotic | 14.14 | 22.18 | 8.04 | 263.20 | 133.44 | 1.4 |
| | B Plus Antibiotic | 14.00 | 21.55 | 7.55 | 187.40 | 94 | |
| 1 h PT | A No Antibiotic | 14.18 | 22.11 | 7.93 | 243.88 | 121.67 | 2.5 |
| | B Plus Antibiotic | 13.79 | 20.41 | 6.62 | 98.36 | 49.20 | |

Analysis of results shows that when TNA samples, extracted from untreated and treated groups, were amplified the Ct value for GAT1/2 was lower than the NED (Table 8) indicating there was active transcription in all samples. The fold change and VITA Indices were calculated for all samples at all time points post treatment (Table 8). Since two genes and their transcripts were used to calculate the GAT1/2, and only a single un-transcribed region was used to calculate NED, then the fold change is double that of the VITA Indices (Table 8). Comparison of VITA indices, between the untreated and treated samples at each time point, demonstrated a difference in the VITA indices (FIG. 7C). This is consistent with a disruption to the transcription activity of cells in the presence of antibiotic. The ΔVITA Ratio is calculated by dividing the VITA Index (no antibiotic) by the VITA Index with antibiotic.

As per example 7, the data from this example demonstrates that the GAT1/2 and NED can be measured in a single reaction and results of this used to calculate VITA indices. A response to the presence of antibiotic was detected, through comparison between VITA indices of treated and untreated cells and calculated as ΔVITA Ratio. This reflects the antibiotic susceptibility of the cells. It further demonstrates that susceptibility can be established at various time points including at 30 min or 1 h post antibiotic treatment with Azithromycin.

Example 9—Antibiotic Susceptibility Testing with Rifampicin VITA PCR and Shorter Incubation Time The following example estimates the change of GAT levels relative to NED in TNA samples extracted from HEp-2 cells which had been infected with *Chlamydia trachomatis* strain 1 and strain 5 (serovar D lab strain and serovar L2 strain resistant to rifampicin respectively). TNA was extracted from cells, which had been either treated with the antibiotic Rifampicin at a concentration of 0.256 µg/mL, or not treated (control), at 20 hours post infection whilst in an exponential growth phase. Treatment was as described in example 1, Treatment C (1.1.3). To obtain a measure GAT, *Chlamydia* DNA and RNA was amplified by RT-PCR using primers targeting two different locations of the omp1 gene and its transcripts. To measure NED, another region of *Chlamydia* DNA was co-amplified in the same RT-PCR using primers targeting a region of genomic DNA which is not transcribed. The levels of GAT and NED were estimated and used to calculate VITA Index. Further to this the VITA Indices of treated and untreated samples were used to calculate the ΔVITA Ratio.

9.1 VITA PCR Analysis of GAT1, GAT2 and NED

Partzymes were designed to assemble into two active MNAzymes when they bound to amplicons generated by amplification of either the omp1 gene or omp1 transcripts. These two MNAzymes were capable of binding to two different amplicons derived by amplification of two separate regions of omp1 (a GAT1 and a GAT2 region). Once assembled, both MNAzymes could cleave the same reporter substrate Sub102(20)-FB. A third pair of partzymes was designed to assemble into an active MNAzymes when bound to amplicons generated by amplification of a non-transcribed DNA region denoted infA_IGR thus providing a measure of NED. Once assembled, this MNAzyme could cleave the reporter substrate Sub72-A1B. The sequences of Partzyme A and Partzyme B for each MNAzyme are listed below, from 5' to 3'. Bases in bold hybridize with the target, underlined bases form part of the catalytic core in the assembled MNAzyme and bases in italic refer to sequence which hybridizes to the substrate.

Partzyme A for GAT1 CTomp1T_3A4/102-P
SEQ ID NO: 18
ATTGAACGACATGTTCTCGATTAAAACAACGA*GGGACGTCGA*/3Phos/

Partzyme B for GAT1 CTomp1T_3B5/102-P
SEQ ID NO: 19
*CGGTAGAGG*AGGCTAGCTGGCTGCTTTTACTTGCAAGACA/3Phos/

PartzymeA for GAT2 CTomp1L_A4/102-P
SEQ ID NO: 20
CTTGCACCACTTGGTGTGACGACAACGA*GGGACGTCGA*/3phos/

Partzyme B for GAT2 CTomp1L_B5/102-P
SEQ ID NO: 21
*CGGTAGAGG*AGGCTAGCTCTATCAGCATGCGTGTGGGTTA/3phos/

Partzyme A for NED CTinfAIGR_A4/72-P
SEQ ID NO: 8
TCGACTAAACAGAAAATGTCAAAACAACGA*GAGGCGTGAT*/3Phos/

Partzyme B for NED CTinfAIGR_B5/72-P
SEQ ID NO: 9
*CTGGGAGGA*GAGGCTAGCTCAACTTGTCAAAAAACAGAAGG/3Phos/

9.2 Reporter Substrates

In the current example, two different reporter substrates were used, each labelled with distinct fluorophores. Sub102(20)-FB was end-labelled at the 5' end with 6-FAM and with IABkFQ at the 3' end, and its cleavage was monitored at 516 nm with excitation at 492 nm. Sub72-A1B was labelled with ATTO™ Rho101 at the 5' end and with IAbRQSp at the 3' end, and its cleavage was monitored at 609 nm with excitation at 592 nm. The reporter substrates for this example are shown below with the sequence, 5' to 3'. The lower case bases represent RNA and the upper case bases represent DNA.

for GAT1 and GAT Sub102(20)-FB
SEQ ID NO: 10
TCGACGTCCCguCCTCTACCG for NED Sub72-A1B
SEQ ID NO: 11
ATCACGCCTCguCTCCTCCCAG 9.3 PCR Primers for Amplification of GAT1, GAT2 and NED In vitro amplification of TNA template extracted from cells infected with *Chlamydia trachomatis* was performed using the primers listed below. The Forward and Reverse primers were used to amplify two regions of the omp1 gene and transcripts (GAT1 and GAT2) and infA_IGR DNA (NED) by RT-PCR. All sequences are written 5' to 3'.

Forward primer for GAT1 5omp1
SEQ ID NO: 4
CTTCTTCCTGGGACGAACG

Reverse primer for GAT1 3omp1_2
SEQ ID NO: 22
CAATTAATGGCCTGAGGAATGTC

Forward primer for GAT2 5CTomp1_1
SEQ ID NO: 16
TTTCGGCGGAGATCCTTGCGATCC

Reverse primer for GAT2 3CTomp1_2
SEQ ID NO: 17
CGAAAACAAAGTCACCGTAGTAACC

```
-continued
Forward primer for NED 5CTinfAIGR_2
                             SEQ ID NO: 12
GAGAGAGTGATTATATCGACTAA Reverse primer for NED 3CTinfAIGR_3
                             SEQ ID NO: 23
GCAAAAACTCAAGAGAGAATGTC
```

9.4 Preparation of TNA

RNA and DNA (TNA) were co-extracted from *Chlamydia trachomatis* (serovar D) which had been cultured in HEp-2 cells, as described in example 1 (1.1 Culture, 1.1.3 Treatment Protocol C). Extraction was performed using the FireMonkey PuriSpin Extraction kit, as defined in example 1 (1.3 Total Nucleic Acid (TNA) extraction, 1.3.2 Extraction Protocol B) and following manufacturer's instructions for simultaneous extraction of DNA and RNA.

9.5 Reaction Components

All reactions contained 40 nM of each Forward primer, 200 nM of each Reverse primer, 200 nM of each partzyme A, 200 nM of each partzyme B, 400 nM of substrate SEQ ID NO 10 and 200 nm of substrate SEQ ID NO 11, 1× SensiFAST Probe No-ROX Mix (Bioline), 2 mM MgCl$_2$ (Bioline), 0.2 U/µL RiboSafe RNase Inhibitor (Bioline), 0.2 µL of Reverse Transcriptase enzyme (Bioline) and nuclease free water (Ambion) in a total volume of 20 µL. All reactions were performed in triplicate on a BioRad® CFX96 thermocycler. The cycling parameters were 48° C. for 10 minutes, 95° C. for 2 min, 10 cycles of 95° C. for 5 seconds and 61° C. for 30 seconds (with a 0.5° C. decrease in temperature per cycle), and 30 cycles of 95° C. for 5 seconds and 52° C. for 50 seconds. The reactions contained either 5 µL of TNA template (1/1000 dilution) or no target (dH$_2$O).

9.6 Results

Figure 7E:
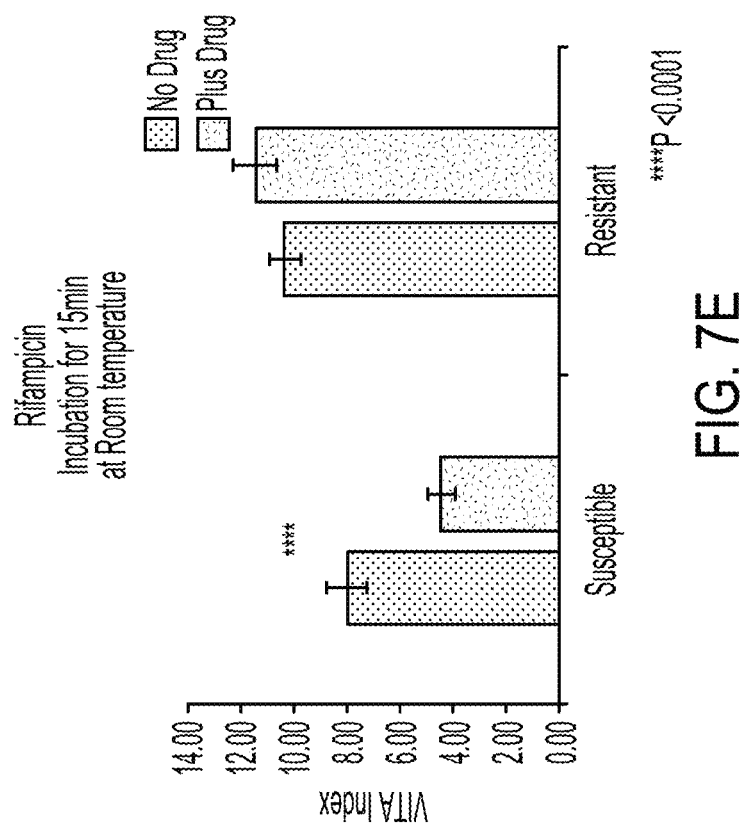
Figure 7D:
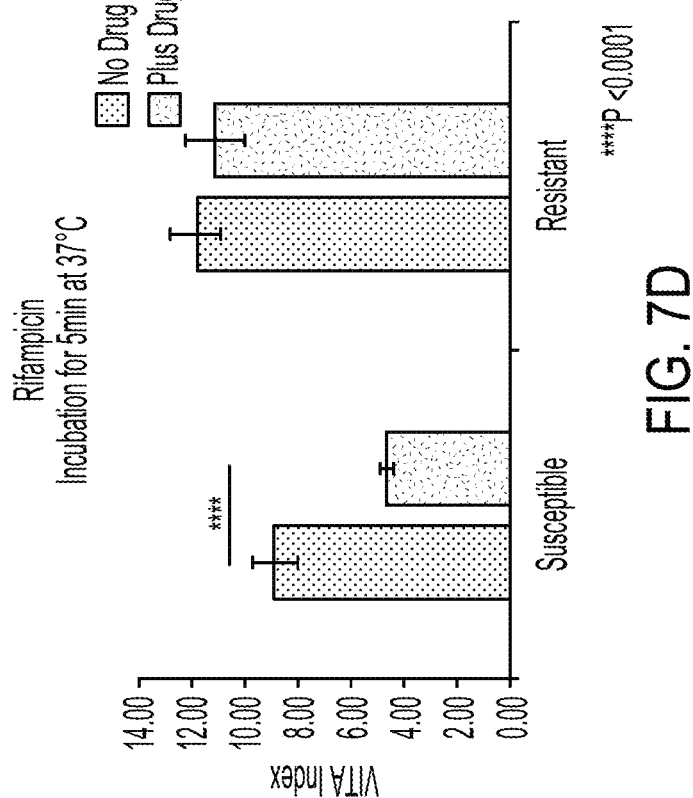

*Chlamydia* DNA and RNA from 2 regions within the omp1 gene and transcripts (GAT1 and GAT2), and one NED region, were co-amplified and detected in single RT-PCR from TNA extracted from chlamydia cultures. These cultures were treated with antibiotic or left untreated (control) at an exponential growth phase. They were incubated for either 5 minutes at 37° C. (FIG. 7D) or 15 minutes at room temperature (FIG. 7E). The antibiotic used for treatment was Rifampicin, at a concentration of 0.256 µg/mL, equivalent to 32 times more than the MIC for susceptible strains and 32 times less than the MIC for resistant strains. Table 9 shows the threshold cycle (Ct) values measured for the GAT1/2 and NED in each sample. The ΔCt was calculated as the differences between the Ct values of the NED and GAT1/2 signals. In turn, the fold change (difference between the GAT1/2 and NED) which would theoretically lead to those ΔCt values was estimated as $2^{\Delta Ct}$ and shown in Table 9. The results were then compared between no treatment reactions (control) and those treated with antibiotic at each time point (FIGS. 7D-E).

TABLE 9

Results of a triplex RT-PCR analysis of TNA from treated and untreated samples, harvested at different time points post treatment (PT) 5 min with incubation at 37° C. with 5% CO$_2$ and 15 minutes with incubation at room temperature.

| Sample | | | Threshold (Ct) | | ΔCt | Fold Change | VITA Index | ΔVITA Ratio A/B | p value |
|---|---|---|---|---|---|---|---|---|---|
| | | | GAT1/2 | NED | | | | | |
| 5 min incubation PT At 37° C. with 5% CO$_2$ | Susceptible strain (strain 1) | A No Antibiotic | 13.96 | 18.11 | 4.16 | 17.81 | 8.91 | 1.90 | <0.0001 **** |
| | | B Plus Antibiotic | 15.07 | 18.30 | 3.23 | 9.37 | 4.69 | | |
| | Resistant strain (strain 5) | A No Antibiotic | 14.75 | 19.32 | 4.58 | 23.86 | 11.91 | 1.07 | 0.2573 |
| | | B Plus Antibiotic | 14.28 | 18.76 | 4.48 | 22.37 | 11.18 | | |
| 15 min incubation PT At room temperature | Susceptible strain (strain 1) | A No Antibiotic | 14.93 | 18.92 | 3.99 | 15.91 | 7.95 | 1.80 | <0.0001 **** |
| | | B Plus Antibiotic | 15.34 | 18.48 | 3.14 | 8.82 | 4.41 | | |
| | Resistant strain (strain 5) | A No Antibiotic | 14.82 | 19.19 | 4.37 | 20.65 | 10.33 | 0.91 | N/A |
| | | B Plus Antibiotic | 14.55 | 19.06 | 4.51 | 22.81 | 11.41 | | |

Analysis of results shows that when TNA samples, extracted from untreated and treated groups, were amplified the Ct value for GAT1/2 was lower than the NED (Table 9) indicating there was active transcription in all samples. The fold change and VITA Indices were calculated for all samples at all time points post treatment (Table 9). Since two genes and their transcripts were used to calculate the GAT1/2, and only a single un-transcribed region was used to calculate NED, then the fold change is double that of the VITA Indices (Table 9). Decreases in VITA indices, between the untreated and treated samples were analysed using the unpaired t-test, at each time point and incubation condition.

Results showed a significant decrease in the VITA indices of the susceptible strain 1 (Table 9, p<0.0001) following 5 minutes incubation with Rifampicin at 37° C. (FIG. 7D). This is consistent with a disruption to the transcription activity of cells in the presence of antibiotic and confirms the susceptibility profile of this particular serovar. Contrastingly, the VITA Index of the resistant strain (strain 5) did not demonstrate a significant difference between treated and untreated samples under these same conditions (Table 9, FIG. 7D) confirming the resistant profile of this particular serovar. In a parallel experiment, a decrease in the VITA indices of replicates of the susceptible strain 1 (Table 9, p<0.0001) was observed following 15 minutes incubation with Rifampicin at room temperature (FIG. 7E). The VITA Index of the resistant strain 5 did not decrease in the presence of Rifamycin under the same conditions, and in fact showed a small increase.

The data from this example demonstrates that the GAT1/2 and NED can be measured in a single reaction and results of this used to calculate VITA indices. A response to the presence of antibiotic was detected, through comparison between VITA indices of treated and untreated cells and calculated as ΔVITA Ratio. This can be used to accurately reflect the antibiotic susceptibility or resistance profiles of cells and further demonstrates that susceptibility can be established after short incubation times. Differentiation between susceptibility and resistance to antibiotics can be detected as early as 5 minutes post antibiotic treatment. It was also demonstrated that the need for incubation at a stable 37° C. is not necessary, with incubation at room temperature correctly distinguishing susceptible and resistant organisms.

Example 10: Antibiotic Susceptibility Testing Using VITA PCR—Dose Dependent Response Using Extraction Protocol A The following example estimates the change of GAT relative to NED in TNA samples, extracted from HEp-2 cells which had been infected with *Chlamydia trachomatis* (serovar D). TNA was extracted from cells, which were either untreated (control) or treated with antibiotic (azithromycin) at varying doses; specifically, at a concentration four times the MIC (0.128 μg/mL), six times the MIC (0.192 μg/mL) and eight times the MIC (0.256 μg/mL). Antibiotic was added at 24 hours post infection when cells were in exponential growth phase, as described in example 1, Treatment D (1.1.4). To measure GAT, chlamydia DNA and RNA was amplified by RT-PCR using primers targeting two different locations of the omp1 gene and its transcripts. To measure NED, another region of *chlamydia* DNA was co-amplified in the same RT-PCR using primers targeting a region of genomic DNA which is not transcribed. The levels of GAT and NED were estimated and used to calculate the VITA Indices. Further to this the VITA Indices of treated and untreated samples were used to calculate the ΔVITA Ratio.

10.1 VITA PCR Analysis of GAT1, GAT2 and NED

Partzyme oligonucleotides, Reporter substrates and PCR primers used for amplification and detection of GAT1, GAT2 and NED were as per example 5 (5.1, 5.2 and 5.3 respectively). The RT-PCR conditions used were as described in Example 5 (5.5) and reactions contained either 5 μL of TNA template (1/1000 dilution) or no target (dH₂O).

10.2 Preparation of TNA

RNA and DNA (TNA) were co-extracted from *Chlamydia trachomatis* (serovar D) which had been cultured in HEp-2 cells, as described in example 1 (1.1 Culture, 1.1.4 Treatment Protocol D). Extraction was performed as a LLE technique, using phenol:chloroform:isoamyl, also described in example 1 (1.3 Total Nucleic Acid (TNA) extraction, 1.3.1 Extraction Protocol A) with the following modification; cell debris pelleting step was not performed during extraction of the samples in this example.

10.3 Results

*Chlamydia* DNA and RNA from 2 regions within the omp1 gene and transcripts (GAT1 and GAT2), and one NED region, were co-amplified and detected in a single RT-PCR using TNA extracted from *chlamydia* cultures. These cultures were treated with serial doses of antibiotic or left untreated (control) during the exponential growth phase and harvested after a 1-hour incubation (FIG. 8A). Table 10 shows the threshold cycle (Ct) values measured for the GAT1/2 and NED in each sample. The ΔCt was calculated as the differences between the Ct values of the NED and GAT1/2 signals. In turn, the fold change (difference between the GAT1/2 and NED) which would theoretically lead to those ΔCt values was estimated as $2^{\Delta Ct}$ and shown in Table 10. The results were then compared between no treatment reactions (control) and those treated with the different doses of antibiotic (FIG. 8B).

TABLE 10

Results of a triplex RT-PCR analysis of TNA from untreated samples and samples treated with serial doses of antibiotic, harvested at 1 h post treatment

| Sample | Threshold (Ct) GAT1/2 | NED | ΔCt | FC | TR 2xGAT/1xNED | VITA Index | ΔVITA Ratio control/treated |
|---|---|---|---|---|---|---|---|
| A No Antibiotic | 12.30 | 20.26 | 7.96 | 249.58 | 2 | 124.87 | |
| B Plus Antibiotic dose 1 | 12.38 | 19.86 | 7.48 | 178.53 | 2 | 89.28 | A/B 1.4 |
| C Plus Antibiotic dose 2 | 12.63 | 19.77 | 7.14 | 141.37 | 2 | 70.74 | A/C 1.8 |
| D Plus Antibiotic dose 3 | 12.20 | 18.05 | 5.85 | 57.81 | 2 | 28.91 | A/D 4.3 |

It was predicted that cells susceptible to antibiotic treatment would have a decrease in levels of transcription in the presence of antibiotic since this would be anticipated to disrupt the normal functioning of the cells. Further, it was predicted that higher doses of antibiotic would lead to greater disruption to normal functioning and consequently transcription levels. This example was performed to demonstrate this and to establish whether the decrease in the VITA Indices of the treated cells correlates to the dose of antibiotic used.

Analysis of results shows that when TNA samples, extracted from untreated and treated groups, were amplified the Ct values for GAT1/2 was lower than the NED (Table 10), consistent with active transcription in all four samples. The fold change and VITA Indices were calculated for each sample (Table 10). Since two gene and transcript regions were used to calculate the GAT1/2, and only a single un-transcribed region was used to calculate NED, then the fold change is double that of the VITA Indices (Table 10). Comparison of VITA indices of the untreated and treated samples demonstrated a difference (FIG. 8B). The difference was significant for untreated (No drug) and treated (Plus drug dose 1) (p=0.0005, using an unpaired t-test). For all treated samples, being not only lower than untreated samples, they were also sequentially lower the higher the dose of antibiotic used during incubation (FIG. 8B. In this experiment there was a correlation between the dose and the decrease the VITA Indices ($R^2$=0.9775, FIG. 8B). This is consistent with a decrease in transcriptional activity in the presence of antibiotic, and the higher the dose of antibiotic given, the greater the disruption to transcriptional activity was observed. The ΔVITA Ratio is calculated by dividing the VITA Index (no antibiotic) by the VITA Index of samples treated with each dose of antibiotic (plus antibiotic dose1, dose 2 and dose 3, Table 10, FIG. 8B.

The data from this example demonstrates that the GAT1/2 and NED can be measured in a single reaction and results of this used to calculate VITA indices. The comparison between VITA indices of treated and untreated cells, calculated as ΔVITA Ratio, demonstrated a response to the presence of antibiotic. That response to antibiotics was also greater when serially higher doses of antibiotic were used, indicating a dose dependent response. This further demonstrated the ability to use VITA Indices to examine whether cells are susceptible to an antibiotic and that a 1-hour incubation can be sufficient to determine this. The response to a drug in a dose dependent manner may find application in drug discovery or drug screening programs Example 11—Antibiotic Susceptibility Testing Using VITA PCR—Dose Dependent Response Using Extraction Protocol B The following example estimates the change of GAT relative to NED in TNA samples, extracted from HEp-2 cells which had been infected with *Chlamydia trachomatis* (serovar D). TNA was extracted from cells, which were either untreated (control) or treated with the antibiotic azithromycin at varying doses; specifically, at a concentration four times the MIC (0.128 µg/mL), six times the MIC (0.192 µg/mL), eight times the MIC (0.256 µg/mL) and sixteen times the MIC (0.512 µg/mL). Antibiotic was added at 20 hours post infection when cells were in exponential growth phase, as described in example 1, Treatment D (1.1.4). To measure GAT, *Chlamydia* DNA and RNA was amplified by RT-PCR using primers targeting two different locations of the omp1 gene and its transcripts. To measure NED, another region of *Chlamydia* DNA was co-amplified in the same RT-PCR using primers targeting a region of genomic DNA which is not transcribed. The levels of GAT and NED were estimated and used to calculate the VITA Indices. Further to this the VITA Indices of treated and untreated samples were used to calculate the ΔVITA Ratio.

11.1 VITA PCR Analysis of GAT1, GAT2 and NED

Partzyme oligonucleotides, Reporter substrates and PCR primers used for amplification and detection of GAT1, GAT2 and NED were as per example 9 (9.1, 9.2 and 9.3 respectively). The RT-PCR conditions used were as described in Example 9 (9.5) and reactions contained either 5 µL of TNA template (1/1000 dilution) or no target ($dH_2O$).

11.2 Preparation of TNA

RNA and DNA (TNA) were co-extracted from *Chlamydia trachomatis* (serovar D) which had been cultured in HEp-2 cells, as described in example 1 (1.1 Culture, 1.1.4 Treatment Protocol D). Extraction was performed using the FireMonkey PuriSpin Extraction kit, as defined in example 1 (1.3 Total Nucleic Acid (TNA) extraction, 1.3.2 Extraction Protocol B) and following manufacturer's instructions for simultaneous extraction of DNA and RNA.

11.3 Results

Co-amplification of *Chlamydia* DNA and RNA from 2 regions (GAT1 and GAT2), and one NED region, were monitored in a single RT-PCR using TNA extracted from *chlamydia* cultures. These cultures were treated with serial doses of antibiotic or left untreated (control) during the exponential growth phase and harvested at 1-hour post treatment (FIG. 8A). Table 11 shows the threshold cycle (Ct) values measured for the GAT1/2 and NED in each sample. The ΔCt was calculated as the differences between the Ct values of the NED and GAT1/2 signals. In turn, the fold change (difference between the GAT1/2 and NED) which would theoretically lead to those ΔCt values was estimated as $2^{\Delta Ct}$ and shown in Table 11. The results were then compared between no treatment reactions (control) and those treated with the different doses of antibiotic (FIG. 8C).

TABLE 11

Results of a triplex RT-PCR analysis of TNA from untreated samples and samples treated with serial doses of antibiotic, with 1 h incubation post treatment

| Sample | Threshold (Ct) GAT1/2 | NED | ΔCt | FC | TR 2xGAT/ 1xNED | VITA Index | ΔVITA Ratio |
|---|---|---|---|---|---|---|---|
| A No Antibiotic | 15.71 | 19.25 | 3.54 | 11.66 | 2 | 5.83 | |
| B Plus Antibiotic dose 1 | 16.08 | 19.24 | 3.16 | 8.94 | 2 | 4.47 | A/B 1.30 |
| C Plus Antibiotic dose 2 | 16.01 | 19.07 | 3.06 | 8.36 | 2 | 4.18 | A/C 1.39 |
| D Plus Antibiotic dose 3 | 16.37 | 19.35 | 2.98 | 7.91 | 2 | 3.95 | A/D 1.47 |
| E Plus Antibiotic dose 4 | 16.56 | 19.31 | 2.74 | 6.70 | 2 | 3.35 | A/E 1.74 |

In the same way as described in example 10, it is expected that cells susceptible to antibiotic treatment would have a reduction in transcription levels as the presence of antibiotic would be anticipated to disrupt the normal functioning of the cells. It is predicted that the disruption caused could correlate to the dose of antibiotic and as such, it would be likely that the higher the dose of antibiotic the greater the disruption to normal functioning, transcription levels and resulting VITA Indices.

Analysis of results shows that when TNA samples, extracted from untreated and treated groups, were amplified the Ct value for GAT1/2 was lower than the NED (Table 11). This is consistent with active transcription in all samples. The fold change and VITA Indices were calculated for the samples (Table 11). The fold change is double that of the VITA Indices (Table 11), since two gene and corresponding transcript regions were used to calculate the GAT1/2, and only a single non-transcribed region was used to calculate NED. Comparison of VITA indices, of the untreated (No Drug) and treated sample (Plus drug dose 1), demonstrated a significant difference (FIG. 8C, p<0.05 generated using an unpaired t-test). All remaining treated samples were also different to the untreated (FIG. 8C). The treated samples displayed VITA Indices that were lower than untreated samples. Further, as the treatment dose increased the VITA Indices decreased (FIG. 8C). This is consistent with a decrease in transcriptional activity in the presence of antibiotic and further evident that the more antibiotic used the greater the disruption to transcriptional activity was observed. This trend also generated a linear correlation ($R^2=0.8325$) between VITA Index and antibiotic dose (FIG. 8C, Table 11). The ΔVITA Ratio is calculated by dividing the VITA Index (no antibiotic) by the VITA Index of samples treated with each dose of antibiotic (plus antibiotic dose1, dose 2, dose 3 and dose 4). The ΔVITA Ratio displayed an increase in value correlating with the increase in antibiotic dose (Table 11).

The data from this example further elucidates that the GAT1/2 and NED can be measured in a single reaction and results of this used to calculate VITA indices. The comparison between VITA indices of treated and untreated cells, calculated as ΔVITA Ratio, demonstrated a response to the presence of antibiotic. The response to antibiotics was linearly correlated with the dose used for treatment, indicating a dose dependent response. This was independent of the extraction method used to obtain the TNA samples. This further established, as seen in example 10, the ability to use VITA Indices to examine whether cells are susceptible or resistant to an antibiotic and that a 1-hour incubation is sufficient. The capacity of the VITA PCR to monitor response to a drug in a dose dependent manner may find application in drug discovery or drug screening programs.

Example 12—Antibiotic Susceptibility Testing with Azithromycin and Doxycycline Using VITA PCR The following example analyses the susceptibility of bacteria to a given drug, by estimation of the change of GAT levels relative to NED in TNA samples. These were then compared between samples treated with antibiotic and not treated (control). Samples were obtained from HEp-2 cells which had been infected with different *Chlamydia trachomatis* strains, known to be susceptible to both drugs tested, Azithromycin and Doxycycline. TNA was extracted from cells, which had been either treated with a single dose of either antibiotic (0.256 µg/mL), or not treated (control) 20 hours post infection whilst in an exponential growth phase and incubated for one hour post-treatment. Treatment was as described in example 1, Treatment E (1.1.5). To obtain a measure GAT, *Chlamydia* DNA and RNA was amplified by RT-PCR using primers targeting two different locations of the omp1 gene and its transcripts. To measure NED, another region of *Chlamydia* DNA was co-amplified in the same RT-PCR using primers targeting a region of genomic DNA which is not transcribed. The levels of GAT and NED were estimated and used to calculate VITA Index. Further to this the VITA Indices of treated and untreated samples were used to calculate the ΔVITA Ratio.

12.1 VITA PCR Analysis of GAT1, GAT2 and NED

Partzyme oligonucleotides, Reporter substrates and PCR primers used for amplification and detection of GAT1, GAT2 and NED were as per example 9 (9.1, 9.2 and 9.3 respectively). The RT-PCR conditions used were as described in Example 9 (9.5) and reactions contained either 5 µL of TNA template (1/1000 dilution) or no target (dH$_2$O).

12.2 Preparation of TNA

RNA and DNA (TNA) were co-extracted from different strains of *Chlamydia trachomatis*, which had been cultured in HEp-2 cells, as described in example 1 (1.1 Culture, 1.1.5 Treatment Protocol E). Extraction was performed using the FireMonkey PuriSpin Extraction kit, as defined in example 1 (1.3 Total Nucleic Acid (TNA) extraction, 1.3.2 Extraction Protocol B) and following manufacturer's instructions for simultaneous extraction of DNA and RNA.

12.3 Results

Figure 9A:
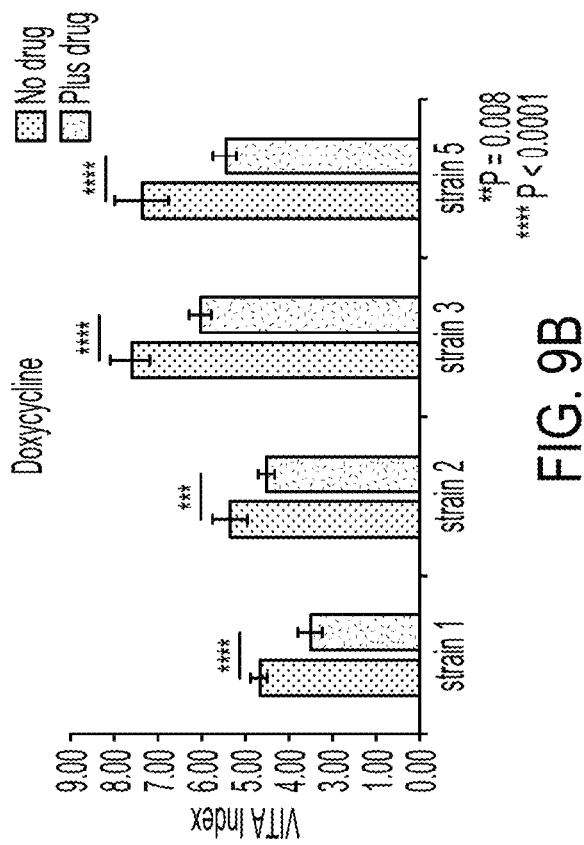
FIGS. 9A-D: Analysis of assays according to embodiments of the present invention. Analysis of *chlamydia* by VITA PCR in response to a short incubation with various antibiotics, using TNA extracted from a series of strains previously characterized as either susceptible and resistant to specific antibiotics.
Figure 9B:
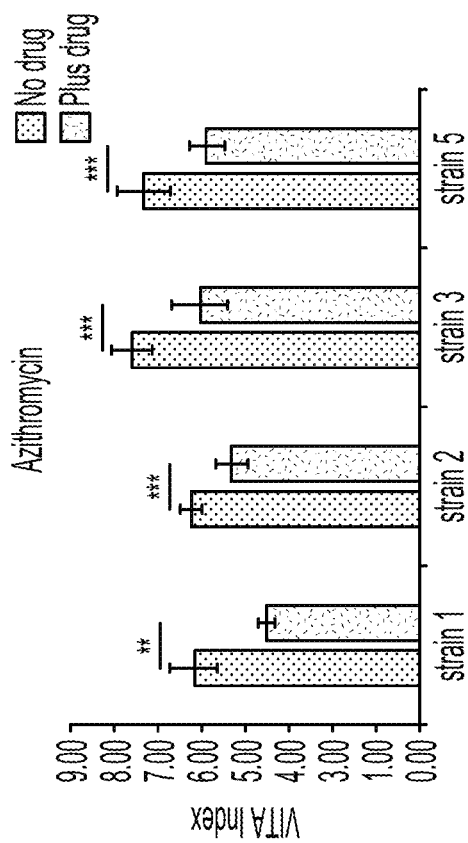

*Chlamydia* DNA and RNA from 2 GAT regions and one NED region, were co-amplified and detected in single RT-PCR from TNA extracted from *chlamydia* cultures. These cultures were treated with antibiotic or left untreated (control) at an exponential growth phase and harvested at 1 hour post treatment. Table 12a and 12b display the threshold cycle (Ct) values for each sample (treated or untreated) for each individual strain and antibiotic used for treatment, namely Azithromycin and Doxycycline respectively. The ΔCt was calculated as the differences between the Ct values of the NED and GAT1/2 signals. In turn, the fold change (difference between the GAT1/2 and NED) which would theoretically lead to those ΔCt values was estimated as $2^{\Delta Ct}$ and shown in Table 12a and 12b. The results were then compared between no treatment reactions (control) and those treated with antibiotic for each strain. Antibiotics tested were Azithromycin (Table 12a, FIG. 9A) and Doxycycline (Table 12b, FIG. 9B).

Since all strains tested had previously been characterised as being susceptible to both antibiotics used in this example, a difference between the VITA Indices of treated and non-treated samples would be expected. The VITA Index of treated samples would be predicted to be lower than the untreated samples, as the presence of antibiotic would cause a disruption to normal transcriptional activity of cells. Subsequently, all samples indicated they were alive and actively transcribing regardless of treatment. This was observed from the amplification of TNA samples, extracted from untreated and treated groups, which displayed Ct values lower for GAT1/2 than the NED, independent of antibiotic used (Table 12a and 12b).

The fold change and VITA Indices were calculated for all samples at all time points post treatment, for each of the drugs used (Table 12a and 12b). Comparison of VITA indices, between the untreated and treated samples at each time point, demonstrated a significant difference, with VITA Indices for treated samples being lower than untreated, for all strains and antibiotics tested ($p<0.01$ using an unpaired t-test for each group; Table 12a and 12b, FIGS. 9A-B). This is consistent with the predicted results, evidencing the susceptibility of the strain to the drugs used for treatment and resulting in the disruption to the transcriptional activity. The ΔVITA Ratio, calculated by dividing the VITA Index (no antibiotic) by the VITA Index with antibiotic, also displayed similar results between each strain tested with the same antibiotic, and between antibiotics also (Table 12a and 12b).

This experiment, by the results obtained, demonstrates that the GAT1/2 and NED can be measured in a single reaction and results of this used to calculate VITA indices and ΔVITA Ratios. The individual responses obtained from each strain tested was consistent with its predicted susceptibility to both antibiotics used, obtained through analysis of the VITA Indices of treated vs non-treated. This further highlighted the ability to utilise VITA Indices to examine the antibiotic susceptibility of cells with a short incubation in the presence and absence of the drug of interest.

TABLE 12a

Results of a triplex RT-PCR analysis of TNA from treated and untreated samples, harvested one hour post treatment (PT) with Azithromycin.

| | Sample | Average Threshold (Ct) GAT1/2 | NED | ΔCt | FC | TR | VITA Index | ΔVITA Ratio A/B | P value |
|---|---|---|---|---|---|---|---|---|---|
| Strain 1 | A No Antibiotic | 15.71 | 19.25 | 3.54 | 11.66 | 2 | 5.83 | 1.47 | 0.0073 ** |
| | B Plus Antibiotic | 16.37 | 19.35 | 2.98 | 7.91 | 2 | 3.95 | | |
| Strain 2 | A No Antibiotic | 15.43 | 19.03 | 3.60 | 12.10 | 2 | 6.05 | 1.42 | 0.0005 *** |
| | B Plus Antibiotic | 16.33 | 19.43 | 3.09 | 8.53 | 2 | 4.27 | | |
| Strain 3 | A No Antibiotic | 17.48 | 21.38 | 3.90 | 14.88 | 2 | 7.44 | 1.31 | 0.0008 *** |
| | B Plus Antibiotic | 17.85 | 21.35 | 3.50 | 11.33 | 2 | 5.66 | | |
| Strain 5 | A No Antibiotic | 17.24 | 21.08 | 3.84 | 14.29 | 2 | 7.14 | 1.30 | 0.0006 *** |
| | B Plus Antibiotic | 17.69 | 21.15 | 3.46 | 11.00 | 2 | 5.50 | | |

TABLE 12b

Results of a triplex RT-PCR analysis of TNA from treated and untreated samples, harvested 1 hour post treatment (PT) with Doxycycline.

| | Sample | Average Threshold (Ct) GAT1/2 | NED | ΔCt | FC | TR | VITA Index | ΔVITA Ratio A/B | P value |
|---|---|---|---|---|---|---|---|---|---|
| Strain 1 | A No Antibiotic | 18.17 | 21.22 | 3.05 | 8.25 | 2 | 4.13 | 1.48 | <0.0001 **** |
| | B Plus Antibiotic | 18.87 | 21.35 | 2.48 | 5.59 | 2 | 2.80 | | |
| Strain 2 | A No Antibiotic | 15.61 | 18.89 | 3.28 | 9.71 | 2 | 4.86 | 1.24 | 0.008 *** |
| | B Plus Antibiotic | 16.22 | 19.19 | 2.97 | 7.84 | 2 | 3.92 | | |
| Strain 3 | A No Antibiotic | 17.48 | 21.38 | 3.90 | 14.88 | 2 | 7.44 | 1.32 | <0.0001 **** |
| | B Plus Antibiotic | 17.13 | 20.62 | 3.50 | 11.27 | 2 | 5.64 | | |
| Strain 5 | A No Antibiotic | 17.24 | 21.08 | 3.84 | 14.29 | 2 | 7.14 | 1.43 | <0.0001 **** |
| | B Plus Antibiotic | 18.21 | 21.53 | 3.33 | 10.02 | 2 | 5.01 | | |

Example 13: Antibiotic Susceptibility Testing with Rifampicin Using VITA PCR Using Resistant and Susceptible Strains The following example analyses the susceptibility of bacteria to a given drug, by estimation of the change of GAT levels relative to NED in TNA samples. These were then compared between samples treated with antibiotic and not treated (control). Samples were obtained from HEp-2 cells which had been infected with different *Chlamydia trachomatis* strains, previously characterized in culture to be either susceptible to the drug Rifampicin (total of four strains: serovar D, lab strain (strain 1), serovar L2, Wild Type lab strain (strain 2), serovar L2, Trimethoprim resistant strain (strain 3) and serovar L2, Spectinomycin resistant strain (strain 4)); or resistant to Rifampicin (serovar L2, Rifampicin resistant strain (strain 5)). TNA was extracted from cells, which had been either treated with a high dose of antibiotic, or not treated (control), 20 hours post infection whilst in an exponential growth phase. Treatment was as described in example 1, Treatment E (1.1.5), using a single concentration of Rifampicin (0.256 μg/mL), equivalent to 32 fold greater than MIC of susceptible trains and 32 fold below the MIC of the resistant strain. To obtain a measure GAT, *Chlamydia* DNA and RNA was amplified by RT-PCR using primers targeting two different locations of the omp1 gene and its transcripts. To measure NED, another region of *Chlamydia* DNA was co-amplified in the same RT-PCR using primers targeting a region of genomic DNA which is not transcribed. The levels of GAT and NED were estimated and used to calculate VITA Index. Further to this the VITA Indices of treated and untreated samples were used to calculate the ΔVITA.

13.1 VITA PCR Analysis of GAT1, GAT2 and NED

Partzyme oligonucleotides, Reporter substrates and PCR primers used for amplification and detection of GAT1, GAT2 and NED were as per example 9 (9.1, 9.2 and 9.3 respectively). The RT-PCR conditions used were as described in Example 9 (9.5) and reactions contained either 5 µL of TNA template (1/1000 dilution) or no target (dH$_2$O).

13.2 Preparation of TNA

RNA and DNA (TNA) were co-extracted from all different *Chlamydia trachomatis* strains (strain 1, 2, 3, 4 and 5) which had been cultured in HEp-2 cells, as described in example 1 (1.1 Culture, 1.1.5 Treatment Protocol E). Extraction was performed using the FireMonkey PuriSpin Extraction kit, as defined in example 1 (1.3 Total Nucleic Acid (TNA) extraction, 1.3.2 Extraction Protocol B) and following manufacturer's instructions for simultaneous extraction of DNA and RNA.

13.3 Results

*Chlamydia* DNA and RNA from 2 GAT regions and one NED region, were co-amplified and detected in single RT-PCR from TNA extracted from *chlamydia* cultures. These cultures were treated with antibiotic (Rifampicin) or left untreated (control) during the exponential growth phase and harvested at one hour post treatment. Table 13 displays the threshold cycle (Ct) values for the components in each sample, for each individual strain. The ΔCt was calculated as the differences between the Ct values of the NED and GAT1/2 signals. In turn, the fold change (difference between the GAT1/2 and NED) which would theoretically lead to those ΔCt values was estimated as $2^{\Delta Ct}$ and shown in Table 13. The results were compared between no treatment reactions (control) and those treated with antibiotic for each strain (FIG. 9C); and results were compared for susceptible versus resistant strains. The fold change and VITA Indices were calculated for all samples at one hour post treatment (Table 13).

Figure 9D:
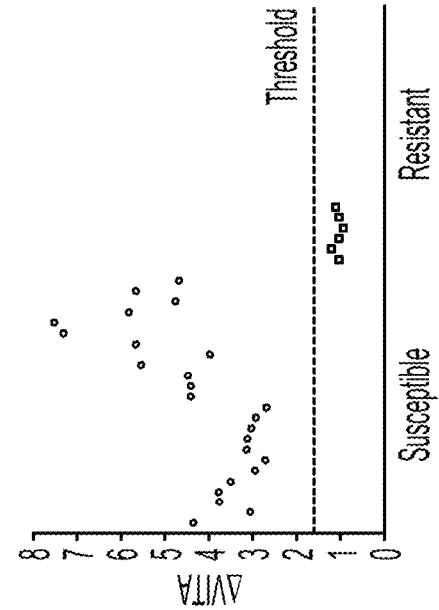
Figure 9C:
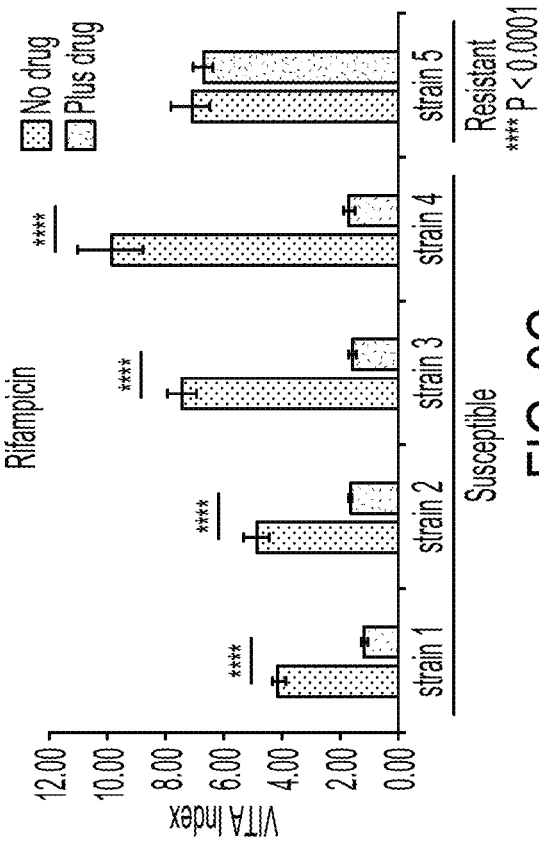

Comparison of VITA indices, between the untreated and treated samples presented a significant difference in the VITA indices for strains 1-4 (p<0.0001, using an unpaired t-test, Table 13). This is consistent with a disruption to the transcription activity of cells susceptible to the antibiotic used for treatment and visible in FIG. 9C. Comparison of VITA Indices for strain 5, between untreated and treated samples, showed no significant difference, with VITA Indices being similar (FIG. 9C, Table 13). This is indicative of resistance to the antibiotic rifampicin when incubated at 37° C. for 1 h, consistent with little or no disruption to the transcription of this strain.

The ΔVITA Ratio is calculated by dividing the VITA Index (no antibiotic) by the VITA Index with antibiotic. ΔVITA Ratio was significantly lower for strain 5, the resistant strain (Table 13), further demonstrating the reduced amount of difference between the treated and untreated samples. The ΔVITA Ratio for all other strains was in all instances >2.93 (Table 13). Graphing of the ΔVITA Ratio demonstrates visually the difference between the ΔVITA Ratio of susceptible and resistant strains (FIG. 9 panel iv). These differences were also determined as statistically different (p<0.0001, unpaired Welch's t-test). A threshold ΔVITA value of 1.63 allowed susceptible and resistant strains to be distinguished with 95% confidence (FIG. 9D).

Results from this experiment demonstrate that the GAT1/2 and NED can be measured in a single reaction and results of this used to calculate VITA indices. Alongside this, the comparison between VITA indices of treated and untreated cells, calculated as ΔVITA Ratio, further correlated with either a response or lack thereof to the presence of antibiotic. The individual responses obtained from each strain tested was consistent with its predicted susceptibility to the antibiotic used, whilst a lack of response was linked with the resistance profile of the strain tested. This further highlighted the ability to utilise VITA Indices to examine the antibiotic susceptibility or resistance of cells with a short incubation in the presence and absence of the drug of interest.

TABLE 13

Results of a triplex RT-PCR analysis of TNA from treated and untreated samples, with antibiotic Rifampicin, harvested 1 hour post treatment (PT) with comparison between susceptible and resistant strains.

| Strain | Sample | Average Threshold (Ct) GAT1/2 | NED | ΔCt | FC | TR | VITA Index | ΔVITA Ratio A/B | P value <0.0001 |
|---|---|---|---|---|---|---|---|---|---|
| 1 | A No Antibiotic | 18.17 | 21.22 | 3.05 | 8.25 | 2 | 4.13 | 3.54 | <0.0001 **** |
|   | B Plus Antibiotic | 20.32 | 21.54 | 1.22 | 2.33 | 2 | 1.17 |   |   |
| 2 | A No Antibiotic | 15.61 | 18.89 | 3.28 | 9.71 | 2 | 4.86 | 2.93 | <0.0001 **** |
|   | B Plus Antibiotic | 17.49 | 19.22 | 1.73 | 3.31 | 2 | 1.66 |   |   |
| 3 | A No Antibiotic | 17.48 | 21.38 | 3.9 | 14.88 | 2 | 7.44 | 4.70 | <0.0001 **** |
|   | B Plus Antibiotic | 18.81 | 20.47 | 1.66 | 3.16 | 2 | 1.58 |   |   |
| 4 | A No Antibiotic | 16.24 | 20.54 | 4.30 | 19.72 | 2 | 9.86 | 5.86 | <0.0001 **** |
|   | B Plus Antibiotic | 18.66 | 20.41 | 1.75 | 3.37 | 2 | 1.68 |   |   |
| 5 | A No Antibiotic | 17.24 | 21.08 | 3.84 | 14.29 | 2 | 7.14 | 1.06 | 0.1813 |
|   | B Plus Antibiotic | 17.41 | 21.16 | 3.75 | 13.42 | 2 | 6.71 |   |   |
|   | No TNA | No Ct | No Ct |   |   |   |   |   |   |

Example 14—Exemplary Antibiotic Susceptibility Testing Using VITA PCR

Figure 10:
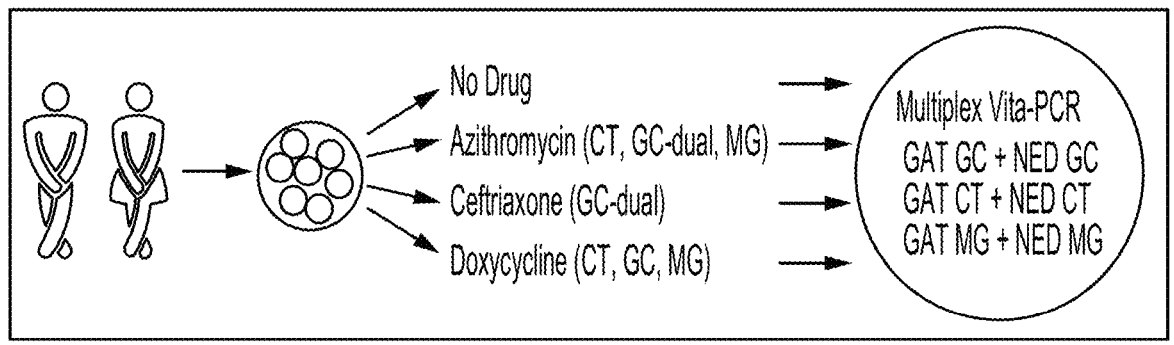
FIG. 10: Schematic of assays according to embodiments of the present invention. Hypothetical example demonstrating the process of Antibiotic Susceptibility Testing directly from a clinical specimen, with incubation with either no drug, or in the presence of azithromycin, ceftriaxone and doxycycline and further testing for *Chlamydia trachomatis* (CT), *Neisseria gonorrhoeae* (GC) and *Mycoplasma genitalium* (MG)GC-dual relates to the dual antibiotic therapy.

The following example describes a process, illustrated in FIG. 10, which could be used as a general screen for infections, including sexually transmitted infections and their antibiotic resistance/susceptibly status. A clinical specimen could be taken from a patient suspected of having a sexually transmitted infection such as *Neisseria* gonorrhea (GC), *Chlamydia trachomatis* (CT) or *Mycoplasma genitalium* (MG). The specimen could be split into subsamples, one of which is not incubated with any antibiotic, whilst the other could be incubated in the presence of a range of antibiotics used in the treatment of one or more of GC, CT and MG. Following incubation, total nucleic acid could be analysed in a multiplex VITAPCR assay with primers targeting GAT and NED specific for GC and/or CT and/or MG. Positive GAT and NED signal for a specific organism could allow diagnosis of an STI and comparison of VITA indices in the presence or absence of drugs could reveal which therapy, or therapies, may be used to treat the patient.

Further, one could analyse a large series of samples and establish threshold VITA Indices for each organism in the assay. This threshold value could then be used as a tool to diagnose these sexually transmitted infections and/or provide a method for Test of Cure following treatment with an appropriate antibiotic. Further, analysis of a large series of samples in the presence or absence of each antibiotic could allow determination of a ΔVITA Ratio Threshold capable of distinguishing sensitivity or resistance of each organism to each antibiotic. The ΔVITA Ratio Threshold could then be used as a tool to predict response to specific antibiotic in a format which would no longer require a sub-sample of the specimen or sample to serve as an untreated, control comparator. Further, since example 7 has shown that sensitivity and resistance can be determined following as little as a 5 minutes incubation, coupling the incubation to rapid amplification protocol could make it suitable as a rapid point of care test. Finally, since example 7 also demonstrated that incubation with the drug can be performed at room temperature, such a test should not require additional equipment beyond that required for extraction and amplification.

Example 15—Use of VITA PCR on Different Loads of Viable Material

The following example estimates levels of NED and GAT in samples with varying loads of viable to dead bacteria. TNA was extracted from HEp-2 cells infected with *Chlamydia trachomatis* (serovar D), either not treated (Alive CT) or treated with a high dose 0.512 ug/ml for 40 hours of the antibiotic azithromycin (Dead CT). Upon harvesting these were mixed in different ratios to obtain different viable loads of 0%, 0.1%, 0.2%, 0.5%, 1%, 10%, 20%, 50% and 100%, as described in example 1, Treatment F (1.1.6). *Chlamydia* DNA and RNA was amplified by RT-PCR using primers targeting two different locations of the omp1 gene and its transcripts to measure GAT. Another region of *Chlamydia* DNA was co-amplified in the same RT-PCR using primers targeting a region of genomic DNA which is not transcribed to measure NED. The levels of GAT and NED were estimated and used to calculate VITA Index.

15.1 VITA PCR Analysis of GAT1, GAT2 and NED

Partzyme oligonucleotides, Reporter substrates and PCR primers used for amplification and detection of GAT1, GAT2 and NED were as per example 9 (9.1, 9.2 and 9.3 respectively). The reverse primer for NED (SEQ ID NO 23) was substituted in this example for the following.

```
Reverse primer for NED 3CTinfAIGR_1
                                SEQ ID NO: 13
CAAGAGAGAATGTCAAAAGATAC
```

The RT-PCR conditions used were as described in Example 9 (9.5) and reactions contained either 5 μL of TNA template (1/100 dilution) or no target (dH$_2$O).

15.2 Preparation of TNA

RNA and DNA (TNA) were co-extracted from *Chlamydia trachomatis* (serovar D) which had been cultured in HEp-2 cells, as described in example 1 (1.1 Culture, 1.1.6 Treatment Protocol F). Extraction was performed using the FireMonkey PuriSpin Extraction kit, as defined in example 1 (1.3 Total Nucleic Acid (TNA) extraction, 1.3.2 Extraction Protocol B) and following manufacturer's instructions for simultaneous extraction of DNA and RNA.

15.3 Results

*Chlamydia* DNA and RNA (GAT), or DNA only (NED), were co-amplified in single RT-PCR from TNA extracted from a mixture of viable untreated cells (Alive CT) and cells treated with a high dose of antibiotic (Dead CT) to generate varying loads of viable *chlamydia*. Table 14 show the threshold cycle (Ct) values measured for each viability load, using either GAT1 or GAT1/2 in the reaction. The ΔCt was calculated as the differences between the Ct values of the NED and GAT signals. In turn, the fold change (ratio of GAT to NED) which would theoretically lead to those ΔCt values was estimated as $2^{\Delta Ct}$ and plotted in Table 15 and VITA Indices were plotted in FIG. 11A. The results were then compared to the percentage of viability in each mixture.

Analysis of viability, through infectivity and immunofluorescent staining, was performed to confirm the accuracy of load in each mixed sample. This visually confirmed the increase in Chlamydial inclusions as the percentage of viability increased (data not included).

Theoretically, low loads of viable cells would have lower levels of transcripts detectable in a background of genomic DNA derived from non-viable cells. If DNA is not degraded during treatment, the amount of DNA detected could be anticipated to be greater than the amount of RNA, since DNA is inherently more stable than RNA. In samples with high loads of viable cells, it is expected that higher amounts of transcripts would be present.

Analysis of results showed that when TNA extracted from a 0% viable load sample was amplified, the ΔCt value for GAT and NED was small (Table 14) indicating little or no active transcription. For all samples with 0.2% or more viable load the Ct value for GAT was lower than the NED (Table 14) consistent with active transcription. The fold change and VITA Indices were calculated for all the viable loads (Table 14). The VITA indices were significantly different for sample with 0% viable load compared to those with 0.2% or greater of viable load (FIG. 11A, Table 14, p<0.05). Significant differences were not observed between mixtures containing viable loads greater than 0.2% (Table 14, p>0.05). Viability loads of 0.1% were also tested and VITA Index was found to be significantly different to the VITA Index of 0% viable loads, but was also significantly different to viable loads greater than 0.2% (data not shown).

As expected, the different viable loads also lead to a difference in Ct values for the GAT and NED reactions, as the Ct values would correlate to chromosomal copies of *Chlamydia trachomatis* in each mixture. Since cells, from dead CT, were incubated with drug for 40 hours this suggests there may not have only been a halt in active transcription of RNA but also of active replication of the bacteria, affecting the concentration of DNA. It is also likely that there was degradation of both DNA and RNA during this time. As such, higher loads of viable bacteria showed lower Ct values (earlier detection) than lower viability loads (detection in later PCR cycles) (FIG. 11B). This also correlates with the analysis of chlamydial viability from the mixtures (FIG. 11A).

The data from this example demonstrates that the VITA Indices correlate with the measure of viable and non-viable populations, as evidenced by the differentiation between viable populations with as low load as 0.10% and non-viable populations. This example demonstrates that GAT and NED can be measured in a single reaction and the results can be used to calculate VITA Indices which correlate with the observed viability, as low as 0.1% viable load and its distinction from non-viable populations. Finally, this example demonstrates a major advantage of VITA PCR in that it is not necessary to quantify the amount of TNA which is added to the VITA PCR as the method determines the ratio of GAT to NED regardless of the amount of starting material. Evidence for this is the fact that no significant difference is observed between viable loads, over the broad range investigated in this example.

TABLE 14

Results of a Triplex RT-PCR analysis of TNA from samples containing different viability loads

| Sample % viable | Threshold (Ct) GAT1/2 | NED | ΔCt | FC | TR 2xGAT to 1xNED | VITA Index | P value |
|---|---|---|---|---|---|---|---|
| 0% | 21.45 | 22.80 | 1.35 | 2.55 | 2 | 1.27 | 0.0035 |
| 0.2% | 19.16 | 21.77 | 2.60 | 6.08 | 2 | 3.04 | ** 0.1911 |
| 0.5% | 17.76 | 20.26 | 2.50 | 5.66 | 2 | 2.83 | |
| 1% | 17.06 | 19.52 | 2.47 | 5.53 | 2 | 2.76 | |
| 10% | 13.44 | 16.13 | 2.69 | 6.47 | 2 | 3.23 | |
| 20% | 12.28 | 14.85 | 2.57 | 5.95 | 2 | 2.98 | |
| 50% | 11.25 | 13.72 | 2.47 | 5.53 | 2 | 2.76 | |
| 100% | 10.24 | 12.66 | 2.42 | 5.36 | 2 | 2.68 | |
| No TNA | No Ct | No Ct | | | | | |

Example 16—Influence of Amplicon Size and Other RT-PCR Parameters on VITA Indices The following example estimates levels of NED and GAT in TNA samples extracted from HEp-2 cells infected with *Chlamydia trachomatis* (serovar D). TNA was extracted from cells which were not incubated with antibiotic (untreated, viable cells), and from cells incubated with antibiotic at a concentration eight times below the MIC (<MIC), at the MIC (MIC) or at 8 times greater than the MIC (>MIC), as described in example 1, Treatment Protocol A (1.2.1). *Chlamydia* DNA and RNA (GAT) was amplified by RT-PCR using primers targeting two different locations of the omp1 gene and its transcripts (GAT1/2). The two primer pairs used to amplify the two omp1 GAT targets in this experiment (section 16.3 SEQ ID N04 and 24; SEQ ID NO 16 and 25) generated longer amplicons than those generated using the two GAT primer pairs used in previous examples including example 5 (section 5.3 SEQ ID NO 4 and 5, SEQ ID NO 16 and 17). The resultant amplicons were 215 bp and 311 bp long for GAT1 and GAT2 respectively. *Chlamydia* DNA only (NED) was co-amplified in the same RT-PCR mix using primers targeting a region of genomic DNA designated InfA_IGRwhich is not transcribed. The Ct values of GAT1/2 and NED were estimated for the RT-PCR for all treatments.

16.1 VITA PCR Analysis of GAT1, GAT2 and NED

Partzymes were designed to assemble into two active MNAzymes when they bound to amplicons generated by amplification of either the omp1 gene or omp1 transcripts. These two MNAzymes were capable of binding to two different amplicons derived by amplification of two separate regions of omp1 (a GAT1 and a GAT2 region). Once assembled, both MNAzymes could cleave the same reporter substrate Sub102(20)-FB. A third pair of partzymes was designed to assemble into an active MNAzymes when bound to amplicons generated by amplification of a non-transcribed DNA region denoted infA_IGR thus providing a measure of NED. Once assembled, this MNAzyme could cleave the reporter substrate Sub72-A1B. The sequences of Partzyme A and Partzyme B for each MNAzyme are listed below, from 5' to 3'. Bases in bold hybridize with the target, underlined bases form part of the catalytic core in the assembled MNAzyme and bases in italic refer to sequence which hybridizes to the substrate.

Partzyme A for GAT1 omp1_A4/102-P
SEQ ID NO: 6
TGGTCTCGAGCATTGAACGA<u>ACAACGAGGGA</u>*CGTCGA*/3Phos/

Partzyme B for GAT1 omp1_B5/102-P
SEQ ID NO: 7
*CGGTAGAGG*<u>AGGCTAGCT</u>CATGTTCTCGATTAAGGCTG/3Phos/

PartzymeA for GAT2 CTomp1L_A4/102-P
SEQ ID NO: 20
CTTGCACCACTTGGTGTGACG<u>ACAACGAGGGA</u>*CGTCGA*/3phos/

Partzyme B for GAT2 CTomp1L_B5/102-P
SEQ ID NO: 21
*CGGTAGAGG*<u>AGGCTAGCT</u>CTATCAGCATGCGTGTGGGTTA/3phos/

Partzyme A for NED CTinfAIGR_A4/72-P
SEQ ID NO: 8
TCGACTAAACAGAAAATGTCAAA<u>ACAACGA</u>*GAGGCGTGAT*/3Phos/

Partzyme B for NED CTinfAIGR_B5/72-P
SEQ ID NO: 9
*CTGGGAGGAGAGG*<u>CTAGCT</u>CAACTTGTCAAAAAACAGAAGG/3Phos/

16.2 Reporter Substrates

In the current example, two different reporter substrates were used, each labelled with distinct fluorophores. Sub102(20)-FB was end-labelled at the 5' end with 6-FAM and with IABkFQ at the 3' end, and its cleavage was monitored at 516 nm with excitation at 492 nm. Sub72-A1B was labelled with ATTO™ Rho101 at the 5' end and with IAbRQSp at the 3' end, and its cleavage was monitored at 609 nm with excitation at 592 nm. The reporter substrates for this example are shown below with the sequence, 5' to 3'. The lower case bases represent RNA and the upper case bases represent DNA.

for GAT1 and GAT2 Sub102(20)-FB
SEQ ID NO: 10
TCGACGTCCCguCCTCTACCG for NED Sub72-A1B
SEQ ID NO: 11
ATCACGCCTCguCTCCTCCCAG

16.3 PCR Primers for Amplification of GAT1, GAT2 and NED

In vitro amplification of TNA template extracted from cells infected with *Chlamydia trachomatis* was performed using the primers listed below. The Forward and Reverse primers were used to amplify two regions of the omp1 gene and transcripts (GAT1 and GAT2) and infA_IGR DNA (NED) by RT-PCR. All sequences are written 5' to 3'.

```
Forward primer for GAT1 5omp1
                                  SEQ ID NO: 4
CTTCTTCCTGGGACGAACG Reverse primer for GAT1 3omp1_2Lhp3
                                  SEQ ID NO: 24
GAGCTATAATTAGCTCTCTTTGTGCTC Forward primer for GAT2 5CTomp1_1
                                  SEQ ID NO: 16
TTTCGGCGGAGATCCTTGCGATCC Reverse primer for GAT2 3CTomp1_6
                                  SEQ ID NO: 25
GATATCCACTGGTGGCTCCTAA Forward primer for NED 5CTInfAIGR_2
                                  SEQ ID NO: 12
GAGAGAGTGATTATATCGACTAA Reverse primer for NED 3CTInfAIGR_3
                                  SEQ ID NO: 23
GCAAAAACTCAAGAGAGAATGTC
```

16.4 Preparation of TNA

RNA and DNA (TNA) were co-extracted from *Chlamydia trachomatis* (serovar D) which had been obtained through in-vitro methods, cultured in HEp-2 cells, as described in example 1 (1.1 Culture, 1.1.1 Treatment Protocol A). Extraction was performed as a LLE technique, using phenol:chloroform:isoamyl, also described in example 1 (1.3 Total Nucleic Acid (TNA) extraction).

16.5 Reaction Components

All reactions contained 40 nM of each Forward primer, 200 nM of each Reverse primer, 200 nM of each partzyme A, 200 nM of each partzyme B, 400 nm of substrate SEQ ID NO 10, 200 nM substrate SEQ ID NO 11, 1× SensiFAST Probe No-ROX Mix One-Step (Bioline), 2 mM $MgCl_2$ (Bioline), 0.2 U/μL RiboSafe RNase Inhibitor (Bioline), 0.2 μL of Reverse Transcriptase enzyme (Bioline) and nuclease free water (Ambion), in a total volume of 20 μL. All reactions were performed in triplicate on a BioRad® CFX96 thermocycler. The cycling parameters were 48° C. for 10 minutes, 95° C. for 2 min, 10 cycles of 95° C. for 5 seconds and 61° C. for 30 seconds (with a 0.5° C. decrease in temperature per cycle), and 30 cycles of 95° C. for 5 seconds and 52° C. for 50 seconds. The reactions contained either 5 μL of TNA template (1/1000 dilution) or no target ($dH_2O$).

16.6 Results

*Chlamydia* DNA and RNA from 2 regions within the omp gene and transcripts (GAT1 and GAT2), and one NED region, were co-amplified in single RT-PCR from TNA extracted from viable untreated cells and from cells incubated with antibiotic at concentrations below (<MIC), equal to (MIC) or above the MIC (>MIC). Table 15 shows the threshold cycle (Ct) values measured for NED, and for the combined signals from GAT1 and GAT2 (GAT1/2), in each sample. The ΔCt was calculated as the differences between the Ct values of the NED and GAT1/2. In turn, the fold change (ratio of GAT to NED) which would theoretically led to those ΔCt values was estimated as $2^{\Delta Ct}$ and shown in Table 15. The VITA Indices were calculated by dividing the FC by the TR. The results were then compared to the viability in each cell population.

Primer pairs used in this example generated longer amplicons than that observed in previous examples. Amplicon lengths were 215 bp and 311 bp for GAT1 and GAT2 respectively. The use of longer amplicons may be expected to provide more accurate and stringent estimation of the viability of the organism in question, because these primer sets will amplify less of short, residual fragments associated with dead cells or cells where expression is decreased by the presence of an antibiotic. The use of longer versus shorter amplicons for the GAT would therefore be expected to alter the absolute values obtained for VITA Indices for each of the samples tested (untreated or treated with different doses of antibiotic) but would not be expected to alter the correlation between cell viability as measured by immunofluorescent staining (FIGS. 3A-B) or the information that can be inferred by examination of the VITA Indices (Table 15, FIG. 12).

TABLE 15

Results of triplex RT-PCR analysis of TNA from treated and untreated samples, amplified using primer pairs creating long amplicon lengths for GAT1 and GAT2

| Sample | Threshold (Ct) | | ΔCt | FC | TR 2×GAT/ 1×NED | VITA Index |
|---|---|---|---|---|---|---|
| | GAT1/2 | NED | | | | |
| No Antibiotic | 19.20 | 20.65 | 1.45 | 2.73 | 2 | 1.37 |
| <MIC | 21.06 | 22.67 | 1.61 | 3.05 | 2 | 1.53 |
| MIC | 30.54 | 30.82 | 0.28 | 1.21 | 2 | 0.61 |
| >MIC | 29.21 | 29.21 | −0.33 | 0.80 | 2 | 0.40 |
| No TNA | No Ct | No Ct | | | | |

Analysis of results shows that when TNA samples extracted from untreated or treated samples below the MIC, were amplified the Ct value for GAT1/2 was lower than the NED (Table 15) consistent with active transcription in both sample types. For GAT1/2 and NED from TNA treated at the MIC level or above, the differences in Ct value were very low (<1) (Table 15) indicating DNA is not being actively transcribed. The fold change and VITA Indices were calculated for the four sample types (Table 15). Since two genes and their transcripts were used to calculate the GAT1/2, and only a single un-transcribed region was used to calculate NED, then the fold change is divided by the TR to calculate the VITA Indices (Table 15). The data demonstrates that long GAT amplicons translated into lower VITA Indices (FIG. 12) comparatively to shorter amplicons used for detection as seen in example 5 (FIG. 5B). This indicates that fewer partially degraded transcript fragments are being detected by the GAT primers that generate longer amplicons.

The results from this example demonstrate that GAT and NED can be measured in a single reaction and the results used to calculate VITA Indices which correlate with the observed viability of cells. It further displays differences in VITA Indices between viable and non-viable samples, with VITA Indices being lower than that observed with short amplicons for GAT1 and GAT2. Despite the different parameters used in this example the ultimate distinction between viable and non-viable cells is accurately called, with similar trends observed for all samples comparatively to VITA Indices with shorter amplicons for GAT1 and GAT2.

Example 17—Exemplary Test of Cure and Antibiotic Susceptibility Testing for *Neisseria gonorrhoeae* Using VITA PCR The following example describes an assay targeting GAT and NED used for diagnosis, TOC and AST for *Neisseria gonorrhoeae* (GC). The assay would estimate the change of GAT relative to NED in TNA samples. To measure GAT, *gonorrhoeae* DNA and RNA would be amplified by RT-PCR using primers targeting locations of a gene and its transcripts or multiple genes and their transcripts. To measure NED, another region of *gonorrhoeae* DNA would be co-amplified in the same RT-PCR reaction using primers pairs targeting a region of genomic DNA which is not transcribed. Potential GAT and NED targets can be screened as per example 3. The levels of GAT and NED would be estimated and used to calculate the VITA Indices. The VITA indices generated would allow the determination of viability of the organism in any given sample (e.g. urine, vaginal swab, rectal swab or throat swab). Further to this, the sample could also be used for Antibiotic susceptibility testing by splitting the sample and incubating it in the presence and absence of a desired drug or multiple drugs. The levels of GAT and NED would be estimated and used to calculate the VITA Indices for each condition. Further to this the VITA Indices of treated and untreated samples would be used to calculate the ΔVITA, ultimately determining the susceptibility or resistance profile of the organism. This would aid in the guidance of therapy, with the best choice antibiotic being given at first presentation of symptoms.

Potential target genes and respective sequences of MNAzymes, reporter substrates and primer pairs used for their amplification are listed in the following sections (17.1, 17.2 and 17.3). Reporter substrates are different to those tested for GAT and NED assays targeting *Chlamydia trachomatis*, allowing for the potential to multiplex all targets together, as embodied in example 14, FIG. 10. Further target organisms may also be further included (example 14, FIG. 10). This would permit identification, confirmation of status of infection and antibiotic susceptibility testing, in a single reaction for both organisms.

17.1 Candidate Targets for GAT1, GAT2 and NED for VITA PCR Analysis

Partzymes have been designed to assemble into two active MNAzymes when they bound to amplicons generated by amplification of different genes, the ompA or cysK gene or transcripts. These two MNAzymes are designed to bind to two different amplicons derived by amplification of the two separate genes, representing GAT1 and GAT2 respectively. Once assembled, both MNAzymes could cleave the same reporter substrate Sub97(20)-JB. A third pair of partzymes has been designed to assemble into an active MNAzyme when bound to amplicons generated by amplification of a non-transcribed DNA region denoted IGR1109 which is a candidate for measuring NED. Once assembled, this MNAzyme would be capable of cleaving the reporter substrate Sub84(20)-CB. The sequences of partzyme A and Partzyme B for each MNAzyme are listed below, from 5' to 3'. Bases in bold hybridize with the target, underlined bases form part of the catalytic core in the assembled MNAzyme and bases in italic refer to sequence which hybridizes to the substrate.

```
Partzyme A for GAT1 NGompA_3A4/97-P
                                        SEQ ID NO: 26
GGTTGCCTACTATCTGCAGAACAACGAGAGGACTAGG/3Phos/

Partzyme B for GAT1 NGompA_3B5/97-P
                                        SEQ ID NO: 27
GACGTGAGGAGGCTAGCTCGCGCGGCGTGGCGGCT/3Phos/

Partzyme A for GAT2 NGcysK_3A4/97-P
                                        SEQ ID NO: 28
ACGACAGCATTGCCAAAGTGACAACGAGAGGACTAGG/3Phos/

Partzyme B for GAT2 NGcysK_3B5/97-P
                                        SEQ ID NO: 29
GACGTGAGGAGGCTAGCTCCGAACGAAGCGGCTTTTG/3Phos/

Partzyme A for NED NG1109IGR_A4/84-P
                                        SEQ ID NO: 30
TGCTTTTGCTGTGAAAAAGGGACAACGAGAGGGTCGAG/3Phos/

Partzyme B for NED NG1109IGR_B5/84-P
                                        SEQ ID NO: 31
GGACGAGGGAGGCTAGCTCTGAAATTGCCAACAATCCTG/3Phos/
```

17.2 Reporter Substrates

In the current example, two different reporter substrates, labelled with distinct fluorophores would be useful in detection in systems incorporating the partzymes/MNAzyme listed above. These substrates are Sub97(20)-JB end-labelled at the 5' end with 5-JOEN and IABkFQ at the 3' end, the cleavage of which could be monitored at 555 nm with excitation at 529 nm and Sub84(20)-CB labelled with 5Cy5 at the 5' end and with IAbRQSp at the 3' end, the cleavage of which could be monitored at 668 nm with excitation at 648 nm. These reporter substrates are shown below with the sequence, 5' to 3' where lower case bases represent RNA and the upper case bases represent DNA.

```
for GAT1 and GAT2 Sub97(20)-JB
                                        SEQ ID NO: 32
CCTAGTCCTCguCCTCACGTC for NED Sub84(20)-CB
                                        SEQ ID NO: 33
CTCGACCCTCguCCCTCGTCC
```

17.3 PCR Primers for Amplification of GAT1, GAT2 and NED

Amplification of TNA could be performed using the primers listed below. The Forward and Reverse primers are designed to amplify two separate genes and transcripts, ompA and cysK (GAT1 and GAT2) as well as IGR1109 DNA (NED) by RT-PCR. All sequences are written 5' to 3'.

```
Forward primer for GAT1 5NGompA_1
                                        SEQ ID NO: 34
CGGCACGCAAATCGAAATCC Reverse primer for GAT1 3NGompA_L1
                                        SEQ ID NO: 35
TGCGCGCGGCCTTCAACC Forward primer for GAT2 5NGcysK_3W3g
                                        SEQ ID NO: 36
CTTGGTGGACGCTCATGCA Reverse primer for GAT2 3NGcysK_2W3a
                                        SEQ ID NO: 37
GCCTTCTTTTTCCGCCATTACA
```

```
Forward primer for NED 5NG1109IGR_1
                                   SEQ ID NO: 38
GTTTTCACGCCTGCTTTTGC Reverse primer for NED 3NG1109IGR_1
                                   SEQ ID NO: 39
GACGCTCAAAACGCGGACGA
```

Primers for GAT for additional candidate genes including porB and rpmB can be screened using the method outlined in example 3.

Example 18—Influence of Amplification Efficiency, Sensitivity, Inclusivity and Specificity on VITA Indices The following example discusses parameters that can further influence the absolute values observed for the VITA Indices obtained for a specific multiplexed assay. The amplification efficiencies of GAT and NED assays included in the VITA PCR analysis should ideally be high and equal for GAT and NED. The amplification efficiencies of GAT1, GAT2 and NED targeting *Chlamydia trachomatis*, used in several examples, including Example 5, were estimated using synthetic target sequences serially diluted and found to be similar to each other, with efficiencies close to 100%, with $R^2 > 0.998$ (data not shown). When all components of the reaction are efficient and comparable to each other, the VITA indexes obtained have been shown to allow accurate differentiate between viable and non-viable cells, as evidenced in example 5 (FIG. 5B).

Another important factor is the length of the amplicons generated by amplification with the GAT and NED primers. As previous shown (example 16) VITA PCR systems generating longer amplicons may have lower observed values for VITA Indices, compared to systems generating shorter amplicons. However, whilst the absolute values of the VITA Indices can change, the correlation between the observed values and viability is maintained.

Factors affecting the power of VITA PCR to provide a versatile tool for basic research and clinical investigations include the sensitivity, inclusivity and specificity. Sensitivity impact the ability to detect target, specifically at the lower limit of detection, such as <10 copies. Inclusivity would relate to the ability to detect all strains and serovars, within the same species of organism, with the same efficiency. Specificity would relate to the detection of target being specific only to the organism of interest. Detection of "off target", but related species, could cause increased VITA Indices not reflective of the viability of the cell, organism or virus of interest.

It has also been discussed that the target used for GAT and NED must be chosen carefully. Example 3 shows a method for determining if a specific sequence meet the criteria ie GAT must target DNA region which is expressed, while NED primers must target a region which is not expressed. The examples in this document have shown that it is possible to use more than one GAT in a particular VITA PCR. This is in fact highly desirable, as specific genes may only be expressed during certain stages in the development cycle of, for example, bacteria. An assay containing multiple genes expressed, preferably at high levels under different conditions, could ensure expression will consistently be detectable in various conditions.

Finally, the choice of GAT targets is predicted to be dependent on the organism and the antibiotic under investigation. For example, studies by other groups have shown that the porB and rpmB transcripts of *Neisseria gonorrhoeae* are highly expressed and change in expression levels in response to the antibiotic ciprofloxacin. The *Chlamydia trachomatis* omp1 gene and its transcripts has been shown (example 9) to be suitable for discriminating resistance or susceptibility to rifampicin, and able to reflect viability of the organism.

---

The invention claimed is:

1. A method for normalising quantitative data obtained by amplification of nucleic acids from a cell, organism, or virus, the method comprising:
   (i) performing a combined amplification of genomic DNA from a first gene and RNA transcribed from the first gene thereby obtaining quantitative data, which is a combined measure of the genomic DNA from the first gene and RNA transcribed from the first gene, and an amplification of a sequence of non-transcribed genomic DNA in the cell organism or virus, thereby obtaining quantitative data, which is a measure of the sequence of non-transcribed genomic DNA,
   wherein the genomic DNA from the first gene and RNA transcribed from the first gene, and the sequence of non-transcribed genomic DNA are co-amplified in the same reaction,
   wherein the nucleic acids from the cell, organism, or virus are an extract of total nucleic acids,
   and wherein the reaction comprises using reverse transcriptase;
   (ii) normalizing the quantitative data from the combined amplification to the quantitative data from the amplification of the sequence of the non-transcribed genomic DNA to derive a normalised value (nV) representative of the relative amounts of:
   said genomic DNA and RNA transcripts of the first gene, to the non-transcribed genomic DNA, present within the nucleic acid sample prior said amplification.

2. The method of claim 1, wherein the quantitative data is amplicon copy number, and the method comprises:
   (i) obtaining a value A (vA) representing total amplicon number generated from the amplification of said genomic DNA and RNA transcripts of the first gene, and a value B (vB) representing total amplicon number generated from the sequence of non-transcribed genomic DNA;

calculating a normalised value (nV) using the equation:

$vA/vB = nV$ or an equivalent form thereof, and/or (ii) obtaining a value X (vX) representing total amplicon number generated from: the amplification of genomic DNA and RNA transcripts from the first gene, and amplification of genomic DNA and RNA transcripts from at least one additional gene;
obtaining a value B (vB) representing total amplicon number generated from the sequence of non-transcribed genomic DNA, calculating a normalised value (nV) using the equation:

$vX/(vB \times (X+1)) = nV$ or an equivalent form thereof, wherein $X$ is the number of said additional gene(s).

3. The method of claim 1, wherein the quantitative data is threshold value (Ct), and the method comprises:
(i) obtaining a cycle threshold value CtA from the amplification of said genomic DNA and RNA transcripts of the first gene, obtaining a cycle threshold value CtB from the amplification of the sequence of non-transcribed genomic DNA; and
calculating a normalised value (nV) using the equation:

$2^{CtB-CtA} = nV$ or an equivalent form thereof; and/or (ii) obtaining a cycle threshold value CtX from: the amplification of said genomic DNA and RNA transcripts of the first gene, and from amplification of genomic DNA and RNA transcripts from at least one additional gene;
obtaining a cycle threshold value CtB from the amplification of the sequence of non-transcribed genomic DNA; and
calculating a normalised value (nV) using the equation:
$2^{CtB-CtX}/(X+1) = nV$ or an equivalent form thereof, wherein X is the number of said additional gene(s).

4. The method of claim 1
(i) wherein the nucleic acids from the cell, organism, or virus are an extract of total nucleic acids; and/or
(ii) further comprising conducting said amplification of the nucleic acids from the cell, organism, or virus.

5. The method of claim 1, wherein any said amplification is conducted using: polymerase chain reaction (PCR), reverse transcription polymerase chain reaction (RT-PCR), strand displacement amplification (SDA), loop-mediated isothermal amplification (LAMP), rolling circle amplification (RCA), recombinase polymerase amplification (RPA), helicase dependent amplification (HDA), strand invasion based amplification (SIBA), transcript-mediated amplification (TMA), self-sustained sequence replication (3SR), nucleic acid sequence based amplification (NASBA), quantitative polymerase chain reaction (qPCR), digital polymerase chain reaction (dPCR), or any combination thereof.

6. The method of claim 1, further comprising:
(i) using the normalised value (nV) to assess the level of transcriptional activity in the cell, organism, or virus; and/or
(ii) obtaining a transcription-negative normalised value (nV−) generated using a series of said normalised values (nV) obtained from individuals of a population of the cells, organisms, or viruses known not to have transcriptional activity; and
comparing the normalised value (nV) obtained by said amplification of nucleic acids from the cell, organism, or virus to the transcription-negative normalised value (nV−), to thereby assess the level of transcriptional activity in the cell, organism, or virus.

7. The method of claim 6, wherein:
(i) the transcription-negative normalised value (nV−) is used as a base value for assessing a presence or an absence of transcriptional activity in the cell, organism or virus; and
an absence of transcriptional activity is indicated when the normalised value (nV) obtained by said amplification of nucleic acids from the cell, organism, or virus is equal to or below the transcription-negative normalised value (nV−); or
transcriptional activity is indicated when the normalised value (nV) obtained by said amplification of nucleic acids from the cell, organism, or virus is above the transcription-negative normalised value (nV−); and/or
(ii) said transcription-negative normalised value (nV−):
incorporates statistical variation in said series of normalised values (nV) from individuals of the population of the cells, organisms, or viruses known not to have transcriptional activity; and/or
is provided with a confidence interval that said transcription-negative normalised value (nV−) is predictive of a presence or an absence of transcriptional activity in the cell, organism or virus.

8. The method of claim 6, further comprising:
obtaining a transcription-positive normalised value (nV+) generated using a series of said normalised values (nV) obtained from individuals of a population of the cells, organisms, or viruses known to have transcriptional activity; and
comparing the normalised value (nV) obtained by said amplification of nucleic acids from the cell, organism, or virus to the transcription-positive normalised value (nV+), to thereby assess the level of transcriptional activity in the cell, organism, or virus.

9. The method of claim 8, wherein:
(i) the transcription-positive normalised value (nV+) is used as a base value for transcriptional activity in the cell, organism or virus; and
a lack or absence of transcriptional activity is indicated when the normalised value (nV) obtained by said amplification of nucleic acids from the cell, organism, or virus is below the transcription-positive normalised value (nV+); or
transcriptional activity is indicated when the normalised value (nV) obtained by said amplification of nucleic acids from the cell, organism, or virus is equal to or above the transcription-positive normalised value (nV+); and/or
(ii) said transcription-positive normalised value (nV+):
incorporates statistical variation in said series of normalised values (nV) from individuals of the population of the cells, organisms, or viruses known to have transcriptional activity; and/or
is provided with a confidence interval that said transcription-positive normalised value (nV+) is predictive of a presence or an absence of transcriptional activity in the cell, organism or virus.

10. The method of claim 6, further comprising:
obtaining a transcription-negative normalised value (nV−) generated using a series of said normalised values (nV) obtained from individuals of a population of the cells, organisms, or viruses known not to have transcriptional activity;
obtaining a transcription-positive normalised value (nV+) generated using a series of said normalised values (nV)

obtained from individuals of a population of the cells, organisms, or viruses known to have transcriptional activity; and comparing the normalised value (nV) obtained by said amplification of nucleic acids from the cell, organism, or virus to:

(i) the transcription-negative normalised value (nV−) and to the transcription-positive normalised value (nV+), or (ii) to a combined transcription normalised value (nV±) intermediate to the transcription-negative normalised value (nV−) and the transcription-positive normalised value (nV+), to thereby assess the level of transcriptional activity in the cell, organism, or virus.

11. The method of claim 10, wherein:

(i) the combined transcription normalised value (nV±) is calculated using the equation:

$$(nV+)+(nV-)/2=(nV^{\pm})\text{ or an equivalent form thereof,}$$

and/or (ii) said combined transcription normalised value (nV±):

incorporates statistical variation in said series of transcription-negative normalised value (nV−) and/or said transcription-positive normalised value (nV+); and/or is provided with a confidence interval that said combined transcription normalised value (nV±) is predictive of a presence or an absence of transcriptional activity in the cell, organism or virus.

12. The method of claim 6, wherein the level of transcriptional activity in the cell, organism, or virus is assessed for the purpose of determining any one or more of:

viability of the test cell or the test organism;
whether the test cell, organism or virus is alive or dead;
transcriptional perturbation within the test cell, organism, or virus.

13. The method of claim 1, further comprising:

(i) using the normalised value (nV) to assess the level of drug resistance or drug sensitivity in the cell, organism, or virus, wherein:

said cell, organism, or virus has been treated with a drug prior to said amplification of nucleic acids, and said normalised value (nV) is compared to a control normalised value (cnV) generated using a series of said normalised values (nV) obtained from individuals of a population of the cells, organisms, or viruses known to be:

(a) resistant to the drug; or
(b) sensitive to the drug, to thereby assess the level of drug resistance or drug sensitivity in the cell, organism, or virus; and/or (ii) obtaining a drug-sensitive normalised value (dsV) generated using a series of said normalised values (nV) obtained from individuals of a population of the cells, organisms, or viruses known to be sensitive to the drug; and comparing the normalised value (nV) obtained by said amplification of nucleic acids from the cell, organism, or virus to the drug-sensitive normalised value (dsV), to thereby assess the level of drug resistance or drug sensitivity or in the cell, organism, or virus, wherein the cell, organism, or virus has been treated with a drug prior to said amplification of nucleic acids.

14. The method of claim 13, wherein:

(i) the drug-sensitive normalised value (dsV) is used as a base value for assessing a presence or an absence of resistance or sensitivity to the drug in the cell, organism or virus; and resistance to the drug is indicated when the normalised value (nV) obtained by said amplification of nucleic acids from the cell, organism, or virus is above the drug-sensitive normalised value (dsV); or sensitivity to the drug is indicated when the normalised value (nV) obtained by said amplification of nucleic acids from the cell, organism, or virus is equal to or below the drug-sensitive normalised value (dsV); and/or (ii) said drug-sensitive normalised value (dsV):

incorporates statistical variation in said series of normalised values (nV) from individuals of the population of the cells, organisms, or viruses known to be sensitive to the drug; and/or is provided with a confidence interval that said drug-sensitive normalised value (dsV) is predictive of a presence or an absence of:

(a) resistance to the drug in the cell, organism or virus; or
(b) sensitivity to the drug in the cell, organism or virus.

15. The method of claim 1, further comprising:

obtaining a drug-resistant normalised value (drV) generated using a series of said normalised values (nV) obtained from individuals of a population of the cells, organisms, or viruses known to resistant to the drug; and comparing the normalised value (nV) obtained by said amplification of nucleic acids from the cell, organism, or virus to the drug-resistant normalised value (drV), to thereby assess the level of drug resistance or drug sensitivity or in the cell, organism, or virus, wherein the cell, organism, or virus has been treated with a drug prior to said amplification of nucleic acids.

16. The method of claim 15 wherein:

(a) the drug-resistant normalised value (drV) is used as a base value for assessing a presence or an absence of resistance or sensitivity to the drug in the cell, organism or virus; and resistance to the drug is indicated when the normalised value (nV) obtained by said amplification of nucleic acids from the cell, organism, or virus is equal to or above the drug-resistant normalised value (drV); or sensitivity to the drug is indicated when the normalised value (nV) obtained by said amplification of nucleic acids from the cell, organism, or virus is below the drug-resistant normalised value (drV); and/or (b) said drug-resistant normalised value (drV):

incorporates statistical variation in said series of normalised values (nV) from individuals of the population of the cells, organisms, or viruses known to be resistant to the drug; and/or is provided with a confidence interval that said drug-resistant normalised value (drV) is predictive of a presence or an absence of:

(i) resistance to the drug in the cell, organism or virus; or
(ii) sensitivity to the drug in the cell, organism or virus.

17. The method of claim 1, further comprising using the normalised value (nV) to assess the level of drug resistance or drug sensitivity in the cell, organism, or virus, wherein:

a first population of said cell, organism, or virus which has been treated with a drug prior to said amplification of nucleic acids, is used to generate a first said normalized value (nV), a second population of said cell, organism, or virus which has not been treated with a drug prior to said amplification of nucleic acids, is used to generate a second said normalized value (nV), said first normalized value (nV) and said second normalized value (nV) are compared to assess the level of transcriptional activity in the cell, organism, or virus with or without drug treatment, and thereby assess the level of drug resistance or drug sensitivity in the cell, organism, or virus.

18. The method of claim 17, wherein said drug sensitivity is indicated when said first normalized value (nV) is lower than said second normalized value (nV).

19. The method of claim 13, wherein:
(i) the drug is selected from the group consisting of: an antimicrobial, aminoglycosides, ansamycins, carbacephem, carbapenems, cephalosporins, glycopeptides, macrolidespenicillins, monobactams, polypeptides, quinolones, sulphonamides, and tetracycline; and/or
(ii) the first gene is a gene from a *Chlamydia* species, a Gonorrhea species, or a *mycoplasma* species.

20. The method of claim 1, wherein:
(i) the cell is a mammalian cell, a human cell, an animal cell, a plant cell, a bacterial cell, a host cell infected by viruses, or a host cell of infected by bacteria; and/or
(ii) the organism is a mammal, a human, a plant, a bacterium, a virus, a fungus, an alga, an archaeon or a protozoan.

* * * * *

UNITED STATES PATENT AND TRADEMARK OFFICE
CERTIFICATE OF CORRECTION

| | | |
|---|---|---|
| PATENT NO. | : 12,123,051 B2 | Page 1 of 2 |
| APPLICATION NO. | : 16/619932 | |
| DATED | : October 22, 2024 | |
| INVENTOR(S) | : Alison Velyian Todd et al. | |

It is certified that error appears in the above-identified patent and that said Letters Patent is hereby corrected as shown below:

On the Title Page

Replace the title page with the attached title page, showing the corrected number of claims.

In the Claims

In Column 84, Lines 49-50, Claim 1, delete "transcriptase;" and insert -- transcriptase; and --, therefor.

In Column 85, Line 2, Claim 2, delete "thereof," and insert -- thereof; --, therefor.

In Column 85, Lines 37-41, delete Claim 4 in its entirety.

In Column 87, Line 19, Claim 11, delete "thereof," and insert -- thereof; --, therefor.

In Column 87, Line 21, Claim 11, delete "(nV±):" and insert -- (nV$^{\pm}$): --, therefor.

In Column 87, Line 26, Claim 11, delete "(nV±)" and insert -- (nV$^{\pm}$) --, therefor.

In Column 88, Line 24, Claim 15, delete "known to" and insert -- known to be --, therefor.

Signed and Sealed this
Third Day of June, 2025

Coke Morgan Stewart
*Acting Director of the United States Patent and Trademark Office*

United States Patent
Todd et al.

(10) Patent No.: US 12,123,051 B2
(45) Date of Patent: Oct. 22, 2024

(54) NUCLEIC ACID RATIO DETERMINATION

(71) Applicant: SpeeDx Pty Ltd, Eveleigh (AU)

(72) Inventors: Alison Velyian Todd, Glebe (AU); Nicole Elizabeth Lima, Cremorne (AU)

(73) Assignee: SPEEDX PTY LTD, Eveleigh (AU)

( * ) Notice: Subject to any disclaimer, the term of this patent is extended or adjusted under 35 U.S.C. 154(b) by 874 days.

(21) Appl. No.: 16/619,932

(22) PCT Filed: Dec. 21, 2018

(86) PCT No.: PCT/AU2018/051406
§ 371 (c)(1),
(2) Date: Dec. 5, 2019

(87) PCT Pub. No.: WO2019/119072
PCT Pub. Date: Jun. 27, 2019

(65) Prior Publication Data
US 2020/0199651 A1    Jun. 25, 2020

(30) Foreign Application Priority Data

Dec. 21, 2017    (AU) ............................... 2017905138

(51) Int. Cl.
*C12Q 1/686* (2018.01)
*C12Q 1/18* (2006.01)
*C12Q 1/6851* (2018.01)
*G16B 20/00* (2019.01)
*G16B 25/10* (2019.01)
*G16B 25/20* (2019.01)

(52) U.S. Cl.
CPC ............... *C12Q 1/686* (2013.01); *C12Q 1/18* (2013.01); *C12Q 1/6851* (2013.01); *G16B 20/00* (2019.02); *G16B 25/10* (2019.02); *G16B 25/20* (2019.02)

(58) Field of Classification Search
None
See application file for complete search history.

(56) References Cited

U.S. PATENT DOCUMENTS 9,694,049 B2 * 7/2017 Burkin .................... G01N 33/15
2009/0305274 A1   12/2009 Gygax et al.

FOREIGN PATENT DOCUMENTS

| AU | 2004266311 A1 * | 3/2005 | .......... C12N 15/113 |
|---|---|---|---|
| CA | 2763608 A1 * | 12/2010 | .......... C12Q 1/6809 |
| CA | 2979373 A1 * | 3/2018 | .......... A61K 31/4439 |
| EP | 0910666 | 8/2006 | |
| WO | WO 2001/20041 | 3/2001 | |
| WO | WO-2011109901 A1 * | 9/2011 | .............. C12Q 1/689 |
| WO | WO 2011/140237 A2 | 11/2011 | |
| WO | WO 2012/171997 A1 | 12/2012 | |

OTHER PUBLICATIONS

Laurell H, Iacovoni JS, Abot A, Svec D, Maoret J-J, Arnal J-F, Kubista M. 2012. Correction of RT-qPCR data for genomic DNA-derived signals with Valid Prime. Nucleic Acids Research 40:7, e51. DOI: 10.1093/nar/gkr1259 (Year: 2012).*
Laurell et al., "Correction of RT-qPCR data for genomic DNA-derived signals with ValidPrime," Nucleic Acids Research, 40(7):e51, 10 pages, (2012).
Leung et al., "A quantitative-PCR based method to estimate ranavirus viral load following normalisation by reference to an ultraconserved vertebrate target," Journal of Virological Methods, 249:147-155, (2017).
Padhi et al., "A PCR-based approach to assess genomic DNA contamination in RNA: Application to rat RNA samples," Analytical Biochemistry, 494:49-51, (2016).
WIPO Application No. PCT/AU2018/005140, PCT International Search Report mailed Feb. 8, 2019.
WIPO Application No. PCT/AU2018/005140, PCT Written Opinion of the International Searching Authority mailed Feb. 8, 2019.
Shimada et al., "Normalization using ploidy and genomic DNA copy numer allows absolute quanification of transcripts, proteins and metabolites in cells," Plant Methods, 6:29, (2010).
EP 18891196.0 European Search Opinion completed Aug. 12, 2021.
EP 18891196.0 Supplemental European Search Report completed Aug. 12, 2021.

* cited by examiner

*Primary Examiner* — Soren Harward
*Assistant Examiner* — Robert James Kallal
(74) *Attorney, Agent, or Firm* — Alston & Bird LLP

(57) ABSTRACT

The present invention provides methods for quantitative data normalisation, and/or ascertaining levels of transcription in cells, organisms, viruses, and the like. The methods can be used in numerous applications including, but not limited to, determining transcriptional upregulation and downregulation, identifying transcriptional perturbation, determining viability/death, and assessing responses to treatment with agents (e.g. resistance or sensitivity to drugs).

19 Claims, 13 Drawing Sheets
Specification includes a Sequence Listing.

SEQUENCE LISTING

```
<160> NUMBER OF SEQ ID NOS: 39

<210> SEQ ID NO 1
<211> LENGTH: 38
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (38)..(38)
<223> OTHER INFORMATION: 3' end phosphate moiety

<400> SEQUENCE: 1
tggtctcgag cattgaacga acaacgagag gaaacctt                          38

<210> SEQ ID NO 2
<211> LENGTH: 38
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (38)..(38)
<223> OTHER INFORMATION: 3' end phosphate moiety

<400> SEQUENCE: 2
```
tgcccaggga ggctagctca tgttctcgat taaggctg        38

<210> SEQ ID NO 3
<211> LENGTH: 22
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(13)
<223> OTHER INFORMATION: ribonucleotides

<400> SEQUENCE: 3
aaggtttcct cguccctggg ca        22

<210> SEQ ID NO 4
<211> LENGTH: 19
<212> TYPE: DNA
<213> ORGANISM: Artificial Sequence
<220> FEATURE:
<223> OTHER INFORMATION: synthetic

<400> SEQUENCE: 4
cttcttcctg ggacgaacg        19

<210> SEQ ID NO 5
<211> LENGTH: 20
<212> TYPE: DNA
<213> ORGANISM: Artificial Sequence
<220> FEATURE:
<223> OTHER INFORMATION: synthetic

<400> SEQUENCE: 5
tggcctgagg aatgtcttgc        20

<210> SEQ ID NO 6
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (37)..(37)
<223> OTHER INFORMATION: 3' end phosphate moiety

<400> SEQUENCE: 6
tggtctcgag cattgaacga acaacgaggg acgtcga        37

<210> SEQ ID NO 7
<211> LENGTH: 38
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (38)..(38)
<223> OTHER INFORMATION: 3' end phosphate moiety

<400> SEQUENCE: 7
cggtagagga ggctagctca tgttctcgat taaggctg        38

<210> SEQ ID NO 8
<211> LENGTH: 40
<212> TYPE: DNA
<213> ORGANISM: Artificial Sequence

```
<220> FEATURE:
<223> OTHER INFORMATION: synthetic
<220> FEATURE:
<221> NAME/KEY: misc_feature
<222> LOCATION: (40)..(40)
<223> OTHER INFORMATION: 3' end phosphate moiety

<400> SEQUENCE: 8
tcgactaaac agaaaatgtc aaaacaacga gaggcgtgat                                40

<210> SEQ ID NO 9
<211> LENGTH: 41
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (41)..(41)
<223> OTHER INFORMATION: 3' end phosphate moiety

<400> SEQUENCE: 9
ctgggaggag aggctagctc aacttgtcaa aaaacagaag g                              41

<210> SEQ ID NO 10
<211> LENGTH: 21
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (11)..(12)
<223> OTHER INFORMATION: ribonucleotides

<400> SEQUENCE: 10
tcgacgtccc gucctctacc g                                                   21

<210> SEQ ID NO 11
<211> LENGTH: 22
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (11)..(12)
<223> OTHER INFORMATION: ribonucleotides

<400> SEQUENCE: 11
atcacgcctc guctcctccc ag                                                  22

<210> SEQ ID NO 12
<211> LENGTH: 23
<212> TYPE: DNA
<213> ORGANISM: Artificial Sequence
<220> FEATURE:
<223> OTHER INFORMATION: synthetic

<400> SEQUENCE: 12
gagagagtga ttatatcgac taa                                                 23

<210> SEQ ID NO 13
<211> LENGTH: 23
<212> TYPE: DNA
<213> ORGANISM: Artificial Sequence
<220> FEATURE:
<223> OTHER INFORMATION: synthetic
```

<400> SEQUENCE: 13
caagagagaa tgtcaaaaga tac                                                        23

<210> SEQ ID NO 14
<211> LENGTH: 38
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (38)..(38)
<223> OTHER INFORMATION: 3' end phosphate moiety

<400> SEQUENCE: 14
ttgcaccact tggtgtgacg acaacgagag gaaacctt                                        38

<210> SEQ ID NO 15
<211> LENGTH: 39
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (39)..(39)
<223> OTHER INFORMATION: 3' end phosphate moiety

<400> SEQUENCE: 15
tgcccaggga ggctagctct atcagcatgc gtgtgggtt                                       39

<210> SEQ ID NO 16
<211> LENGTH: 24
<212> TYPE: DNA
<213> ORGANISM: Artificial Sequence
<220> FEATURE:
<223> OTHER INFORMATION: synthetic

<400> SEQUENCE: 16
tttcggcgga gatccttgcg atcc                                                       24

<210> SEQ ID NO 17
<211> LENGTH: 25
<212> TYPE: DNA
<213> ORGANISM: Artificial Sequence
<220> FEATURE:
<223> OTHER INFORMATION: synthetic

<400> SEQUENCE: 17
cgaaaacaaa gtcaccgtag taacc                                                      25

<210> SEQ ID NO 18
<211> LENGTH: 41
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (41)..(41)
<223> OTHER INFORMATION: 3' end phosphate moiety

<400> SEQUENCE: 18
attgaacgac atgttctcga ttaaacaacg agggacgtcg a                                    41

<210> SEQ ID NO 19
<211> LENGTH: 40

```
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (40)..(40)
<223> OTHER INFORMATION: 3' end phosphate moiety

<400> SEQUENCE: 19
cggtagagga ggctagctgg ctgcttttac ttgcaagaca                40

<210> SEQ ID NO 20
<211> LENGTH: 38
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (38)..(38)
<223> OTHER INFORMATION: 3' end phosphate moiety

<400> SEQUENCE: 20
cttgcaccac ttggtgtgac gacaacgagg gacgtcga                  38

<210> SEQ ID NO 21
<211> LENGTH: 40
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (40)..(40)
<223> OTHER INFORMATION: 3' end phosphate moiety

<400> SEQUENCE: 21
cggtagagga ggctagctct atcagcatgc gtgtgggtta                40

<210> SEQ ID NO 22
<211> LENGTH: 23
<212> TYPE: DNA
<213> ORGANISM: Artificial Sequence
<220> FEATURE:
<223> OTHER INFORMATION: synthetic

<400> SEQUENCE: 22
caattaatgg cctgaggaat gtc                                  23

<210> SEQ ID NO 23
<211> LENGTH: 23
<212> TYPE: DNA
<213> ORGANISM: Artificial Sequence
<220> FEATURE:
<223> OTHER INFORMATION: synthetic

<400> SEQUENCE: 23
gcaaaaactc aagagagaat gtc                                  23

<210> SEQ ID NO 24
<211> LENGTH: 27
<212> TYPE: DNA
<213> ORGANISM: Artificial Sequence
<220> FEATURE:
<223> OTHER INFORMATION: synthetic

<400> SEQUENCE: 24
```
gagctataat tagctctctt tgtgctc    27

<210> SEQ ID NO 25
<211> LENGTH: 22
<212> TYPE: DNA
<213> ORGANISM: Artificial Sequence
<220> FEATURE:
<223> OTHER INFORMATION: synthetic

<400> SEQUENCE: 25
gatatccact ggtggctcct aa    22

<210> SEQ ID NO 26
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (37)..(37)
<223> OTHER INFORMATION: 3' end phosphate moiety

<400> SEQUENCE: 26
ggttgcctac tatctgcaga acaacgagag gactagg    37

<210> SEQ ID NO 27
<211> LENGTH: 35
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (35)..(35)
<223> OTHER INFORMATION: 3' end phosphate moiety

<400> SEQUENCE: 27
gacgtgagga ggctagctcg cgcggcgtgg cggct    35

<210> SEQ ID NO 28
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (37)..(37)
<223> OTHER INFORMATION: 3' end phosphate moiety

<400> SEQUENCE: 28
acgacagcat tgccaaagtg acaacgagag gactagg    37

<210> SEQ ID NO 29
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (37)..(37)
<223> OTHER INFORMATION: 3' end phosphate moiety

<400> SEQUENCE: 29
gacgtgagga ggctagctcc gaacgaagcg gcttttg    37

```
<210> SEQ ID NO 30
<211> LENGTH: 38
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (38)..(38)
<223> OTHER INFORMATION: 3' end phosphate moiety

<400> SEQUENCE: 30
tgcttttgct gtgaaaaagg gacaacgaga gggtcgag                    38

<210> SEQ ID NO 31
<211> LENGTH: 39
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (39)..(39)
<223> OTHER INFORMATION: 3' end phosphate moiety

<400> SEQUENCE: 31
ggacgaggga ggctagctct gaaattgcca acaatcctg                   39

<210> SEQ ID NO 32
<211> LENGTH: 21
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (11)..(12)
<223> OTHER INFORMATION: ribonucleotides

<400> SEQUENCE: 32
cctagtcctc guccctcacgt c                                     21

<210> SEQ ID NO 33
<211> LENGTH: 21
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (11)..(12)
<223> OTHER INFORMATION: ribonucleotides

<400> SEQUENCE: 33
ctcgaccctc guccctcgtc c                                      21

<210> SEQ ID NO 34
<211> LENGTH: 20
<212> TYPE: DNA
<213> ORGANISM: Artificial Sequence
<220> FEATURE:
<223> OTHER INFORMATION: synthetic

<400> SEQUENCE: 34
cggcacgcaa atcgaaatcc                                        20

<210> SEQ ID NO 35
<211> LENGTH: 18
<212> TYPE: DNA
```

```
<213> ORGANISM: Artificial Sequence
<220> FEATURE:
<223> OTHER INFORMATION: synthetic

<400> SEQUENCE: 35
tgcgcgcggc cttcaacc                                                    18

<210> SEQ ID NO 36
<211> LENGTH: 19
<212> TYPE: DNA
<213> ORGANISM: Artificial Sequence
<220> FEATURE:
<223> OTHER INFORMATION: synthetic

<400> SEQUENCE: 36
cttggtggac gctcatgca                                                   19

<210> SEQ ID NO 37
<211> LENGTH: 22
<212> TYPE: DNA
<213> ORGANISM: Artificial Sequence
<220> FEATURE:
<223> OTHER INFORMATION: synthetic

<400> SEQUENCE: 37
gccttctttt tccgccatta ca                                               22

<210> SEQ ID NO 38
<211> LENGTH: 20
<212> TYPE: DNA
<213> ORGANISM: Artificial Sequence
<220> FEATURE:
<223> OTHER INFORMATION: synthetic

<400> SEQUENCE: 38
gttttcacgc ctgcttttgc                                                  20

<210> SEQ ID NO 39
<211> LENGTH: 20
<212> TYPE: DNA
<213> ORGANISM: Artificial Sequence
<220> FEATURE:
<223> OTHER INFORMATION: synthetic

<400> SEQUENCE: 39
gacgctcaaa acgcggacga                                                  20
```